| (12) | United States Patent<br>Pun et al. | (10) Patent No.: US 12,215,324 B2<br>(45) Date of Patent: Feb. 4, 2025 |

(54) MONOCYTE AND MACROPHAGE BINDING APTAMERS AND THEIR APPLICATION

(71) Applicants: University of Washington, Seattle, WA (US); Seattle Children's Hospital, Seattle, WA (US)

(72) Inventors: Suzie Hwang Pun, Seattle, WA (US); Meilyn Sylvestre, Seattle, WA (US); Nataly Kacherovsky, Seattle, WA (US); Emmeline Cheng, Seattle, WA (US); Ian Cardle, Seattle, WA (US); Chris Saxby, Seattle, WA (US)

(73) Assignees: University of Washington, Seattle, WA (US); Seattle Children's Hospital, Seattle, WA (US)

( * ) Notice: Subject to any disclaimer, the term of this patent is extended or adjusted under 35 U.S.C. 154(b) by 72 days.

(21) Appl. No.: 17/849,513

(22) Filed: Jun. 24, 2022

(65) Prior Publication Data

US 2023/0017777 A1    Jan. 19, 2023

Related U.S. Application Data

(60) Provisional application No. 63/214,468, filed on Jun. 24, 2021.

(51) Int. Cl.
| | |
|---|---|
| *C12N 15/115* | (2010.01) |
| *A61K 39/00* | (2006.01) |
| *C12N 5/0786* | (2010.01) |
| *C12N 15/10* | (2006.01) |

(52) U.S. Cl.
CPC ........ *C12N 15/115* (2013.01); *A61K 39/4614* (2023.05); *A61K 39/4622* (2023.05); *A61K 39/4644* (2023.05); *C12N 5/0645* (2013.01); *C12N 15/1048* (2013.01); *C12N 15/1065* (2013.01); *A61K 2239/31* (2023.05); *A61K 2239/38* (2023.05); *C12N 2310/16* (2013.01)

(58) Field of Classification Search
CPC ............... C12N 15/115; C12N 5/0645; C12N 15/1048; C12N 15/1065; C12N 2310/16
See application file for complete search history.

(56) References Cited

PUBLICATIONS

Acinas, Silvia G., et al. "PCR-induced sequence artifacts and bias: insights from comparison of two 16S rRNA clone libraries constructed from the same sample." Applied and environmental microbiology 71.12 (2005): 8966-8969.
Alam, Khalid K., Jonathan L. Chang, and Donald H. Burke. "FASTAptamer: a bioinformatic toolkit for high-throughput sequence analysis of combinatorial selections." Molecular Therapy-Nucleic Acids 4 (2015): e230.
Alshaer, Walhan, Herve Hillaireau, and Elias Fattal. "Aptamer-guided nanomedicines for anticancer drug delivery." Advanced drug delivery reviews 134 (2018): 122-137.
Andon, Fernando Torres, et al. "Targeting tumor associated macrophages: the new challenge for nanomedicine." Seminars in immunology 34 (2017): 103-113.
Ayala-Nunez, Nilda Vanesa, et al. "Zika virus enhances monocyte adhesion and transmigration favoring viral dissemination to neural cells." Nature communications 10.4430 (2019): 1-16.
Bailey, Timothy L., et al. "MEME Suite: tools for motif discovery and searching." Nucleic acids research 37 (2009): W202-W208.
Bingle, L., N. J. Brown, and Claire E. Lewis. "The role of tumour-associated macrophages in tumour progression: Implications for new anticancer therapies." The Journal of Pathology: Journal of Pathological 196.3 (2002): 254-265.
Chen, Liang, et al. "The isolation of an RNA aptamer targeting to p53 protein with single amino acid mutation." Proceedings of the National Academy of Sciences 112.32 (2015): 10002-10007.
Cieslewicz, Maryelise, et al. "Targeted delivery of proapoptotic peptides to tumor-associated macrophages improves survival." Proceedings of the National Academy of Sciences 110.40 (2013): 15919-15924.
Ding, Ding, et al. "Improving tumor accumulation of aptamers by prolonged blood circulation." Analytical chemistry 92.5 (2020): 4108-4114.
Dong, Xinyue, Dafeng Chu, and Zhenjia Wang. "Leukocyte-mediated delivery of nanotherapeutics in inflammatory and tumor sites." Theranostics 7.3 (2017): 751-763.
Hou, Jia, et al. "Accessing neuroinflammation sites: Monocyte/neutrophil-mediated drug delivery for cerebral ischemia." Science advances 5.7 (2019): eaau8301.
Hou, Wanqiu, et al. "Viral infection triggers rapid differentiation of human blood monocytes into dendritic cells." Blood, The Journal of the American Society of Hematology 119.13 (2012): 3128-3131.
Iliuk, Anton B., Lianghai Hu, and W. Andy Tao. "Aptamer in bioanalytical applications." Analytical chemistry 83.12 (2011): 4440-4452.
Kacherovsky, Nataly, et al. "Traceless aptamer-mediated isolation of CD8+ T cells for chimeric antigen receptor T-cell therapy." Nature biomedical engineering 3.10 (2019): 783-795.
Kalos, Michael, et al. "T cells with chimeric antigen receptors have potent antitumor effects and can establish memory in patients with advanced leukemia." Science translational medicine 3.95 (2011): 1-21.
Kapellos, Theodore S., et al. "Human monocyte subsets and phenotypes in major chronic inflammatory diseases." Frontiers in immunology, 10.2035 (2019).
Keefe, Anthony D., Supriya Pai, and Andrew Ellington. "Aptamers as therapeutics." Nature reviews Drug discovery 9.7 (2010): 537-550.

(Continued)

*Primary Examiner* — J. E. Angell
(74) *Attorney, Agent, or Firm* — Christensen O'Connor Johnson Kindness PLLC

(57) ABSTRACT

Provided herein are compositions comprising aptamers that specifically bind monocytes and/or macrophage and methods for their use. These aptamer compositions can be used in methods for isolating and/or enriching monocytes and/or macrophages or depleting cell populations of monocytes and/or macrophages. Further provided are methods of using the aptamers or cell populations generated using them in the methods disclosed herein for therapies and/or drug delivery.

20 Claims, 35 Drawing Sheets
(14 of 35 Drawing Sheet(s) Filed in Color)
Specification includes a Sequence Listing.

(56) References Cited

PUBLICATIONS

Klichinsky, Michael, et al. "Human chimeric antigen receptor macrophages for cancer immunotherapy." Nature biotechnology 38.8 (2020): 947-953.

Mallikaratchy, Prabodhika R., et al. "A multivalent DNA aptamer specific for the B-cell receptor on human lymphoma and leukemia." Nucleic acids research 39.6 (2011): 2458-2469.

Mantovani, Alberto, et al. "Macrophage polarization: tumor-associated macrophages as a paradigm for polarized M2 mononuclear phagocytes." Trends in immunology 23.11 (2002): 549-555.

Mantovani, Alberto, et al. "The chemokine system in diverse forms of macrophage activation and polarization." Trends in immunology 25.12 (2004): 677-686.

Martinez, Fernando O., and Siamon Gordon. "The M1 and M2 paradigm of macrophage activation: time for reassessment." F1000prime reports 6:13 (2014).

McGrath, Kathleen E., Jenna M. Frame, and James Palis. "Early hematopoiesis and macrophage development." Seminars in immunology. Seminars in Immunology 27 (2015) 379-387.

Meng, Hong-Min, et al. "Aptamer-integrated DNA nanostructures for biosensing, bioimaging and cancer therapy." Chemical Society Reviews 45.9 (2016): 2583-2602.

Morrissey, Meghan A., et al. "Chimeric antigen receptors that trigger phagocytosis." elife 7 (2018): e36688.

Moyes, Kara W., et al. "Genetically engineered macrophages: a potential platform for cancer immunotherapy." Human gene therapy 28.2 (2017): 200-215.

Muraoka, Daisuke, et al. "Antigen delivery targeted to tumor-associated macrophages overcomes tumor immune resistance." The Journal of clinical investigation 129.3 (2019): 1278-1294.

Ngambenjawong, Chayanon, Heather H. Gustafson, and Suzie H. Pun. "Progress in tumor-associated macrophage (TAM)-targeted therapeutics." Advanced drug delivery reviews 114 (2017): 206-221.

Nikitina, Ekaterina, et al. "Monocytes and macrophages as viral targets and reservoirs." International journal of molecular sciences 19.9 (2018): 2821.

Noy, Roy, and Jeffrey W. Pollard. "Tumor-associated macrophages: from mechanisms to therapy." Immunity 41.1 (2014): 49-61.

Olingy, Claire E., Huy Q. Dinh, and Catherine C. Hedrick. "Monocyte heterogeneity and functions in cancer." Journal of leukocyte biology 106.2 (2019): 309-322.

Qian, Bin-Zhi, et al. "CCL2 recruits inflammatory monocytes to facilitate breast-tumour metastasis." Nature 475.7355 (2011): 222-225.

Ray, Partha, and Rebekah R. White. "Aptamers for targeted drug delivery." Pharmaceuticals 3.6 (2010): 1761-1778.

Ries, Carola H., et al. "Targeting tumor-associated macrophages with anti-CSF-1R antibody reveals a strategy for cancer therapy." Cancer cell 25.6 (2014): 846-859.

Sanchez-Torres, Carmen, et al. "CD16+ and CD16—human blood monocyte subsets differentiate in vitro to dendritic cells with different abilities to stimulate CD4+ T cells." International immunology 13.12 (2001): 1571-1581.

Sefah, Kwame, et al. "Development of DNA aptamers using Cell-SELEX." Nature protocols 5.6 (2010): 1169-1185.

Sharma, Padmanee, and James P. Allison. "The future of immune checkpoint therapy." Science 348.6230 (2015): 56-61.

Shigdar, Sarah, et al. "Aptamers as theranostic agents: modifications, serum stability and functionalisation." Sensors 13.10 (2013): 13624-13637.

Sica, Antonio, and Alberto Mantovani. "Macrophage plasticity and polarization: in vivo veritas." The Journal of clinical investigation 122.3 (2012): 787-795.

Siegel, Georg, et al. "Phenotype, donor age and gender affect function of human bone marrow-derived mesenchymal stromal cells." BMC medicine 11.146 (2013): 1-20.

Sippel, Trisha R., et al. "Human hematopoietic stem cell maintenance and myeloid cell development in next-generation humanized mouse models." Blood advances 3.3 (2019): 268-274.

Sylvestre, Meilyn, Courtney A. Crane, and Suzie H. Pun. "Progress on modulating tumor-associated macrophages with piomaterials." Advanced Materials 32.13 (2020): 1902007.

Sylvestre, Meilyn, et al. "Identification of a DNA aptamer that binds to human monocytes and macrophages." Bioconjugate Chemistry 31.8 (2020): 1899-1907.

Taylor, Sean C., Genevieve Laperriere, and Hugo Germain. "Droplet Digital PCR versus qPCR for gene expression analysis with low abundant targets: from variable nonsense to publication quality data." Scientific reports 7.2409 (2017): 1-8.

Tuleuova, Nazgul, and Alexander Revzin. "Micropatterning of aptamer beacons to create cytokine-sensing surfaces." Cellular and molecular bioengineering 3.4 (2010): 337-344.

Tumeh, Paul C., et al. "PD-1 blockade induces responses by inhibiting adaptive immune resistance." Nature 515.7528 (2014): 568-571.

Wang, Guodong, et al. "Selection and characterization of DNA aptamer against glucagon receptor by cell-SELEX." Scientific reports 7.7179 (2017): 1-10.

Yong, Kylie Su Mei, Zhisheng Her, and Qingfeng Chen. "Humanized mice as unique tools for human-specific studies." Archivum immunologiae et therapiae experimentalis 66.4 (2018): 245-266.

Zeisberger, S. M., et al. "Clodronate-liposome-mediated depletion of tumour-associated macrophages: a new and highly effective antiangiogenic therapy approach." British journal of cancer 95.3 (2006): 272-281.

| Cell-SELEX schematic | | | | | | | |
|---|---|---|---|---|---|---|---|
| | Positive Selection (M2 Macrophages) | | | | | Negative Selection | |
| Round | # cells | ssDNA Conc. | Duration | BSA/DHS | # washes | Cell type | # cells |
| 1 | ~6M | 500 nM | 1 hr | 0.1% BSA | 3 | Plastic | |
| 2 | ~3M | 500 nM | 1 hr | 0.1% BSA | 3 | Monocytes | 10M |
| 3 | ~3M | 500 nM | 45 min | 0.5% BSA | 4 | Monocytes | 10M |
| 4 | ~3M | 350 nM | 45 min | 1% BSA | 4 | MO | ~3M |
| 5 | ~3M | 268 nM | 30 min | 2.5% BSA | 4 | MO | ~6M |
| 6 | ~3M | 333 nM | 30 min | 2.5% BSA | 4 | MO | ~6M |
| 7 | ~2M | 250 nM | 30 min | 5% BSA | 4 | MO | ~8M |
| 8 | ~1.6M | 250 nM | 30 min | 5% DHS | 4 | MO | ~7M |
| 9 | ~1.6M | 200 nM | 30 min | 10% DHS | 4 | MO | ~7M |

*FIG. 1B*

| | $K_d$ (nM) |
|---|---|
| M0 | 44.12 ± 8.0 |
| M1 | 22.79 ± 11.4 |
| M2 | 22.81 ± 5.6 |

| Rank | Aptamer % representation of all reads in each round | | | | | Enrichment between rounds y/x | | | |
|---|---|---|---|---|---|---|---|---|---|
| | % R9 | % R8 | % R7 | % R6 | % R5 | 9/8 | 8/7 | 7/6 | 6/5 |
| 1 | 21 | 10 | 2 | 0 | 0 | 2 | 4 | 6 | 12 |
| 2 | 3 | 1 | 0 | 0 | 0 | 4 | 5 | 3 | 26 |
| 3 | 3 | 4 | 2 | 0 | 0 | 1 | 2 | 3 | 33 |
| 4 | 2 | 3 | 5 | 3 | 0 | 1 | 1 | 2 | 62 |
| 5 | 2 | 1 | 1 | 1 | 0 | 2 | 1 | 1 | 20 |
| 6 | 2 | 1 | 0 | 0 | 0 | 2 | 7 | 9 | 14 |
| 7 | 2 | 1 | 0 | 0 | 0 | 2 | 8 | 7 | 12 |
| 8 | 1 | 1 | 0 | 0 | 0 | 2 | 4 | 10 | 28 |
| 9 | 1 | 1 | 1 | 0 | 0 | 1 | 2 | 2 | 11 |
| 10 | 1 | 1 | 0 | 0 | 0 | 2 | 7 | 9 | 18 |

FIG. 6A

| Motif | Motif Sequence from meme-suite.org | |
|---|---|---|
| Motif 1 | [sequence logo: CGCACCCT] | SEQ ID NO: 17 |
| Motif 2 | [sequence logo: AGCCATCGG...T] | SEQ ID NO: 18 |
| Motif 3 | [sequence logo: CCACAAGATT] | SEQ ID NO: 19 |
| Motif 4 | [sequence logo: ATCGGTTAAACTAGAAACC] | SEQ ID NO: 20 |

*FIG. 6C*

SEQ ID NO: 21

DNA sequences used in this work

| Oligonucleotide | Sequence |
| --- | --- |
| 52-Base Pair Library Design | 5'-ATCCAGAGTGACGCAGCA-52N-TGGACACGGGTGGCTTAGT-3' |
| A2 Aptamer | GAAGAGTAGATGAAACGTTTTTCGCCCGATAAAAGGGACGTGCGTCAGACA |
| SCRM Aptamer | ATGATAGTGACGTACGGACTAGGATCACCCATATCATGTAGAGGAAGTACG |

| Primer | Sequence |
| --- | --- |
| Aptamer Forward Primer | 5'-FAM-ATCCAGAGTGACGCAGCA-3' |
| Aptamer Reverse Primer | 5'-biotin-ACTAAGCCACCGTGTCCA-3' |
| Extended Aptamer Forward Primer | 5'-GCATCCAGAGTGACGCAGCA-3' |
| Extended Aptamer Reverse Primer | 5'-GCACTAAGCCACCGTGTCCA-3' |
| rRNA 12S Forward Primer | 5'-AAACTGCTCGCCAGAACACT-3' |
| rRNA 12S Reverse Primer | 5'-CATGGGCTACACCTTGACCT-3' |

*FIG. 8D*

MONOCYTE AND MACROPHAGE BINDING APTAMERS AND THEIR APPLICATION

CROSS-REFERENCE TO RELATED APPLICATION

This application claims the benefit of U.S. Provisional Application No. 63/108,217, filed Jun. 24, 2021, the disclosure of which is hereby incorporated by reference in its entirety.

GOVERNMENT SUPPORT

This invention was made with government support under Grant No. R01 CA177272, awarded by the National Institute of Health Sciences. The government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 3915-P1255US.UW_Substitute-Sequence-Listing_ST25.txt. The text file is 6 KB; was created on Jul. 27, 2023; and is being submitted via Patent Center with the filing of the specification.

TECHNICAL FIELD

The field of the invention relates to compositions and their use in methods of isolating or depleting monocytes and macrophages from a biological sample, delivery of drugs to such cells, and/or treatment with the resulting therapeutic cell compositions.

BACKGROUND

Aptamers, like peptides generated by phage display or monoclonal antibodies (MAbs), are capable of specifically binding to selected target molecules, which make aptamers useful in methods of cell purification. Aptamers also offer specific competitive advantages over antibodies, for example, they can be easily synthesized, and can be chemically manipulated with relative ease. Aptamer synthesis is inexpensive and highly reproducible. For example, aptamers can be produced by solid phase chemical synthesis, an accurate and reproducible process with consistency among production batches. An aptamer can be produced in large quantities by polymerase chain reaction (PCR), and, once the sequence is known, can be assembled from individual naturally occurring nucleotides and/or synthetic nucleotides.

SUMMARY

The compositions and methods described herein are based, in part, on the discovery of aptamer sequences that specifically bind to monocytes and/or macrophages. Provided herein are such aptamers, as well as compositions, methods, and therapeutics using them. Also provided herein are methods for isolating or enriching monocytes and/or macrophages, or alternatively, methods for depleting monocytes and/or macrophages from a given heterogeneous cell population.

Accordingly, provided herein in one aspect is a composition comprising an aptamer that specifically binds to a monocyte and/or a macrophage, wherein the aptamer comprises a sequence having at least 75% sequence identity (e.g., at least 75%, at least 80%, at least 85%, at least 90%, at least 95% or more) to SEQ ID NO:1; and wherein the aptamer can further comprise a number (N) of nucleotides at each end wherein each nucleotide is selected independently, and wherein each N comprises from 3 nt to 30 nt, from 3 nt to 20 nt, or from 3 nt to 10 nt. SEQ ID NO:2, or SEQ ID NO:3. In certain embodiments, the aptamer can comprise the sequence having at least 75% identity, (e.g., at least 75%, at least 80%, at least 85%, at least 90%, at least 95% or more) of SEQ ID NO:2 or SEQ ID NO:3.

In one embodiment of this aspect and all other aspects described herein, the monocyte and/or macrophage expresses CD14.

In another embodiment of this aspect and all other aspects provided herein, the macrophage is an M0 or M2 macrophage.

In another embodiment of this aspect and all other aspects provided herein, the aptamer comprises at least five single-stranded loop regions and at least four double-stranded regions.

In yet another embodiment of this aspect and all other aspects provided herein, the aptamer comprises the sequence of SEQ ID NO:1.

In another embodiment of this aspect and all other aspects provided herein, the aptamer is attached to a solid support or phase-changing agent.

In another embodiment of this aspect and all other aspects provided herein, the aptamer further comprises a detectable moiety, a label, a tag or a probe.

In another embodiment of this aspect and all other aspects provided herein, the composition comprising any one of the above aptamers is formulated for use as a drug delivery device, or for use as a sensor.

Another aspect provided herein is a cell displaying an aptamer that specifically binds to a monocyte and/or a macrophage, wherein the aptamer comprises a sequence having at least 75% sequence identity (e.g., at least 75%, at least 80%, at least 85%, at least 90%, at least 95% or more) or differs by less than three nucleotides to SEQ ID NO: 1, SEQ ID NO: 2, or SEQ ID NO:3.

In another aspect provided herein is a method for isolating or enriching monocytes and macrophages from a biological sample comprising a plurality of cell types, the method comprising: (i) contacting the biological sample with an aptamer described herein that specifically binds a monocyte and/or macrophage under conditions that permit forming aptamer-bound cells; and (ii) separating the aptamer-bound cells from cells not bound to the aptamer.

In an embodiment of this aspect and all aspects provided herein the biological sample comprises a blood sample or a processed blood sample.

In an embodiment of this aspect and all other aspects provided herein, the aptamer is attached to a solid support or phase-changing agent.

In an embodiment of this aspect and all other aspects provided herein, the aptamer further comprises a detectable moiety, a label, a tag or a probe.

Another aspect provided herein is a method for depleting monocytes and macrophages from a biological sample comprising a plurality of cell types, the method comprising: (i) contacting the biological sample with an aptamer as described herein that specifically binds a monocyte and/or macrophage under conditions that permit forming an aptamer-bound cell; (ii) separating the aptamer-bound cells from cells not bound to the aptamer; and (iii) recovering the cells not bound to the aptamer by removing aptamer-bound cells, whereby the monocytes and/or macrophages are depleted from the biological sample.

In an embodiment of this aspect and all other aspects provided herein, the biological sample comprises a blood sample or a processed blood sample.

Another aspect provided herein is a pharmaceutical composition comprising an aptamer of as described herein.

Another aspect provided herein is a method of treating a disease, the method comprising: administering the isolated or enriched monocytes and/or macrophages described herein or an engineered or differentiated cell thereof to a subject in need thereof, thereby treating the disease.

Another aspect provided herein is a method of treating a disease, the method comprising administering the recovered cells described herein or an engineered or differentiated cell thereof to a subject in need thereof, thereby treating the disease.

Another aspect provided herein is a method of delivering a therapeutic agent, the method comprising administering an aptamer having at least 75% sequence identity (e.g., at least 75%, at least 80%, at least 85%, at least 90%, at least 95% or more) to SEQ ID NO: 1, 2 or 3, wherein the aptamer is attached to a therapeutic drug or therapeutic cell.

BRIEF DESCRIPTION OF DRAWINGS

This patent or application file contains at least one drawing executed in color. Copies of this patent or patent application publication with color drawing(s) will be provided by the Office upon request and payment of the necessary fee.

FIGS. 1A-1B: Cell-SELEX schematic for a method that permits aptamer selection. FIG. 1A, Cell-SELEX was employed using a 52N-random region DNA aptamer library. Aptamer pools were incubated with positive selection cells and non-binding sequences were removed; aptamer sequences that bound positive selection cells (M2-like macrophages) were recovered and incubated with negative selection cells (M0-like macrophages and monocytes). The sequences that did not bind negative selection cells were recovered, amplified, and used in the next round of selection. FIG. 1B, Stringency was increased in each subsequent round by (i) decreasing the number of positive selection cells, (ii) increasing the number of negative selection cells, (iii) decreasing the incubation time with positive selection cells, (iv) increasing the serum content, and/or (v) increasing the number of washes following incubation with aptamer pools.

FIGS. 2A-2B, Aptamers A2 (FIG. 2A) and SCRM (FIG. 2B) were bound to human M0-, M1-, and M2-like macrophages, and apparent dissociation constants ($K_d$) were calculated. FIG. 2C, Calculated dissociation constants for aptamer A2 binding to M0-, M1-, and M2-like human macrophages. FIG. 2D, Aptamer binding to macrophages was confirmed across unique donors. Aptamer A2 binding to M0-like macrophages was significantly higher than binding to M1-like macrophages (*p=0.03). A2 binding was significantly higher than SCRM binding to M0- (*p=0.0002) and M2-like (p=0.006) macrophages. There was no significant difference between A2 and SCRM binding to M1-like macrophages. FIG. 2E, Representative images of aptamer binding to human TNBC sections with DAPI nuclear stain (blue), CD206 macrophage stain (green), and aptamer (red). Analyzed region-of-interest (ROI) is outlined in yellow and is equivalent between images. Aptamer A2 correlation with CD206 was significantly higher than SCRM correlation with CD206 (**p=0.005). Images in the left column show single cell magnification.

FIG. 3A, Aptamer A2 binding (right) was compared to a scrambled aptamer control (left) in PBMCs, staining with antibodies against CD14 (monocytes), CD19 (B-cells), CD3 (T-cells), or CD56 (natural killer cells). FIG. 3B, Aptamer binding (A2 vs. SCRM) was assessed across unique human blood donors (**p<0.0001). FIG. 3C, Aptamer A2 bound to $CD14^+$ population of PBMCs with an apparent dissociation constant of approximately 45±9.1 nM. FIG. 3D, Aptamer internalization was assessed by incubation with monocytes, followed by removal of external receptors by trypsin 0.25%. Aptamer fluorescence was determined by flow cytometry (**p<0.0001). FIG. 3E, Aptamer A2 binding to monocyte $CD14^+$ and $CD16^+$ populations was assessed. FIG. 3F, Aptamer internalization was assessed by confocal microscopy. Cells were stained with DAPI (blue, nucleus), phalloidin (green, actin), and aptamer (magenta).

FIG. 4A, Monocytes were injected i.p. (t=0 minutes), followed by aptamer injection i.p. (t=10 minutes). After 30 minutes (t=40 minutes), cells were recovered from the peritoneal cavity and assessed by flow cytometry for anti-CD14 antibody and aptamer staining. FIGS. 4B-4C, Recovered cells were gated on anti-CD14 antibody staining and assessed for aptamer fluorescence. Results are shown as a histogram (FIG. 4B) or bar graph (FIG. 4C), normalized to fluorescence of SCRM aptamer (**p<0.0001). FIG. 4D, Percent of $CD14^+$ cells that stained for aptamer (**p<0.0001).

FIGS. 6A-6C: Aptamer sequence analysis. FIG. 6A, FASTAptamer was used to determine aptamer representation based on reads per million (RPM), as well as aptamer enrichment between rounds. Enrichment was calculated as (RPM of round y)/(RPM of round x). The table represents an example analysis of the top 100 aptamers from round 9. Purchased aptamers are shaded. FIG. 6B, Motifs of the top 200 sequences (based on RPM) were tracked through rounds. The top 200 sequences from round 9 are displayed in a phylogenetic tree and the motif sequences are displayed in the table, FIG. 6C. Aptamers with conserved motifs are indicated in the tree. Purchased aptamers are denoted with an asterisk (*).

FIGS. 8A-8D: Aptamer binding, structure and DNA sequences. FIGS. 8A-8B, Selected aptamers were bound against M0-, M1-, and M2-like macrophages and analyzed using flow cytometry (FIG. 8A) or ddPCR (FIG. 8B). FIG. 8C, The predicted free structure of DNA aptamer A2 at 4°

C. using Nupack™. FIG. 8D, Table of the aptamer and primer sequences described herein. SEQ ID NOs: 7 and 8 make up the 52-Base Pair library design sequence joined with a 52 nucleotide random sequence N; SEQ ID NO:9 is the A2 aptamer; SEQ ID NO:10 is the SCRM aptamer; SEQ ID NO:11 is the FAM derivatized aptamer forward primer; SEQ ID NO:12 is the biotin derivatized aptamer reverse primer; SEQ ID NO:13 is the extended aptamer forward primer; SEQ ID NO:14 is the extended aptamer reverse primer; SEQ ID NO:15 is the rRNA 12S forward primer; and SEQ ID NO:16 is the rRNA 12S reverse primer.

FIG. 9A, Murine macrophages were cultured from isolated bone marrow and polarized to M0-, M1-, and M2-like phenotypes. There was no significant difference in binding of A2 and SCRM. FIG. 9B, PBMCs were isolated from murine blood by Ficoll gradient and assessed for binding to monocytes ($CD45^+LyG^-CD11b^+$), $CD4^+$ T-cells ($CD45^+CD3^+CD4^+$) and $CD8^+$ T-cells ($CD45^+CD3^+CD8^+$) by flow cytometry. There was no significant difference in binding of A2 and SCRM.

FIG. 10A, THP-1 macrophages were polarized to M0-, M1-, and M2-like phenotypes and aptamer binding was assessed by flow cytometry. FIGS. 10B-10C, Aptamer binding to THP-1 monocytes (FIG. 10B) and U937 monocytes (FIG. 10C) was assessed by flow cytometry.

FIG. 11A, Aptamer A2 (middle line) binding to purified CD14 binding was compared to a nonspecific aptamer control (top line). Aptamer-protein association was measured by changes in optical readout. FIG. 11B, Jurkat cells were transfected to express the CD14 receptors. Aptamer (A2 medium gray, SCRM light gray) binding to transfected cells was assessed by flow cytometry. The dark gray is the region of overlap.

FIG. 12A, Aptamer sequence were truncated to investigate how the sequence related to binding behavior. Sequences were truncated and secondary structures were predicted with Nupack™ using the following parameters: temperature 4° C.; 0.137 M $Na^+$; and 0.002 M $Mg^{++}$. FIGS. 12B-12C, Aptamer binding was tested as follows: monocytes were freshly isolated from PBMCs using the Miltenyi™ Monocyte Isolation Kit II. Isolated monocytes were stained for viability with Zombie™ Violet, washed, and incubated with folded aptamer at indicated concentrations for 20 minutes on ice in binding buffer (DPBS without ions supplemented with 0.45% glucose, 5 mM $MgCl_2$, 10% DHS, and 100 ug/mL tRNA). Cells were washed, fixed, and binding was analyzed on a flow cytometer. Of the three truncated aptamers, truncation 1 displayed the highest binding and the apparent dissociation constant was determined to be 20.71±3.9 nM.

FIG. 13A, depicts the loop/ring regions of the predicted minimal A2 aptamer (SEQ ID NO:1) with the N regions indicated at each end. FIG. 13B, the loop/ring regions of the predicted structure of Truncation 1 of the A2 aptamer (SEQ ID NO:2) are labelled using letters (e.g., A, B, C, D and E), and the stem (e.g., double-stranded regions) of SEQ ID NO:2 are labelled with numbers (e.g., 1, 2, 3, and 4). FIG. 13B, the loop/ring regions of the predicted structure the original A2 aptamer (SEQ ID NO:3) are labelled using letters (e.g., A, B, C, D, E, F, G, and H), and the stem (e.g., double-stranded regions) of SEQ ID NO:3 are labelled with numbers (e.g., 3, 4, 5, 6 and 7). Stem regions having the same nucleotide sequence in SEQ ID NOs:2 and 3 share the same stem numbering (e.g., stem 3 of SEQ ID NO:2 and SEQ ID NO:3 have the same nucleotide sequence).

DETAILED DESCRIPTION

Figure 1A:
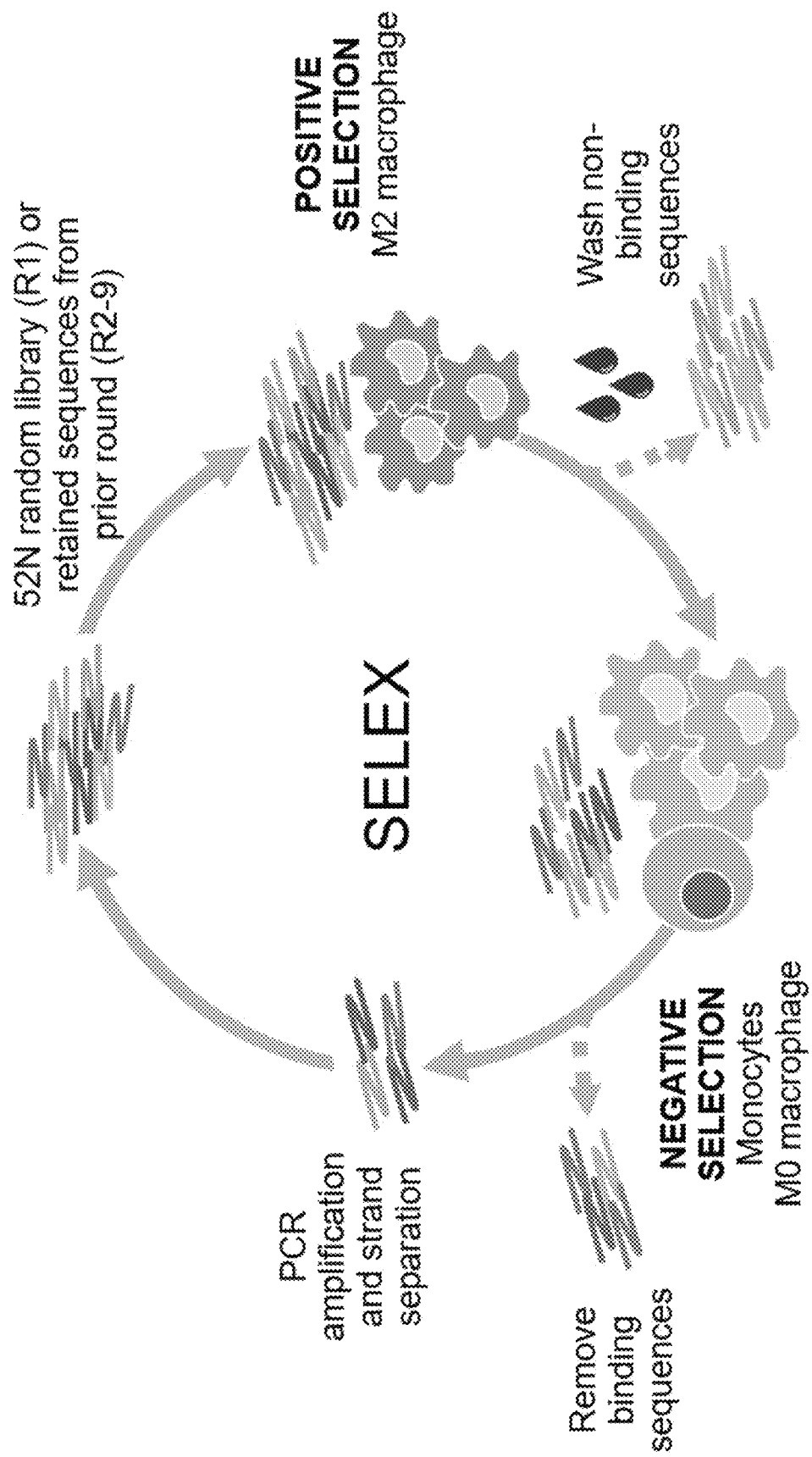

Provided herein are compositions and methods for their use in isolating and/or enriching monocytes and/or macrophages or depleting cell populations of monocytes and/or macrophages. The methods comprise using compositions comprising an aptamer that specifically binds to monocytes and/or macrophages. Further provided are methods of using the aptamers or cell populations generated using them in the methods disclosed herein for therapies and/or drug delivery.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which the methods and compositions belong.

As used herein, the term "macrophages" refers to a type of leukocyte of the monocyte lineage. Macrophages or the monocyte precursors thereof can be readily identified by the expression—or in some instances, absence of expression—of one or more of the following marker proteins: CD14, CD86, HLA-DR, MHC-II, CD80, CD40, CD11b, CD11c, F4/80, CD16, CD64, TLR2, TLR4, CD163, and/or CD274 (see, e.g., Hutchinson et al., *J. Immunol.* 2011; 187(5):2072-2078 and Brem-Exner et al., *J. Immunol.* 2008; 180(1):335-349). CD14 is a specific marker of both monocytes and macrophages and can be used as a sole marker for purification of human monocytes from a peripheral blood sample. Other markers include, without limitation, CD206, CD163, SIRPα, CD11b, CD11c, CD36, CD45, CD9, CD32, CD64, CD14, CD166, and CD131, among others.

As used herein, the term "isolating" a monocyte and/or a macrophage refers to the selective separation or enrichment of a monocyte and/or a macrophage from a sample comprising other cells, cell types or cell classes such that the monocytes and/or macrophage resulting from such separation has a high degree of cell purity as determined by specific cell markers (e.g., CD14 for a monocyte or macrophage).

While higher degrees of cell purity are preferred over lower, cell "isolation" as the term is used herein does not require 100% purity of the resulting cell population. Target cells or a population thereof will generally be considered "isolated" as the term is used herein if they comprise at least 60% monocytes and/or macrophages, and preferably at least 70%, at least 80%, at least 90% or more.

Conversely, as used herein, the term "depleting a monocyte and/or a macrophage" refers to the selective removal of a monocyte and/or a macrophage from a sample comprising other cells, cell types or cell classes such that the resulting cell population lacks or has a reduced number of monocytes and/or macrophages. Target cells or a population thereof will generally be considered "depleted" as the term is used herein if the population includes less than 40% monocytes and/or macrophages resulting from a depletion method as described herein, and preferably includes less than 30%, less than 20%, less than 10%, less than 5%, less than 1% or more. In some embodiments, the cell population following a depletion method as described herein will lack detectable monocytes and/or macrophages (i.e., cells that bind the aptamer). A population of cells is also "depleted" for monocytes or macrophages if the proportion of monocytes or macrophages is reduced following a depletion procedure by at least 50% relative to the proportion of monocytes or macrophages in the starting population. For such a depletion procedure, the population is "depleted" if the resulting population has a proportion of monocytes or macrophages that is reduced by at least 50%, 60%, 70%, 80%, 90%, 95%, 96%, 97%, 98%, 99% or more relative to the starting population.

As used herein, the term "contacting a biological sample," when used in the context of an aptamer or nucleic acid as described herein, refers to addition of an aptamer to a biological sample under conditions that permit specific or selective binding of an aptamer to a target moiety or marker on the cell surface or extracellular matrix of the cell.

As used herein, the term "conditions that permit forming aptamer-bound cells" refers to incubation of cells at 4° C. for 30 minutes in a binding buffer comprising 0.1 mg/mL tRNA, 0.1 g/L $CaCl_2$, 0.2 g/L KCl, 0.2 g/L $KH_2PO_4$, 8.0 g/L NaCl, 2.1716 $Na_2HPO_4$ septahydrate, supplemented with 25 mM glucose, 5.5 mM $MgCl_2$ hexahydrate, varying amounts of bovine serum albumin (BSA) or donor horse serum, with a pH of 7.5, or to conditions that provide binding substantially equivalent to binding permitted under these conditions. In this context, substantially equivalent means±10% of the binding permitted under these conditions.

As used herein, the term "nucleic acid" includes one or more types of: polydeoxyribonucleotides (containing 2-de-oxy-D-ribose), polyribonucleotides (containing D-ribose), and any other type of polynucleotide that is an N-glycoside of a purine or pyrimidine base, or modified purine or pyrimidine bases (including abasic sites). The term "nucleic acid," as used herein, also includes polymers of ribonucleosides or deoxyribonucleosides that are covalently bonded, typically by phosphodiester linkages between subunits, but in some cases by phosphorothioates, methylphosphonates, and the like. "Nucleic acids" include single- and double-stranded DNA, as well as single- and double-stranded RNA. Exemplary nucleic acids include, without limitation, gDNA; hnRNA; mRNA; rRNA, tRNA, micro RNA (miRNA), small interfering RNA (siRNA), small nucleolar RNA (snORNA), small nuclear RNA (snRNA), and small temporal RNA (stRNA), and the like, and any combination thereof.

As described herein, a "compensatory change" refers to a change in a nucleoside or nucleobase pair within an aptamer that maintains predicted secondary structure and/or target binding of the aptamer. Non-limiting examples of compensatory changes include changing a G:C base pair to a C:G base pair or changing an A:T base pair to a T:A base pair, e.g., in a stem-loop structure of a nucleic acid. Because of differences in the hydrogen-bonding characteristics between A:T and C:G base pairs, replacing an A:T base pair with a C:G base pair would be expected to alter the stability of the secondary structure of a double-stranded sequence, i.e., to increase its stability. Thus, a compensatory change described herein can further include such a change. It is contemplated that a change from a C:G or G:C base pair to an A:T or T:A base pair can sometimes be tolerated without significantly affecting the secondary structure or target binding characteristics. However, this type of compensatory change should be considered in the context of the overall stem stability of the aptamer. As described herein, a compensatory change in the nucleotide sequence of an aptamer can involve, where appropriate, a modified nucleoside selected from but not limited to the nucleobases or nucleosides described in Table 1.

As used herein, the term "conjugated to" encompasses association of an aptamer with a solid support, a phase-changing agent, or a member of an affinity pair by covalent bonding, including but not limited to cross-linking via a cross-linking agent, or by a strong non-covalent interaction that is maintained under conditions in which the conjugate is to be used.

As described herein, a "solid support" is a structure upon which an aptamer or plurality of aptamers can be displayed for contact with a target cell. A solid support provides a ready means for isolating or removing bound target cells from a mixture or suspension. A solid support can be in the form, for example, of a particle, bead, filter or sheet, resin, scaffold, matrix, or column. Non-limiting classes of materials that the solid support can comprise include polymer, metal, ceramic, gels, paper, or glass. The materials can include, but are not limited to polystyrene, agarose, gelatin, iron oxide, stainless steel, polycarbonate, polydimethylsiloxane, polyethylene, acrylonitrile butadiene styrene, cyclo-olefin polymers, cyclo-olefin copolymers, and the like.

As described herein, a "phase changing agent" is an agent that is soluble in aqueous solution under one set of conditions, but induced to an insoluble, precipitating form under another set of conditions. The conditions for both soluble and insoluble forms must be compatible with maintaining the viability of target cells. Non-limiting examples of conditions that change phase include temperature, pH and salt or solute concentration. An example of a phase-changing agent includes poly(N-isopropylacrylamide) phase-changing polymers that are soluble at one temperature and then at a different temperature precipitate out from solution.

As used herein, the term "affinity pair" refers to a pair of moieties that specifically bind each other with high affinity, generally in the low micromolar to picomolar range. When one member of an affinity pair is conjugated to a first element and the other member of the pair is conjugated to a second element, the first and second elements will be brought together by the interaction of the members of the affinity pair. Non-limiting examples of affinity pairs that can be conjugated to an aptamer or solid support include ligand-receptor pairs, antibody-antigen pairs, as well as smaller pairs such as biotin-avidin, or biotin-avidin variant, such as biotin streptavidin or biotin-neutravidin, among others. As but one example, the biotin-streptavidin interaction has a $K_d$ of $10^{-14}$ to $10^{-15}$ molar.

As used herein, the term "hybridize" refers to the phenomenon of a single-stranded nucleic acid or region thereof forming hydrogen-bonded base pair interactions with either another single stranded nucleic acid or region thereof (intermolecular hybridization) or with another single-stranded region of the same nucleic acid (intramolecular hybridization). Hybridization between a reversal agent and an aptamer permits the disruption of binding of the aptamer to a target by destabilization of the aptamer's secondary structure, allowing for reversible cell selection to occur. Hybridization is governed by the base sequences involved, with complementary nucleobases forming hydrogen bonds, and the stability of any hybrid being determined by the identity of the base pairs (e.g., G:C base pairs being stronger than A:T base pairs) and the number of contiguous base pairs, with longer stretches of complementary bases forming more stable hybrids.

As used herein, a "magnetoresponsive bead" refers to a solid support particle that can be attracted to a magnetic device or magnetic field. A magnetoresponsive bead coated with or otherwise conjugated to an aptamer can be used to separate aptamer-bound cells from a biological sample.

While the term "bead" infers a spherical form, this is not a limitation of the shape of magnetoresponsive solid support that can be used to separate the aptamer-bound cells from non-aptamer bound cells. The shape can be irregular, or some variation of spherical, oval, cuboid, and the like. In various embodiments, a magnetoresponsive bead can be conjugated to an aptamer covalently, e.g., via a cross-linking reaction, or can be conjugated non-covalently, e.g., via the interaction of members of an affinity pair.

As used herein, a "cell fraction" refers to a subset of cells in a sample population that shares a given characteristic, e.g., expression of a certain marker or set of markers. A targeted cell fraction can include more than one cell type; as but one example, where monocyte cells are a cell fraction, that fraction can include, for example, $CD14^+$ monocytes, among others. In some embodiments, a targeted cell fraction includes a single cell type.

As used herein, the term "specifically binds a monocyte or macrophage" refers to the capacity of an aptamer as described herein to bind to a monocyte or macrophage or cell surface marker thereupon, under conditions that maintain the viability of mammalian cells, such that the aptamer binds the given target cells to a significantly greater degree than it binds to other cells. At a minimum, an aptamer that specifically binds a cell or cell surface marker binds that marker with a $K_d$ of 1 micromolar or less, and binds target marker with at least 100× greater affinity than it binds an unrelated cell or cell surface marker thereof.

The terms "decrease", "reduce", "reduction", or "inhibit" are all used herein to mean a decrease or lessening of a property, level, or other parameter (such as a disease symptom) by a statistically significant amount. In some embodiments, "reduce," "reduction" or "decrease" or "inhibit" typically means a decrease or reduction in the number of target cells (e.g., in a depletion method) by at least 10% as compared to number of target cells in the starting population prior to depletion and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. In other embodiments, "reduce," "reduction" or "decrease" or "inhibit" typically means a decrease in at least one symptom of a given disease by at least 10% as compared to the symptom prior to onset of treatment and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. Rather, the term "complete inhibition" is used to refer to a 100% inhibition as compared to an appropriate reference level. A decrease in a symptom of a given disease can be preferably down to a level accepted as within the range of normal for an individual without the disease.

The terms "increased," "increase" or "enhance" or "activate" are all used herein to generally mean an increase of a property, level, or other parameter (e.g., number of cells bound to aptamer) by a statistically significant amount; for the avoidance of any doubt, the terms "increased", "increase" or "enhance" or "activate" means an increase in the number of target cells in a given population, for example, following a cell enrichment method by at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold, or at least about a 10-fold increase, at least about a 20-fold increase, at least about a 50-fold increase, at least about a 100-fold increase, at least about a 1000-fold increase or more as compared to a reference level.

A "monocyte cell" is a large mononuclear phagocyte of the peripheral blood. Morphologically, monocytes can vary considerably, ranging in size from 10 to 30 µm in diameter and having a nucleus to cytoplasm ratio that ranges from 2:1 to 1:1. The nucleus is often band shaped (horseshoe), or reniform (kidney-shaped). It can fold over on top of itself, thus showing brain-like convolutions and typically no nucleoli are visible. The chromatin pattern is fine and arranged in skein-like strands. The cytoplasm is abundant and appears blue gray with many fine azurophilic granules, giving a ground glass appearance in Giemsa staining. Vacuoles can be present. More preferably, the expression of specific surface antigens is used to determine whether a cell is a monocyte cell. The main phenotypic markers of human monocyte cells include CD11b, CD11c, CD33 and CD115. Generally, human monocyte cells express CD9, CD11b, CD11c, CDw12, CD13, CD15, CDw17, CD31, CD32, CD33, CD35, CD36, CD38, CD43, CD49b, CD49e, CD49f, CD63, CD64, CD65s, CD68, CD84, CD85, CD86, CD87, CD89, CD91, CDw92, CD93, CD98, CD101, CD102, CD111, CD112, CD115, CD116, CD119, CDw121b, CDw123, CD127, CDw128, CDw131, CD147, CD155, CD156a, CD157, CD162, CD163, CD164, CD168, CD171, CD172a, CD180, CD206, CD131a1, CD213a2, CDw210, CD226, CD281, CD282, CD284, CD286 and optionally CD4, CD14, CD16, CD40, CD45RO, CD45RA, CD45RB, CD62L, CD74, CD142 and CD170, CD181, CD182, CD184, CD191, CD192, CD194, CD195, CD197, CX3CR1. Upon contact with sensitive target cells, monocyte cells also produce a number of cytokines, including interferons (IFNs), tumor necrosis factors (TNFs), granulocyte-macrophage colony-stimulating factor (GM-CSF), granulocyte colony-stimulating factor (G-CSF), macrophage colony-stimulating factor (M-CSF), and interleukin 1 (IL-1). In one embodiment, a monocyte as described herein is $CD14^+$ and/or $CD16^+$.

A "macrophage cell" is a cell exhibiting properties of phagocytosis. The morphology of macrophages varies among different tissues and between normal and pathologic states, and not all macrophages can be identified by morphology alone. However, most macrophages are large cells with a round or indented nucleus, a well-developed Golgi apparatus, abundant endocytotic vacuoles, lysosomes, and phagolysosomes, and a plasma membrane covered with ruffles or microvilli. The key functions of macrophages in innate and adaptive immunity are the phagocytosis and subsequent degradation of senescent or apoptotic cells, microbes and neoplastic cells, the secretion of cytokines, chemokines and other soluble mediators, and the presentation of foreign antigens (peptides) on their surface to T lymphocytes. In certain embodiments, a macrophage comprises one or more of the following cell surface markers: CD14, CD16, CD64, CD68, CD71 and/or CCR5.

As used herein, the term "treating" includes reducing or alleviating at least one adverse effect or symptom of a condition, disease, or disorder, for example, a disease or disorder of the immune system (e.g., monocyte and macrophage-mediated disease, such as an autoimmune disease). For example, the term "treating," and "treatment" refers to administering to a subject an effective amount of a composition, e.g., an effective amount of a composition comprising an aptamer or a therapeutic cell composition comprising isolated or enriched monocytes and/or macrophages so that the subject has a reduction in at least one symptom of the disease (e.g., fatigue and the like) or an improvement in the disease, for example, beneficial or desired clinical results. For purposes of this disclosure, beneficial or desired clinical results include, but are not limited to, alleviation of one or more symptoms, diminishment of extent of disease, disease stabilization (e.g., not worsening), delay or slowing of disease progression, amelioration or palliation of the disease state, and remission (whether partial or total), whether detectable or undetectable. In some embodiments, treating can refer to prolonging survival as compared to expected survival if not receiving treatment. Thus, one of skill in the art realizes that a treatment can improve the disease condition but may not be a complete cure for the disease. Successful treatment can also be assessed by a reduction in the need for medical interventions, reduction in hospital or emergency room visits, reduction in fatigue, or other markers of an improved quality of life. In some embodiments, treatment can include prophylaxis. However, in alternative embodiments, treatment does not include prophylaxis.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "pharmaceutically acceptable", "physiologically tolerable" and grammatical variations thereof, as they refer to compositions, carriers, diluents, and reagents, are used interchangeably and represent that the materials are capable of administration to or upon a mammal without the production of undesirable physiological effects such as nausea, dizziness, gastric upset, and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. Therapeutic compositions as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic, and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like. Physiologically tolerable carriers are well known in the art. Exemplary liquid carriers are sterile aqueous solutions that contain no materials in addition to the active ingredients and water or contain a buffer such as sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used with the methods described herein that will be effective in the treatment of a particular disorder or condition will depend on the nature of the disorder or condition and can be determined by standard clinical techniques.

As used herein, the term "subject" includes humans and mammals. The term "mammal" is intended to encompass a singular "mammal" and plural "mammals," and includes, but is not limited to humans; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears. In some preferred embodiments, a mammal is a human. A subject can be of any age including a neonate toddler, child, teen, adult, or a geriatric subject.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" includes one or more methods, and/or steps of the type described herein and/or which will become apparent to those persons skilled in the art upon reading this disclosure and so forth. It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Nucleic Acid Aptamer Compositions

"Aptamers," as that term is used herein is a nucleic acid molecule that comprises both single-stranded (e.g., ring or loop regions) and double-stranded (e.g., stem) regions and having specific binding affinity for a given cell or cell surface marker, e.g., $CD14^+$ macrophage or monocytes, through interactions other than classic Watson-Crick base pairing. Specifically, aptamers can fold into 3-dimensional structures capable of binding specifically to various biosurfaces, such as, for example, cell surface antigens. Aptamers can comprise, for example, DNA, RNA, or modified bases.

Nucleic acid aptamers are an attractive alternative to antibodies for cell selection, cell depletion and drug delivery. Aptamers can possess binding affinities comparable to or even higher than antibodies. Importantly, aptamers are produced synthetically as well-defined, low variability products with long storage stability. Aptamers can be discovered through a library selection method known as systematic evolution of ligands by exponential enrichment (SELEX), and further optimized for chemical stability. With their favorable attributes, the application field for aptamers has escalated in the last quarter century to encompass areas including sensing, purification, diagnostics, drug delivery and therapeutics.

Nucleic acid aptamers include RNA, DNA, and/or synthetic nucleic acid analogs (e.g., PNA) capable of specifically binding target molecules.

Provided herein are methods and compositions relating to nucleic acid aptamers useful for cell selection, target cell depletion or targeted drug delivery. The composition of the nucleic acid aptamer can include but is not limited to the nucleobases described in Table 1 (below) and can comprise one or more combinations of backbone or nucleobase structure characteristic of DNA, RNA, or synthetic nucleic acid analogs such as PNAs or BNAs.

TABLE 1

Nucleosides and Nucleobases

Adenosine (A)
Thymine (T)
Guanosine (G)
5-Methyluridine (U)
Uridine (U)
Cytidine (C)
Deoxyadenosine (dA)
Deoxyguanosine (dG)

TABLE 1-continued

Nucleosides and Nucleobases

Thymidine (dT)
Deoxyuridine (dU)
Deoxycytidine (dC)
Hypoxanthine-adenine (I-A)
Hypoxanthine-cytosine (I-C)
Hypoxanthine-uracil (I-U)
Guanine-uracil (G-U)
N-(2-aminoethyl)-glycine- purine
N-(2-aminoethyl)-glycine- adenosine (PNA-A)
N-(2-aminoethyl)-glycine- guanosine (PNA-G)
N-(2-aminoethyl)-glycine- thymine (PNA-T)
N-(2-aminoethyl)-glycine- uridine (PNA-U)
N-(2-aminoethyl)-glycine- cytidine (PNA-C)
Xanthine
Theobromine
Isoguanine
5-hydroxymethyl cytosine
hypoxanthine.
2-aminoadenine
6-methyl-adenine
6-methyl- guanine
2-propyl-adenine
2-propyl- guanine
2-thiouracil
2-thiothymine
2-thiocytosine
5-halouracil
5-halocytosine
5-propynyl uracil
5-propynyl cytosine
6-azo uracil
6-azo cytosine
6-azo thymine
5-uracil (pseudouracil)
4-thiouracil
8-halo adenine
8-halo guanosine
8-amino adenine
8-amino guanosine
8-thiol adenine
8-thiol guanosine
8-thioalkyl adenine
8-thioalkyl guanosine
8-hydroxyl adenine
8-hydroxyl guanosine
2',4'-BNANC[NBn]
2',4'-BNANC[NMe]
2',4'-BNANC[NH]
2',4'-BNA-1-isoquinolone
2',4'-ENA
2',4'-BNA-2-pridone
3'-amino-2',4'-BNA Aptamers generally consist of relatively short oligonucleotides that typically range from 20 to 80 nucleotides (nt) in length, for example, at least 20 nucleotides, at least 30 nucleotides, at least 40 nucleotides, at least 50 nucleotides, at least 60 nucleotides, at least 70 nucleotides, at least 80 nucleotides or more. An aptamer can be attached to a longer sequence, e.g., at one end or the other of the aptamer, although appended sequences that affect the secondary structure of the aptamer can affect aptamer function. In one embodiment, the aptamer sequence described herein is at least 55 nt, at least 60 nt, at least 65 nt, at least 70 nt, at least 75 nt, at least 80 nt, at least 85 nt, at least 90 nt, at least 95 nt, at least 100 nt, at least 105 nt, at least 110 nt or more. As such, the aptamer can comprise a number (N) of nucleotides (nt) at either the 5' and/or 3' end, wherein each nucleotide is independently selected from adenine, thymine/uracil, guanine, and/or cytosine. N can be present independently at either end, and can be from 3 to 30 nucleotides, optionally from 3 to 20 nucleotides, and preferably 3 to 10 nucleotides. Preferably, the number (N) nucleotides at each end form a stem structure.

The functional activity of an aptamer, i.e., binding to a monocyte and/or a macrophage, involves interactions between moieties or elements in the aptamer with moieties or elements present on the surface of a monocyte and/or macrophage. The interactions can include, for example, hydrophobic/hydrophilic interactions, charge or electrostatic interactions, hydrogen bonding, etc., and the specific interactions of a given aptamer with a given target are determined by the sequence of the aptamer and the secondary and tertiary structure assumed by that sequence under binding conditions. Thus, the occurrence of intramolecular base pairing in the aptamer is a primary factor in aptamer structure and therefore aptamer function. Intramolecular base pairing can result, for example, in double stranded stem structures, stem-loop structures, and exposure of various elements of the aptamer that can participate in binding interactions with a target molecule. Where the secondary structure of an aptamer is defined by its sequence, including the presence of intramolecular base pairs between regions of complementary sequence that fold the molecule into a functional shape, it should be understood that changes in aptamer sequence occurring in a stem structure or that introduce new options for intramolecular base pairing can disrupt the conformation of the molecule and thereby its function. That said, when a change of one nucleotide in a base-paired stem structure is accompanied by a compensatory change in the complementary nucleotide that maintains the ability to base pair, the structure, and thereby the function of the aptamer can be maintained. That is, some aptamers can tolerate some degree of sequence change and still retain binding activity. Furthermore, a truncated or partial sequence of an aptamer as described herein can also retain binding activity provided that the truncation does not alter intramolecular base-pairing necessary for the secondary structure of the aptamer. In particular, it is contemplated that removal of some sequence from the 5' or 3' end of an aptamer described herein can result in an aptamer molecule that retains binding activity. Indeed, some changes can improve binding activity. This, of course, is one basis for an iterative selection approach used to identify aptamers that bind a given target and do so with high affinity.

As described herein, an aptamer can additionally or alternatively comprise nucleobase (often referred to in the art simply as "base") modifications or substitutions. Such substitutions can modify stability of the aptamer or reversal agent, e.g., by reducing susceptibility to enzymatic or chemical degradation, or can modify (increase or decrease) intra- or inter-molecular interactions, including but not limited to base-pairing interactions. Aptamer and reversal agent nucleobases include the purine bases adenine (A) and guanine (G), and the pyrimidine bases thymine (T), cytosine (C), and uracil (U) or modified or related forms thereof. Modified nucleobases include, as non-limiting examples, other synthetic and natural nucleobases, such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine, among others. The base pairing behavior and preferences of these nucleobases are known in the art.

Synthetic nucleotides or oligonucleotides comprised by an aptamer can include but are not limited to peptide nucleic acid (PNA), bridged nucleic acid (BNA), morpholinos, locked nucleic acids (LNA), glycol nucleic acids (GNA), threose nucleic acids (TNA), or any other xeno nucleic acid (XNA) described in the art.

One such oligonucleotide, an oligonucleotide mimetic, that has been shown to have excellent hybridization properties, is referred to as a peptide nucleic acid (PNA). In PNA compounds, the sugar-backbone of an oligonucleotide is replaced with an amide-containing backbone, in particular, an aminoethylglycine backbone can be preferred. The nucleobases are retained and are bound directly or indirectly to atoms of the amide portion of the backbone.

In some embodiments, the aptamers described herein can bind to their target cell (e.g., monocyte and/or macrophage) or cellular antigen with a $K_d$ between $10^{-3}$ to $10^{-7}$ M. For example, in some embodiments, the aptamer can bind a target cell or cellular antigen with a $K_d$ of about $10^{-3}$, $10^{-4}$, $10^{-5}$, $10^{-6}$, $10^{-7}$ M. In other embodiments, the aptamer can bind a target cell or cellular antigen with a $K_d$ of about $10^{-4}$ to $10^{-7}$M. In other embodiments, the aptamer can bind a target cell or cellular antigen with a $K_d$ of about $10^{-5}$ to $10^{-7}$M. In other embodiments, the aptamer can bind a target cell or antigen with a $K_d$ of about $10^{-4}$ to $10^{-6}$M. In other embodiments, the aptamer binds a target cell or antigen with a $K_d$ of about $10^{-6}$ to $10^{-7}$M. In some embodiments, the aptamer binds a target cell or antigen with a $K_d$ of about $10^{-8}$M. In some embodiments, the aptamer binds a target cell or antigen with a $K_d$ of about $10^{-9}$M. In some embodiments, the aptamer binds a target cell or antigen with a $K_d$ of about $10^{-10}$ M.

Nucleic Acid Aptamer Synthesis and Modifications

Aptamers as described herein can be chemically synthesized using, as a non-limiting example, a nucleoside phosphoramidite approach. Furthermore, aptamers can be isolated from a biological sample by DNA or RNA extraction methods. These methods include but are not limited to column purification, ethanol precipitation, phenol-chloroform extraction, or acid guanidinium thiocyanate-phenol chloroform extraction (AGPC).

Following extraction or synthesis, the aptamers described herein can be characterized by liquid chromatography, mass spectrometry, next generation sequencing, polymerase chain reaction (PCR), gel electrophoresis, or any other method of identifying nucleoside sequences, secondary structures, chemical composition, expression, thermodynamics, binding, or function. Aptamers identified by cell-SELEX can further be characterized by aptamer cell binding assays, flow cytometry, or in vivo function as described in the EXAMPLES.

The aptamers described herein can also be modified or conjugated to a solid support or phase-changing agent for cell selection and cell processing. Non-limiting examples of conjugation methods include chemical, thermodynamic, or structural modifications to the aptamer that allows for separation of the aptamer-bound cells from the aptamer unbound cells or biological sample.

In certain embodiments, the aptamers as described herein can be labeled. Non limiting examples of labels can include, for example, fluorophores, and or members of an affinity pair.

Non-limiting examples of affinity pairs that can be conjugated to the aptamer include, for example, biotin: avidin, biotin:streptavidin. biotin:neutravidin (or other variants of avidin that bind biotin).

In one embodiment, the aptamer comprises one of the sequences in Table 2. In one embodiment, the aptamer comprises a sequence comprising at least 65% sequence identity to SEQ ID NO: 1, SEQ ID NO: 2, or SEQ ID NO:3. In other embodiments, the aptamer comprises a sequence comprising at least 65%, at least 70%, at least 75%, at least 80%, at least 85%, at least 90%, or at least 95% sequence identity to SEQ ID NO:1, SEQ ID NO:2, or SEQ ID NO:3. In some embodiments, the aptamer comprises a sequence that differs from SEQ ID NO:1, SEQ ID NO:2, or SEQ ID NO:3 by less than 5 nucleotides, less than 4 nucleotides, less than 3 nucleotides, or less than 2 nucleotides. In other embodiments, the aptamer comprises a sequence that differs from SEQ ID NO:1, SEQ ID NO:2 or SEQ ID NO:3 by 1, 2, 3, 4, 5, 6, 7, or 8 nucleotides. In one embodiment, the aptamer consists essentially of SEQ ID NO:1, 2, or 3. In another embodiment, the aptamer consists of SEQ ID NO:1, 2, or 3. In other embodiments, the aptamer comprises one or more compensatory base changes that maintain double-stranded stem structures as set out herein.

TABLE 2

Aptamer Sequences that Bind Monocytes and/or Macrophages

| Aptamer Sequence | SEQ ID NO: |
|---|---|
| AGCAGAAGAGTAGATGAAACGTTTTTTCGCCCGATAAAAGGGACGT | 1 |
| TTATGACGCAGCAGAAGAGTAGATGAAACGTTTTTTCGCCCGATAAAAGGGACGTGCGTCATAA | 2 |
| ATCCAGAGTGACGCAGCAGAAGAGTAGATGAAACGTTTTTTCGCCCGATAAAAGGGACGTGCGTCAGACA TGGACACGGTGGCTTAGT | 3 |

Figure 13A:
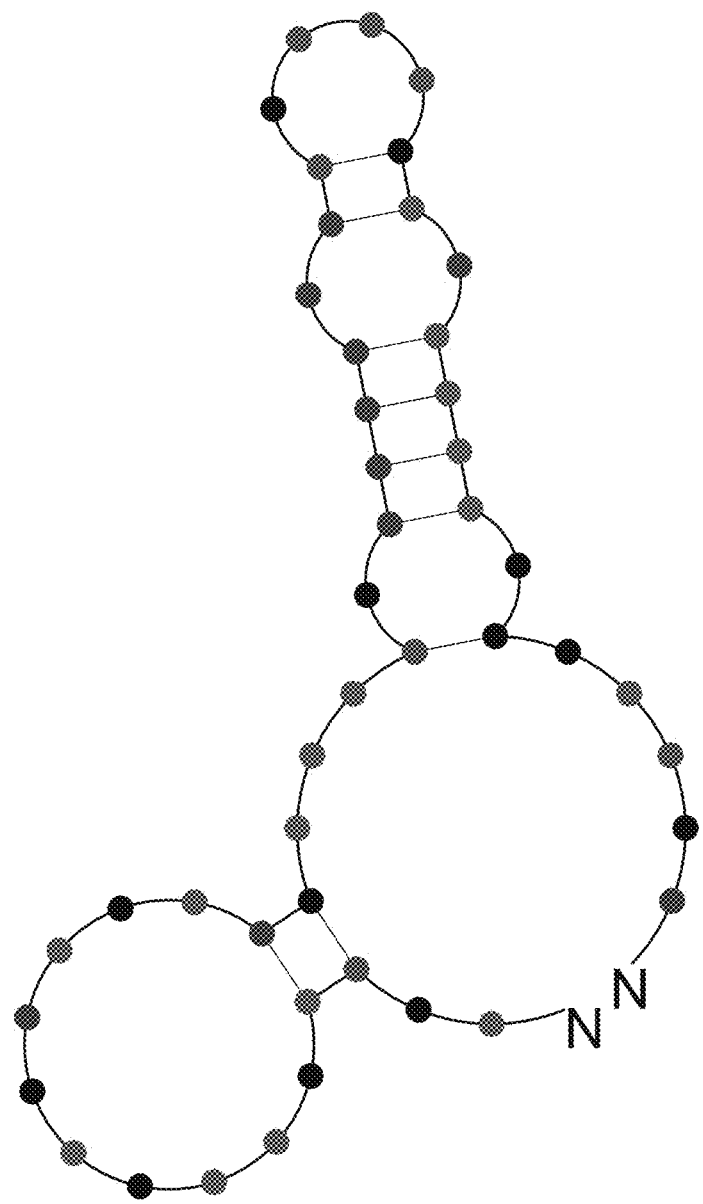
FIGS. 13A-13C Aptamer Structures.
Figure 13B:
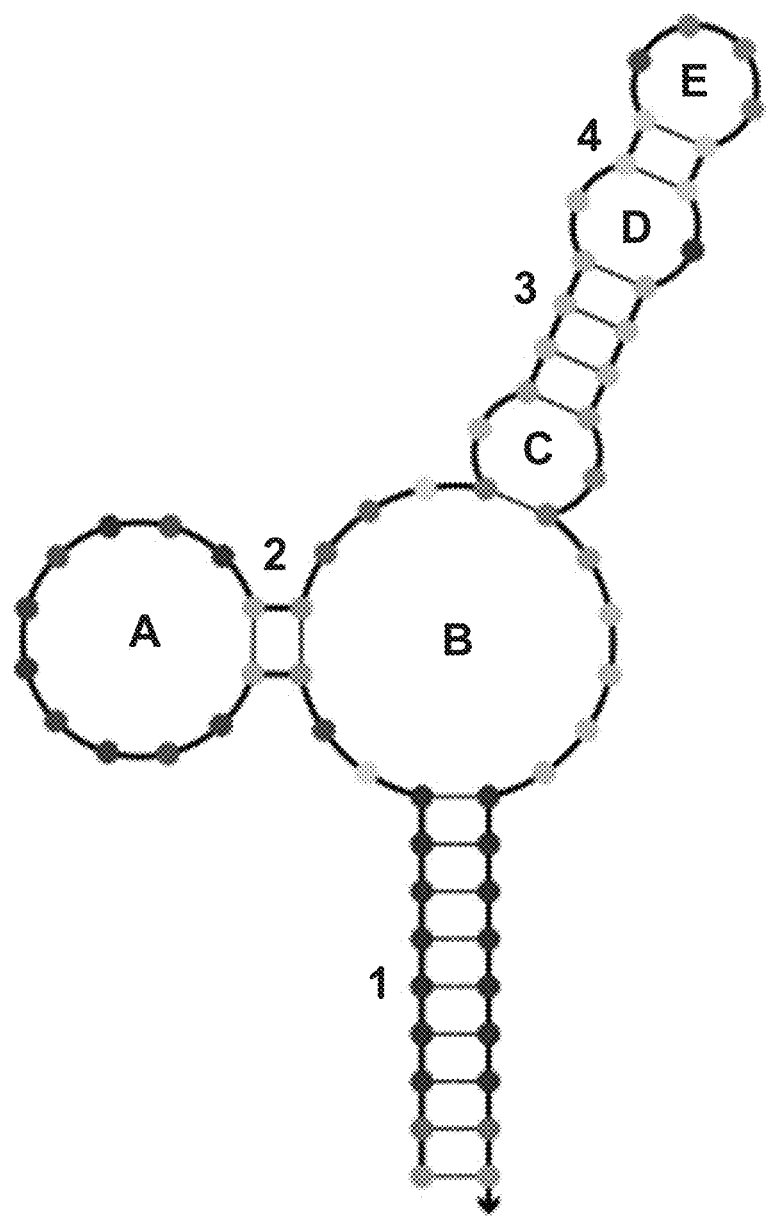
Figure 13C:
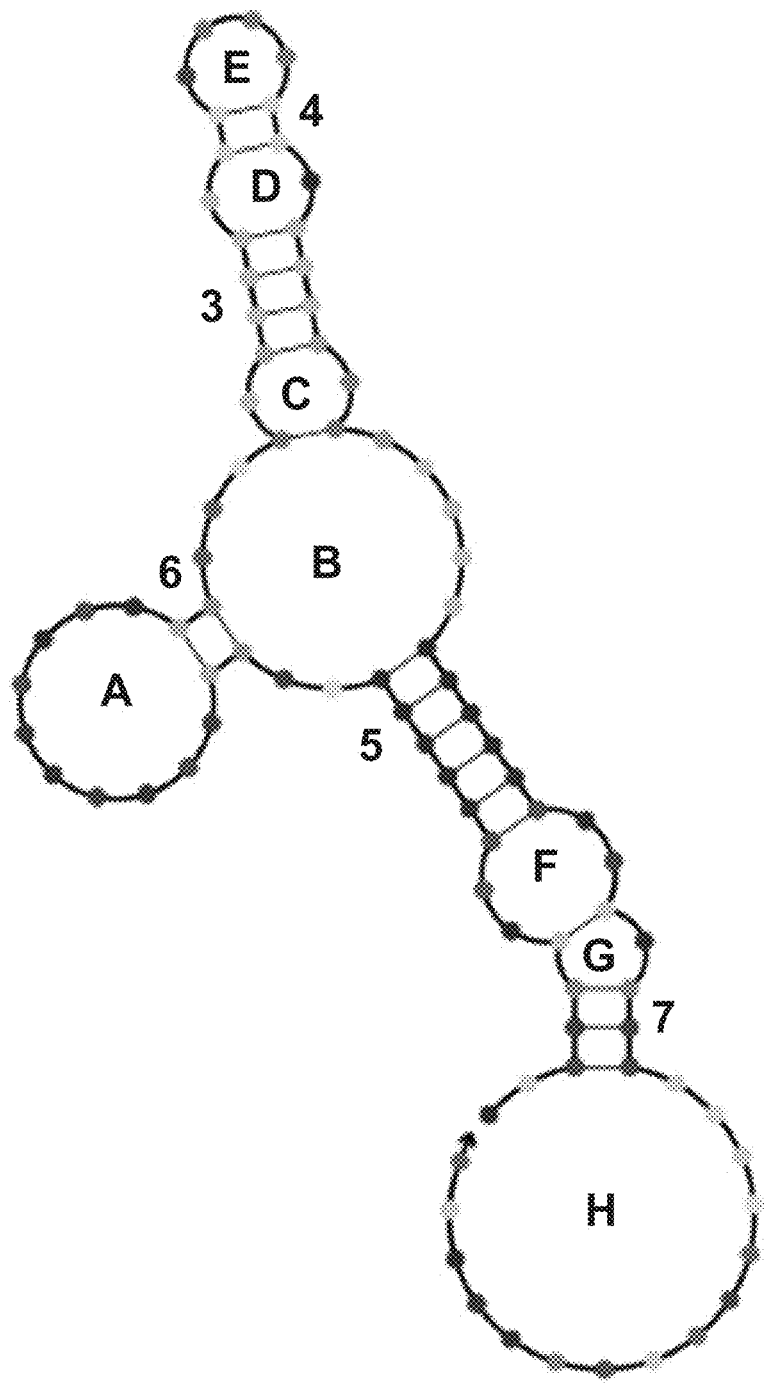

In one embodiment, SEQ ID NO:1 can adopt a secondary structure as depicted in FIG. 13A. In one embodiment, SEQ ID NO:2 can adopt a secondary structure as depicted in FIG. 13B. In one embodiment, SEQ ID NO: 3 can adopt a secondary structure as depicted in FIG. 13C.

In one embodiment, the aptamer that specifically binds a monocyte and/or a macrophage can form a structure that comprises at least 5 loop regions (e.g., A (SEQ ID NO:3), B (SEQ ID NO:4), C, D, and E depicted in FIG. 13A and FIG. 13B), and at least four stem regions (e.g., 1 and 1', 2 and 2', 3 and 3', and 4 and 4' depicted in FIG. 13B). In certain embodiments, the aptamer that specifically binds a monocyte and/or a macrophage can form a structure that comprises at least 6, 7 or 8 loop regions and at least 5 or more stem regions (see e.g., FIG. 13C).

TABLE 3

Ring/Loop sequences

| Ring | Ring Sequence | SEQ ID NO: |
|---|---|---|
| A | AGAAGAGTAGAT | 4 |
| B | CAGCGAAACGGACGTG | 5 |
| C | CGTAGG | |

TABLE 3-continued

Ring/Loop sequences

| Ring | Ring Sequence | SEQ ID NO: |
|---|---|---|
| D | TTTATA | |
| E | CGCCCG | |
| F | GAGTAGAC | |
| G | AGCAT | |
| H | ATCGACACGGTGGCTTAGT | 6 |

In one embodiment, the aptamer described herein can form a structure that comprises at least 5 (e.g., 5, 6, 7, or 8) of the ring sequences in Table 3. A ring sequence as disclosed herein is the sequence of nucleotides that make up the ring and does not take into consideration any loop or stem sequences that may attach to the loop being described. In one embodiment, an aptamer described herein comprises: (i) a sequence that differs by less than 3 nucleotides (e.g., 0, 1, 2, or 3) from the sequence of ring A (SEQ ID NO:4), (ii) a sequence that differs by less than 3 nucleotides from the sequence of ring B (SEQ ID NO:5), (iii) a sequence that differs by less than 3 nucleotides from the sequence of ring C, (iv) a sequence that differs by less than 3 nucleotides from the sequence of ring D, and (v) a sequence that differs by less than 3 nucleotides from the sequence of ring E, and optionally further comprises (vi) a sequence that differs by less than 3 nucleotides from the sequence of ring F, (vii) a sequence that differs by less than 3 nucleotides from the sequence of ring G, and (viii) a sequence that differs by less than 3 nucleotides from the sequence of ring H (SEQ ID NO:6).

TABLE 4

Stem/double-stranded sequences

| Stem | Sequence |
|---|---|
| 1 | TTATGACGC |
| 1' | AATACTGCG |
| 2 | GA |
| 2' | CT |
| 3 | TTTT |
| 3' | AAAA |
| 4 | TC |
| 4' | AG |
| 5 | TGACGC |
| 5' | ACTGCG |
| 6 | CA |
| 6' | GT |
| 7 | CCA |
| 7' | GGT | n' sequences are reverse and complement of n sequence (e.g., stem 1') is reverse and complement of stem 1)

In one embodiment, the aptamer can form a structure that comprises at least four (e.g., 4, 5, 6, or 7) double-stranded stem regions recited in Table 4. As will be appreciated by those of skill in the art, nucleotide substitutions in one or more of the stem regions can be introduced, however a compensatory nucleotide change must also be made in the corresponding complementary strand to maintain double-strandedness in the stem region. For example, if a T is substituted for a G, the complementary strand should have the corresponding A substituted for the corresponding C. In one embodiment, the aptamer can form a structure that comprises at least four double-stranded regions comprising (i) a sequence that differs by less than 3 nucleotides (e.g., 0, 1, 2, or 3) from Stem 1 and a complementary strand thereof, (ii) a sequence that differs by less than 3 nucleotides from Stem 2 and a complementary strand thereof, (iii) a sequence that differs by less than 3 nucleotides from Stem 3 and a complementary strand thereof, and (iv) a sequence that differs by less than 3 nucleotides from Stem 4 and a complementary strand thereof, and optionally (v) a sequence that differs by less than 3 nucleotides from Stem 5 and a complementary strand thereof, (vii) a sequence that differs by less than 3 nucleotides from Stem 6 and a complementary strand thereof, and (viii) a sequence that differs by less than 3 nucleotides from Stem 7 and a complementary strand thereof.

Solid Supports

In certain embodiments, aptamers are bound directly or indirectly to a solid support. Aptamer-bound solid supports described herein can exist in the form of a platform, column, filter or sheet, dish, a microfluidic capture device, capillary tube, electrochemical responsive platform, scaffold, cartridge, resin, matrix, bead, nano-bead or -particle, or another solid support known in the art.

In some embodiments, the solid support comprises materials that include, but are not limited to, a polymer, metal, ceramic, gels, paper, or glass. The materials of the solid support can further comprise, as non-limiting examples, polystyrene, agarose, gelatin, alginate, iron oxide, stainless steel, gold nanobeads or particles, copper, silver chloride, polycarbonate, polydimethylsiloxane, polyethylene, acrylonitrile butadiene styrene, cyclo-olefin polymers or cyclo-olefin copolymers, Sepharose™ resin, and the like.

The aptamer-bound solid support can further comprise a magnetoresponsive element such as a magnetoresponsive bead. In some embodiments, the magnetoresponsive element or bead is in the form of a sphere, cube, rectangle, cylinder, cone, or any other shape described in the art. Aptamer bound to magnetoresponsive beads provides a simple method of separating aptamer-bound cells from non-bound cells by permitting a suspension of the cells to interact with the aptamer-conjugated beads, and then subjecting the sample to a magnetic field. The beads, with aptamer-bound cells, are attracted to the magnetic source, permitting the removal of non-bound cells, e.g., via pipette. Beads with bound cells can be washed and subjected to the magnetic field again to increase the relative purity of the isolated cell fraction.

In some embodiments, the magnetoresponsive element comprises magnetite, iron (III) oxide, samarium-cobalt, terfenol-D, or any other magnetic element described in the art.

In some embodiments the solid support is in contact with an extracellular matrix protein or composition. Non-limiting examples include fibronectin, collagen, laminin, poly-L-lysine, Matrigel™, vitronectin, tenascin, fibrillin, brevican, elastin, or other extracellular matrix protein or composition known in the art.

The solid support bound to the aptamer can also contain a label. In some embodiments, the label is conjugated to the aptamer. In some embodiments, the label is a heterologous protein. In some embodiments, the heterologous protein is a tag, such as a fluorescent protein. Such proteins can facilitate tracking and/or visualization of the aptamers. Examples of fluorescent proteins include, but are not limited to, green fluorescent protein (GFP) from the jellyfish *Aequorea victoria*; mutant versions of GFP that fluoresce different colors (such as BFP, blue fluorescent protein; YFP, yellow fluorescent protein; and CFP, cyan fluorescent protein); dsRed fluorescent protein (dsRed2FP); eqFP611, a red fluorescent protein isolated from *Entacmaea quadricolor*; AmCyan1, a cyan fluorescent protein isolated from *Anemonia majano*, and originally named amFP486; Azami Green, a bright fluorescent protein isolated from Galaxeidae; ZSGREEN™, a fluorescent protein isolated from Zoanthus; or any other fluorescent protein or element described in the art.

In some embodiments the aptamers are labeled with a fluorophore. Non-limiting examples of fluorophores include fluorescein, rhodamine, Oregon green, eosin, Texas red, cyanins, e.g., Cy5.5, among others.

In one embodiment, the aptamer can further comprise a "tag," which refers to a component that provides a means for attaching or immobilizing an aptamer (and any target molecule that is bound to it) to a solid support, such as a bead, e.g., an agarose bead. A "tag" is a set of copies of one type or species of component that is capable of associating with a probe. "Tags" refers to more than one such set of components. The tag can be attached to or included in the aptamer by any method known in the art. Generally, the tag allows the aptamer to associate, either directly or indirectly, with a probe that is attached to the solid support, e.g., a bead. A tag can enable the localization of an aptamer covalent complex to a spatially defined address on a solid support.

Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX™ is used to identify an aptamer, the tag may be added to the aptamer either pre- or post-SELEX™. In one embodiment, the tag is included on the 5'-end of the aptamer post-SELEX™. In another embodiment, the tag is included on the 3'-end of the aptamer post-SELEX™. In one embodiment, the tag is a biotin molecule. In another embodiment, the tag is a streptavidin molecule.

In another embodiment, an aptamer is attached to a solid support through interactions between the tag and a probe on the beads. A "probe" is a set of copies of one type or species of component that is capable of associating with a tag. "Probes" refers to more than one such set of components. The probe can be attached to or included in the solid support, such as, for example, a bead by any method known in the art. Generally, the probe allows the solid support, e.g., the bead to associate, either directly or indirectly, with a tag that is attached to the aptamer. A probe can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a probe can be designed or configured to bind or otherwise associate with specificity with a tag. In one embodiment, the probe is a streptavidin molecule, for example, the streptavidin moiety binds to the biotin groups on the aptamer, thereby localizing the aptamers on the solid support to which the streptavidin-coupled beads are bound. In another embodiment, the probe is a biotin molecule.

In one embodiment, the aptamers and solid supports as described herein can be used in a device for enriching a cell population of monocytes and/or macrophages or alternatively, depleting a cell population of such monocytes and/or macrophages. The device can optionally comprise a column containing, e.g., beads and the filter. In some embodiments, the column is fitted with a syringe. In some embodiments, the column can be sized to fit in a centrifuge tube. In some embodiments the device further comprises a centrifuge tube housing the column.

In some embodiments, beads with attached aptamer are packed in a column. In other embodiments, beads with attached aptamer are present in a suspension and collected by centrifugation. The column containing the beads can be of a size and character to allow release of cells without removal of beads. In some embodiments, the column can be of a volume of about 1 mL, 2 mL, 3 mL, 4 mL, 5 mL, 6 mL, 7 mL, 8 mL, 9 mL, 10 mL, 15 mL, 20 mL, 30 mL, 40 mL, 50 mL, 60 mL, 70 mL, 80 mL, 90 mL, 100 mL, 500 mL, 1000 mL, and the like. To facilitate removal of cells from beads, the column can be sized to fit in a centrifuge tube, for example, a small Eppendorf™ tube or a large Falcon™ tube, such that cells can be collected by centrifugation using either a tabletop centrifuge or a large centrifuge. When beads are packed in a column, the column can contain a filter with pores sized to allow cells to pass through while retaining beads in the column. In one embodiment, the filter has a pore size smaller than the diameter of the beads. In another embodiment, the filter has a pore size larger than the diameter of the cells to be enriched. In some embodiments, the filter has a pore size of, for example, about 10-100 µm, e.g., about 10 µm, 20 µm, 30 µm, 40 µm, 50 µm, 60 µm, 70 µm, 80 µm, 90 µm, or 100 µm. In other embodiments, the filter has a pore size of about 10-50 µm, about 10-30 µm, about 10-25 µm, about 10-20 µm, or about 10-15 µm. In some embodiments, the filter has a pore size of less than 10 µm.

The size of beads to which the aptamer is attached can vary. In some embodiments, the beads have a diameter of about 30-200 µm.

In some embodiments, the beads are separated from the captured monocytes and/or macrophages by applying mechanical forces, without the addition of any other reagents. As a result, the isolated cell population is free or substantially free of beads, aptamer, antibody, or any other undesired reagents. In some embodiments, mechanical forces can be applied to the beads without removing them from the column. Release of captured monocytes and/or macrophages can be accomplished by, for example, resuspension in a buffer, shaking, pipetting, or by vortex mixing the aptamer-coupled beads. In other embodiments, the column is fitted with a syringe. The syringe can be used to mechanically agitate the beads/cells, thereby disrupting the interaction between beads and cells. The use of mechanical force to separate cells from the aptamer coated beads allows the bound cells to be released without adding any extraneous reagents that could subsequently contaminate the cell population and limit the use of the cell population in clinical applications.

In other embodiments, captured cells can be released from the device using a change in temperature. For example, the beads can be exposed to elevated temperatures for a minimal amount of time sufficient to denature the nucleic acid aptamer and release the cells, without significantly impacting cell viability. In other embodiments, captured cells can be released from the device using a nucleic acid molecule complementary to all or a part of the nucleic acid aptamer (also referred to herein as a "release agent"). Such release agents can compete for binding to the aptamer with cells containing the antigen, causing release of cells when the aptamer binds to the complementary nucleic acid. Temperature and/or complementary nucleic acid can be used to release cells from the aptamer independently or in conjunction with mechanical disruption, as described herein.

In alternative embodiments, a phase-changing agent can be used in place of a solid support. Phase change agents can change phase or precipitate under a given set of conditions and can thereby facilitate the separation of aptamer-bound from aptamer-unbound cells. In some embodiments, a phase-changing agent can be bound to the aptamer. For example, the phase-changing agent can be soluble in aqueous solution under one set of conditions, but induced to an insoluble, precipitating form under another set of conditions. Further exemplary conditions that can induce a phase change include temperature, pH, salt or solute concentration, light (e.g., ultraviolet or fluorescent), or mechanical forces. For example, poly(N-isopropylacrylamide) is a phase-changing polymer that is soluble at, for example, one temperature and, then at a different temperature, precipitates out from solution. Upon induction of precipitation, cells bound to the aptamer will be pulled into the precipitated phase. It is also contemplated that a phase changing agent can act in a similar manner to riboflavin that is activated by ultraviolet light.

Characterization of Aptamer Cell Binding

Nucleic acid aptamers identified by the cell-SELEX method described herein, or by another method as known in the art can be characterized by a number of approaches including but not limited to aptamer binding assays, next generation sequencing, gene profiling, functional assays such as cytotoxicity assays, cytokine release assays, and in vivo delivery of, for example, native or modified cells isolated through use of the aptamers to an animal or human model. The above methods can serve as quality control of the compositions and method of cell selection described herein.

To characterize aptamer binding to target cells or cells of interest, an in vitro binding assay can be performed, for example, as follows. A population comprising, e.g., $2 \times 10^5$ or more cells of interest (e.g., monocytes) is incubated with folded FAM-labeled ssDNA pools or FAM/biotin-labeled individual aptamers for 30 minutes at 4° C. in binding buffer as described herein, and at various concentrations of aptamer.

In some embodiments, the aptamers are labeled with biotin, avidin, streptavidin, agarose, or neutravidin.

Following incubation, e.g., in a total volume of 100 µL, cells are washed twice in, e.g., 200 µL of wash buffer supplemented with 1% (weight/volume) BSA to remove excess aptamer. If the aptamers used were biotinylated, cells can undergo a second incubation with 100 µL fluorescently labeled streptavidin or neutravidin secondary label for 20 min at 4° C. in wash buffer with 1% BSA before again washing twice. Stained cells can be fixed, e.g., in 200 µL wash buffer with 1% BSA (weight/volume) and 0.1% (weight/volume) paraformaldehyde (PFA) before analyzing via flow cytometry.

At a minimum, an aptamer that specifically binds a given target cell or cell surface marker binds a cell expressing that marker with at least 100× greater affinity than the binding of the aptamer to a cell that does not express that marker, and preferably with at least 200× greater affinity, at least 300× greater affinity, at least 500× greater affinity, at least 600× greater affinity, at least 700× greater affinity, at least 800× greater affinity, at least 900× greater affinity, at least 1,000× greater affinity or more.

Affinity can be expressed in terms of dissociation constant, or $K_d$. An aptamer that selectively binds a cell surface marker will generally bind with a $K_d$ below 1 micromolar (1 µM). Aptamers have been described that bind their targets with $K_d$s in the picomolar (pM) range. However, aptamers useful for cell selection can bind in the range of 1 µM to 10 pM, 1 µM to 100 pM, 1 µM to 200 pM, 1 µM to 300 pM, 1 µM to 400 pM, 1 µM to 500 pM, 1 µM to 600 pM, 1 µM to 700 pM, 1 µM to 800 pM, 1 µM to 900 pM, 1 µM to 1 nM, 1 µM to 10 nM, 1 µM to 50 nM, 1 µM to 100 nM, 1 µM to 150 nM 1 µM to 200 nM, 1 µM to 250 nM, 1 µM to 300 nM, 1 µM to 350 nM, 1 µM to 400 nM, 1 µM to 450 nM, 1 µM to 500 nM, 1 M to 550 nM, 1 µM to 600 nM, 1 µM to 650 nM, 1 µM to 700 nM, 1 µM to 750 nM, 1 µM to 800 nM, 1 µM to 850 nM, 1 µM to 900 nM, 1 µM to 950 nM, less than 500 nM to 10 pM, less than 450 nM to 10 pM, less than 400 nM to 10 pM, less than 350 nM to 10 pM, less than 300 nM to 10 pM, less than 250 nM to 10 pM, less than 200 nM to 10 pM, less than 150 nM to 10 pM, less than 100 nM to 10 pM, less than 50 nM to 10 pM, less than 100 nM to 900 pM, less than 100 nM to 800 pM, less than 100 nM to 700 M, less than 100 nM to 600 pM, less than 100 nM to 500 pM, less than 100 nM to 400 pM, less than 100 nM to 300 pM, less than 100 nM to 200 pM, less than 100 nM to 100 pM, less than 100 nM to 50 pM, or less than 100 nM to 10 pM. Various methods are known in the art for determining $K_d$ for an aptamer's binding to its target. Jing & Bowser, *Anal. Chim. Acta* 686: 9-18, which is incorporated herein by reference, reviews various approaches.

In one embodiment, the aptamer can be assessed for the binding of CD14$^+$ monocytes and/or macrophages using flow cytometry of cells and gating for CD14$^+$ cells.

Cell Selection Quality Control and Traceless Cell Selection Methods Using Aptamers Flow cytometry analysis along with other methods for cellular identification can be used to evaluate aptamer/cell interactions and the ability to select target cells using a given aptamer or combination of aptamers. OneComp™ eBeads (Invitrogen) can be used to prepare single-color controls for compensation, if needed. Stained biological samples can be analyzed, for example, using a MACSQuant™ Analyzer 10 (Miltenyi), Attune™ NxT (Invitrogen), or BD LSR-Fortessa™ (BD Biosciences) flow cytometer.

Cell selection methods using aptamers are described herein. In one approach, for each biological sample (e.g. PBMCs), two 100 microliter (µL) aliquots of anti-biotin magnetoresponsive microbeads (Miltenyi) are each diluted to 500 microliters (µL) in binding buffer with 5 nM aptamer specific for the cell or cell marker, e.g., CD14 or CD8, and incubated for 15 min at 4° C. under gentle rotation.

In some embodiments, the microbead can be substituted by another solid support, e.g., as described herein.

In some embodiments, the amount of aptamer incubated with cells for cell selection is 1 picomole (pM) or more, 1 nanomole (nM) or more, 1 micromole (µM) or more.

The presence of tRNA or another non-specific nucleic acid in the binding buffer can be useful during the cell selection step, as the tRNA or other non-specific nucleic acid can help to block non-specific binding of the aptamer or, when present, an oligonucleotide reversal agent.

In some embodiments, then, the binding buffer can comprise, for example, 0.1 mg/mL tRNA, 0.1 g/L CaCl$_2$, 0.2 g/L KCl, 0.2 g/L KH$_2$PO$_4$, 8.0 g/L NaCl, 2.1716 Na$_2$HPO$_4$ septahydrate, supplemented with 25 mM glucose, 5.5 mM MgCl$_2$ hexahydrate, varying amounts of bovine serum albumin (BSA) or donor horse serum (DHS), with a pH of 7.5.

For cell selection, aptamer-labeled or conjugated bead suspensions are added, for example, to 1×10$^8$ freshly isolated cells (e.g., PBMCs), and allowed to incubate for 15 min at 4° C. under gentle rotation. The length of incubation time, temperature, and number of cells can be varied by the ordinarily skilled artisan. While various parameters such as temperature, ionic strength, etc. can affect aptamer binding properties, it should be kept in mind that the aptamers must bind under conditions that maintain cell viability. The temperature, ionic strength, etc. should only be varied in the ranges tolerated by viable cells or cells that can be thawed and become viable following cell selection.

In some embodiments, the biological sample can comprise whole blood, buffy coat, or isolated mononuclear cells.

Magnetic separation can be performed using, e.g., the Miltenyi MACS cell separation system (e.g., QUADROMACS™). Bound cells are washed with 10 milliliters (mL) autoMACS buffer with 0.5% (weight/volume) BSA to remove excess beads, resuspended in autoMACS buffer with 0.5% (weight/volume) BSA, and applied to LS Columns on a magnetic separator per the manufacturer's instructions.

A flow through (FT) fraction can be isolated that includes the flow through from the initial application of cells and, e.g., three subsequent 3 mL column washes.

A 5 milliliter (mL) column flush (CF) can be used to remove CD8 Microbead-labeled cells from the column when removed from the magnet. 1 mL of 500 nanomolar (nM) reversal agent (100-fold excess) in autoMACS buffer with 0.5% (weight/volume) BSA and 5 millimolar (mM) magnesium chloride (MgCl$_2$) can be applied to the column on the magnet, such that aptamer-bound cells captured by the magnet are released into suspension from the aptamer-functionalized beads.

The concentration of reversal agent can vary, depending upon the nature of the agent (e.g., small molecule vs. oligonucleotide) and its binding kinetics with the aptamer. In some embodiments, approximately 600-700 microliters (µL) of the reversal agent solution can be passed through the column before it is plugged with a M/F Luer Lock Plug (Smiths Medical) for a 10-minute incubation at room temperature or any conditions that permit the use of a functional reversal agent. Upon removal of the plug, the column can be washed three times with 3 milliliters (mL) autoMACS buffer with 0.5% (weight/volume) BSA and 5 millimolar (mM) ethylenediaminetetraacetic acid (EDTA), which constitutes the reversal agent elution (RAE) fraction.

The reversal agent eluted cells can be immediately spun down and re-suspended in fresh buffer to remove any remaining reversal agent. Remaining cells on the column can be removed with a column flush as described herein.

Uses for Cells Selected (or Depleted) on the Basis of Aptamer Binding

Large scale preparation or manufacturing of specific cell types is becoming increasingly useful for cellular-based therapies. The methods and compositions described herein provide an efficient approach for the isolation of specific target cell types (e.g., monocytes and/or macrophages) that is readily scaled up for the large-scale isolation of cells for these and other uses. Alternatively, the methods and compositions described herein can be used to deplete unwanted target cells (e.g., monocytes and/or macrophages) from a given cell population prior to treatment of a subject with a therapeutic cell composition.

In some embodiments, cells selected as described herein can be used in their natural form for therapeutic treatment of diseases or to relieve symptoms of disease. In other embodiments, cell populations in which the target cells that bind the aptamers described herein are depleted can be used in their natural form for the therapeutic treatment of a given disease and/or symptom thereof. Thus, the aptamer selected cells (or a cell population that is depleted of aptamer-binding target cells) can be useful in treating animals, including mammals, including humans for a disease or disorder treatable with such cells. In other embodiments, the cells are manipulated and/or expanded prior to introduction to a patient. The cells can be autologous to the patient, allogeneic, or even xenogeneic. Manipulations can include, as non-limiting examples, further cell sorting, stimulation with antigen, induction of differentiation, and/or genetic modification. Manipulated cells can be but are not necessarily expanded prior to administration.

In some embodiments, the aptamers and methods described herein can be used for depleting monocytes and/or macrophages from blood products. For example, the aptamers provided can be used to deplete monocytes from patient leukapheresis for downstream processing, and which can then yield CAR T products that outperform those manufactured in the presence of monocytes (e.g., improved T cell activation and transduction efficiency; see e.g., Noaks et al. *Mol Ther. Methods Clin. Dev.* (2021) 20:675-687; Stroncek et al. *J. Transl. Med.* (2017) 15:59).

In one embodiment, the aptamers described herein are immobilized on a solid support and are used to reduce monocyte populations in a leukopheresis product. By depletion of monocytes, it is meant that at least about 50%, about 60%, about 65%, about 70%, about 75%, about 80%, about 85%, about 90%, about 95% or more of the original monocyte population is removed.

Monocyte and Macrophage Therapeutic Compositions

The aptamers provided herein selectively bind macrophages and monocytes, permitting such cells to be isolated or enriched from a heterogeneous population of cells. As used herein, the term "macrophages" refers to a type of leukocyte of the monocyte lineage. Macrophages or the monocyte precursors thereof can be readily identified by the expression—or in some instances, absence of expression—of one or more of the following marker proteins: CD14, CD86, HLA-DR, MHC-II, CD80, CD40, CD11b, CD11c, F4/80, CD16, CD64, TLR2, TLR4, CD163, and/or CD274 (see, e.g., Hutchinson et al., *J. Immunol.* (2011) 187(5):2072-8 and Brem-Exner et al., *J. Immunol.* (2008) 180(1):335-349). CD14 is a specific marker of both monocytes and macrophages and can be used as a sole marker for purification of human monocytes from a peripheral blood sample. Other markers include, without limitation, CD206, CD163, SIRPα, CD11b, CD11c, CD36, CD45, CD9, CD32, CD64, CD14, CD166, and CD131, among others.

In one embodiment, the aptamers described herein bind to $CD14^+$ macrophage. In other embodiments, the aptamers described herein do not bind to $CD16^+$ macrophage.

In some embodiments, the aptamers described herein can be used to enrich monocytes or macrophages in a cell population. By an enriched cell composition of macrophages or monocytes, it is meant that at least about 50%, about 60%, about 70%, about 80%, about 90%, about 95% or more of the cells of the cell composition are macrophages or monocytes. In some instances, the enriched composition will be a substantially pure population of macrophages or monocytes, whereby "substantially pure" it is meant at least 90% or more of the composition will be of the selected phenotype, e.g., 95%, 98%, and up to 100% of the population.

The monocytes and macrophages isolated or enriched using the aptamers described herein can be used in the treatment of a disease including, but not limited to, cancer, acute or acquired immuno-deficiencies, chronic or acute injury, wounds, degenerative diseases, autoimmune diseases, chronic inflammatory diseases, atherosclerosis, poly- and osteo-arthritis, osteoporosis, infectious diseases (e.g., infections by virus, or bacteria), and metabolic diseases.

Immunodeficiencies include those diseases or disorders that are acquired or genetic in origin, as well as those that result from exposure to radiotherapy/chemotherapy. In one embodiment, the use of macrophages and monocytes enriched using the aptamers described herein in the treatment of acquired immunodeficiency syndrome (AIDS) is particularly contemplated.

Patients on chemotherapy with anticancer agents such as cyclophosphamide (CP) experience a strong reduction in the size of tissue macrophage populations that accompanies blood leukopenia. These patients are thus especially susceptible to opportunistic infections, including gram-negative bacterial pneumonia. Such opportunistic infections are a common cause of death in cancer patients who are undergoing chemotherapy (Santosuosso M, et al. (2002) *Blood* 99(4):1246-1252). Therefore, in some embodiments, methods for isolating or enriching macrophages or monocytes as described herein can be used for the treatment of subjects who have undergone a chemotherapy.

Macrophages enriched or isolated as described herein can also be used as stromal support for efficient cellular engraftment and tissue repair. Therefore, aptamer-selected or aptamer-enriched macrophages and monocytes as described herein can be used for the treatment of bone or muscle lesions (e.g., bone or muscular lesion such as those resulting from a disease or an injury). Non-limiting examples of bone or muscle lesions include, but are not limited to, a bone fracture, a torn muscle, a cardiac lesion, a cardiac injury, myocardial infarction, heart insufficiency, coronary thrombosis, dilated cardiomyopathy, or any cardiomyocyte dysfunction subsequent to, or resulting from, any genetic defect.

Macrophages or monocytes that are enriched or isolated using the aptamers described herein can also be used for the treatment of spinal cord injury.

In addition, isolated or enriched macrophages prepared using the aptamers described herein can be used for enhancing wound healing and/or repairing tissue damage.

Such macrophage compositions can also be genetically modified, pharmacologically treated or alternatively activated or stimulated by bio-active molecules such as cytokines or growth factors to present a desirable phenotype before introduction into a subject to compete with and supplant macrophages with undesired activity.

In addition, monocytes and macrophages prepared as described herein can be used in the treatment of cancer including, but not limited to, carcinomas of breast, colon, rectum, lung, oropharynx, hypopharynx, esophagus, stomach, pancreas, liver, gallbladder and bile ducts, small intestine, kidney, bladder, urothelium, female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, such as astrocytomas, gliomas, glioblastomas, retinoblastomas, neuromas, neuroblastomas, Schwannomas, and meningiomas, and tumors arising from hematopoietic malignancies such as leukemias as well both Hodgkin's and non-Hodgkin's lymphomas. Exemplary hematological cancers that can be treated with macrophages and monocytes as described herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia Further, the monocytes and/or macrophages can be administered to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the monocytes and/or macrophages can be used for the treatment of any condition in which a diminished or otherwise inhibited immune response, especially a cell-mediated immune response, is desirable to treat or alleviate the disease (e.g., autoimmune disease). Examples of autoimmune disease include, but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The monocytes and macrophages can also be used to treat inflammatory disorders. Examples of inflammatory disorders include, but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

In certain embodiments, the monocytes and macrophages isolated or enriched as described herein can be expanded, differentiated in vitro, or engineered as desired before administration as a therapeutic cell composition.

In one embodiment, monocytes and macrophages for use as therapeutics are obtained directly from the subject to whom they are administered (i.e., autologous transplantation). In another embodiment, the transplantation can be non-autologous or allogeneic. As used herein, "allogeneic" refers to macrophages or monocytes obtained from one or more different donors of the same species, where the genes at one or more loci are not identical. For example, a therapeutic macrophage or monocyte composition being administered to a subject can be derived from umbilical cord blood obtained from one more unrelated donor subjects, or from one or more non-identical siblings. In some embodiments, syngeneic macrophage or monocyte cell populations can be used, such as those obtained from genetically identical animals, or from identical twins. In other embodiments of this aspect, the therapeutic cells are autologous cells; that is, the macrophages and monocyte cells are obtained or isolated from a subject and administered to the same subject, i.e., the donor and recipient are the same.

For non-autologous transplantation, the recipient is preferably given an immunosuppressive drug to reduce the risk of rejection of the transplanted cell. Methods of administering cells include but are not limited to intradermal, intramuscular, intraperitoneal, intravenous, subcutaneous, intranasal, and epidural routes. The cells can be administered by any convenient route and can be administered together with other biologically active agents. The route of administration is preferably intravenous or intradermal. The titer of monocytes and/or macrophages transplanted or administered which will be effective in the treatment of a particular disease or condition will depend on the nature of the disorder or condition and can be determined by standard clinical techniques. In addition, in vitro assays can optionally be employed to help identify optimal dosage ranges. The precise dose to be employed in the formulation will also depend on the route of administration, and the seriousness of the disease or disorder, and should be decided according to the judgment of the practitioner and each subject's circumstances.

In some respects, the methods provided herein comprise delivering a plurality of aptamer-selected cells or their progeny or differentiation product cells to a host tissue. In other aspects, the methods provided herein comprise delivering a plurality of cells that have been depleted of aptamer-binding cells (e.g., monocytes and/or macrophages). As described herein, cells isolated or selected by aptamers according to the methods described herein can be incorporated into pharmaceutical compositions suitable for administration to a subject, e.g., for in vivo delivery to tissues, or organs of the subject.

The dosage ranges for the composition comprising a cell of interest includes amounts large enough to produce the desired effect, e.g., expression of the desired gene product (e.g., an antibody), or treatment of a disease, e.g., cancer and/or autoimmune disease. The dosage should not be so large as to cause unacceptable adverse side effects. Generally, the dosage will vary with the particular characteristics of cell of interest, and with the age, condition, and sex of the patient. The dosage can be determined by one of skill in the art and, unlike traditional cell therapies, can also be adjusted by the individual physician in the event of any complication.

In some embodiments, the cells of interest are delivered for a repeated or limited amount of time. In some embodiments, the doses are given once a day, or multiple times a day. The duration of treatment depends upon the subject's clinical progress and responsiveness to therapy.

Compositions comprising the aptamer-selected cells of interest (or a cell population depleted of aptamer-binding target cells) can be delivered to target cells or tissues by surgical implantation, intravenous administration, intra-arterial administration, intraperitoneal administration, limb perfusion, (optionally, isolated limb perfusion of a leg and/or arm; see, e.g., Arruda et al., (2005) *Blood* 105: 3458-3464), and/or direct intramuscular injection. Administration to a muscle (e.g., the diaphragm) can be by any suitable method including intravenous (i.v. or iv) administration, intra-arterial administration, and/or intra-peritoneal (i.p.) administration.

In some embodiments, one or more additional compounds can also be included with the cells of interest (i.e., aptamer-selected cells or a cell population depleted of aptamer-binding cells) to alleviate symptoms of a disease or to otherwise assist or support the function of the administered cells.

In some embodiments, the additional compound can be a therapeutic agent. The therapeutic agent can be selected from any class suitable for the therapeutic objective. In other words, the therapeutic agent can be selected according to the treatment objective and biological action desired. Furthermore, the active ingredients of the therapeutic agent can be mixed with optional pharmaceutical additives such as excipients or carriers which are pharmaceutically acceptable and compatible with the active ingredient.

Therapeutic monocytes and/or macrophages can further comprise a targeting moiety for the tissue of interest. For example, the targeting moiety can comprise a receptor molecule, including receptors that naturally recognize a specific desired molecule of a target cell (e.g., a tumor cell). Such receptor molecules include receptors that have been modified to increase their specificity of interaction with a target molecule, receptors that have been modified to interact with a desired target molecule not naturally recognized by the receptor, and fragments of such receptors (see, e.g., Skerra, (2000) *J. Mol. Recognit.* 13:167-187). In other embodiments, the targeting moiety can comprise a ligand molecule, including, for example, ligands which naturally recognize a specific desired receptor on a target cell. Such ligand molecules include ligands that have been modified to increase their specificity of interaction with a target receptor, ligands that have been modified to interact with a desired receptor not naturally recognized by the ligand, and fragments of such ligands. In other embodiments, the targeting moiety can comprise an aptamer that has not been used in the initial cell selection as described herein.

For use in the various aspects described herein, an effective amount of macrophages and/or monocytes, comprises at least $10^2$ macrophages and/or monocytes, at least $5 \times 10^2$ macrophages and/or monocytes, at least $10^3$ macrophages and/or monocytes, at least $5 \times 10^3$ macrophages and/or monocytes, at least $10^4$ macrophages and/or monocytes, at least $5 \times 10^4$ macrophages and/or monocytes, at least $10^5$ macrophages and/or monocytes, at least $2 \times 10^5$ macrophages and/or monocytes, at least $3 \times 10^5$ macrophages and/or monocytes, at least $4 \times 10^5$ macrophages and/or monocytes, at least $5 \times 10^5$ macrophages and/or monocytes, at least $6 \times 10^5$ macrophages and/or monocytes, at least $7 \times 10^5$ macrophages and/or monocytes, at least $8 \times 10^5$ macrophages and/or monocytes, at least $9 \times 10^5$ macrophages and/or monocytes, at least $1 \times 10^6$ macrophages and/or monocytes, at least $2 \times 10^6$ macrophages and/or monocytes, at least $3 \times 10^6$ macrophages and/or monocytes, at least $4 \times 10^6$ macrophages and/or monocytes, at least $5 \times 10^6$ macrophages and/or monocytes, at least $6 \times 10^6$ macrophages and/or monocytes, at least $7 \times 10^6$ macrophages and/or monocytes, at least $8 \times 10^6$ macrophages and/or monocytes, at least $9 \times 10^6$ macrophages and/or monocytes, at least $1 \times 10^7$ macrophages and/or monocytes, at least $2 \times 10^7$ macrophages and/or monocytes, at least $3 \times 10^7$ macrophages and/or monocytes, at least $4 \times 10^7$ macrophages and/or monocytes, at least $5 \times 10^7$ macrophages and/or monocytes, at least $6 \times 10^7$ macrophages and/or monocytes, at least $7 \times 10^7$ macrophages and/or monocytes, at least $8 \times 10^7$ macrophages and/or monocytes, at least $9 \times 10^7$ macrophages and/or monocytes, at least $1 \times 10^8$ macrophages and/or monocytes, at least $2 \times 10^8$ macrophages and/or monocytes, at least $3 \times 10^8$ macrophages and/or monocytes, at least $4 \times 10^8$ macrophages and/or monocytes, at least $5 \times 10^8$ macrophages and/or monocytes, at least $6 \times 10^8$ macrophages and/or monocytes, at least $7 \times 10^8$ macrophages and/or monocytes, at least $8 \times 10^8$ macrophages and/or monocytes, at least $9 \times 10^8$ macrophages and/or monocytes, at least $1 \times 10^9$ macrophages and/or monocytes, at least $2 \times 10^9$ macrophages and/or monocytes, at least $5 \times 10^9$ macrophages and/or monocytes, at least $1 \times 10^{10}$ macrophages and/or monocytes, at least $2 \times 10^9$ macrophages and/or monocytes, at least $5 \times 10^9$ macrophages and/or monocytes, at least $1 \times 10^{10}$ macrophages and/or monocytes, at least $2 \times 10^{10}$ macrophages and/or monocytes, at least $5 \times 10^{10}$ macrophages and/or monocytes, at least $1 \times 10^{11}$ macrophages and/or monocytes, at least $2 \times 10^{11}$ macrophages and/or monocytes, at least $5 \times 10^{11}$ macrophages and/or monocytes, at least $1 \times 10^{12}$ macrophages and/or monocytes, at least $2 \times 10^{12}$ macrophages and/or monocytes, at least $5 \times 10^{12}$ macrophages and/or monocytes, at least $1 \times 10^{13}$ macrophages and/or monocytes, or multiples thereof. In some embodiments of the aspects described herein, the macrophages and/or monocytes are expanded in culture prior to administration to a subject in need thereof.

In one embodiment, the term "effective amount" as used herein refers to the amount of a population of macrophages and/or monocytes needed to alleviate at least one or more symptom of a disease (e.g., autoimmune disease or cancer), and relates to a sufficient amount of a composition to provide the desired effect, e.g., treat a subject having an autoimmune disease or cancer. The term "therapeutically effective amount" therefore refers to an amount of macrophages and/or monocytes or a composition comprising thereof that is sufficient to promote a particular effect when administered to a typical subject, such as one who has or is at risk of an autoimmune disease or cancer. An effective amount as used herein would also include an amount sufficient to prevent or delay the development of a symptom of the disease, alter the course of a symptom disease (for example but not limited to, slow the progression of a symptom of the disease), or reverse a symptom of the disease. It is understood that for any given case, an appropriate "effective amount" can be determined by one of ordinary skill in the art using routine experimentation.

As used herein, "administered" refers to the delivery of a composition comprising macrophages and/or monocytes as described herein into a subject by a method or route which results in at least partial localization of the cell composition at a desired site. A cell composition can be administered by any appropriate route which results in effective treatment in the subject, i.e., administration results in delivery to a desired location in the subject where at least a portion of the composition delivered, i.e., at least $1 \times 10^4$ cells are delivered to the desired site for a period of time. Modes of administration include injection, infusion, instillation, or ingestion. "Injection" includes, without limitation, intravenous (i.v. or iv), intramuscular (i.m. or im), intra-arterial, intrathecal, intraventricular, intracapsular, intraorbital, intracardiac, intradermal, intraperitoneal (i.p. or ip), transtracheal, subcutaneous (sq), subcuticular, intraarticular, sub capsular, subarachnoid, intraspinal, intracerebro spinal, and intrasternal injection and infusion. For the delivery of cells, administration by injection or infusion is generally preferred.

In one embodiment, the cells as described herein are administered systemically. The phrases "systemic administration," "administered systemically", "peripheral administration" and "administered peripherally" as used herein refer to the administration of a population of macrophages and/or monocytes other than directly into a target site, tissue, or organ, such that it enters, instead, the subject's circulatory system and, thus, is subject to metabolism and other like processes.

The efficacy of a treatment comprising a composition as described herein for the treatment of a given disease can be determined by the skilled clinician. However, a treatment is considered "effective treatment," as the term is used herein, if any one or all the signs or symptoms of the disease are altered in a beneficial manner, other clinically accepted symptoms or markers of disease are improved or ameliorated, e.g., by at least 10% following treatment with the cells. Efficacy can also be measured by failure of an individual to worsen as assessed by hospitalization or need for medical interventions (e.g., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing the progression of a given disease; or (2) relieving the disease, e.g., causing regression of symptoms; and (3) preventing or reducing the likelihood of the development of disease.

Following in vitro or ex vivo cell culture, isolation, or differentiation as described herein, isolated or enriched monocyte or macrophage cells are prepared for treatment and/or implantation. The cells are suspended in a physiologically compatible carrier, such as cell culture medium (e.g., Eagle's minimal essential media), phosphate buffered saline, or a macrophage and/or monocyte specific medium. The volume of cell suspension to be implanted will vary depending on the site of implantation, treatment goal, and cell density in the solution.

It will be appreciated by one of skill in the art that a cell composition useful for treating a given disease does not need to be a pure, homogeneous culture of e.g., macrophages and/or monocytes. Accordingly, in one embodiment, the composition administered comprises at least 2% macrophages and/or monocytes. In other embodiments, the composition comprises at least 3%, at least 4%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 99% or more macrophages and/or monocytes as described herein.

The cells can be administered to a subject by any appropriate route that results in delivery of the cells to a desired location in the subject where at least a portion of the cells remain viable. It is preferred that at least 5% remain viable. In other embodiments, at least 10%, at least 20%, at least 30%, at least 40%, or at least 50%, at least 60%, at least 70%, at least 80%, at least 90%, at least 95%, at least 98%, at least 99% or more of the cells remain viable after administration into a subject. The period of viability of the cells after administration to a subject can be as short as a few hours, e.g., twenty-four hours, to a few days, to as long as a few weeks to months.

To accomplish these methods of administration, the cell composition(s) can be inserted into a delivery device that facilitates introduction by injection or implantation of the cells into the subject. Typically, the cells are injected into the target area as a cell suspension. Alternatively, the cells can be embedded in a solid or semisolid support matrix when contained in such a delivery device.

In some embodiments, administration of a composition comprising macrophages and/or monocytes is repeated after a given interval of time (e.g., one day, three days, one week, two weeks, three weeks, one month or more. Repeated treatments can be performed, for example, to establish or maintain a threshold level of engraftment necessary to continue effective treatment, as necessary, of a hemoglobinopathy. In some embodiments, the method is repeated twice, three times, four times, five times or more.

Aptamer Therapeutics and Other Uses

Aptamers have been widely used as targeting ligands to mediate delivery of a variety of payloads to cellular or intracellular targets (e.g., HER2, nucleolin). Payloads include therapeutic drugs, imaging compounds, or unstable molecules (e.g., nucleic acids). In cancer therapy, aptamers can be used to facilitate delivery of therapeutics to cancer cells with high targeting efficiency. In many cancers, tumor cells upregulate specific biomarkers; targeted aptamers can guide nanomedicine systems to deliver therapeutic payloads to these cells, reducing off-target toxicity. These nanomedicine platforms include liposomes, polymeric micelles, or iron oxide nanoparticles. Efficacy of these platforms has been demonstrated both in vitro and in vivo. (See e.g., Alshaer, W. et al. Aptamer-guided nanomedicines for anticancer drug delivery. (2018) Adv. Drug Deliv. Rev. 134: 122-137; Ray and White; Aptamers for Targeted Drug Delivery. (2010) *Pharmaceuticals* 3:1761-1778; Meng, H-M. et al. Aptamer-integrated DNA nanostructures for biosensing, bioimaging and cancer therapy. (2016) *Chem. Society Rev.* 45:2583-2602).

Thus, specifically contemplated herein is the use of the aptamers described herein as a drug delivery device for targeting a given drug to monocytes and/or macrophages. Also contemplated herein is the use of such aptamers to target a therapeutic drug and/or a therapeutic cell to monocytes and/or macrophages. In certain embodiments the aptamer is attached to the therapeutic drug and/or therapeutic cell.

In another embodiment, the aptamers described herein are contemplated for use as sensors or as a theranostic. Some aptamers can undergo significant conformation change upon binding to their ligand or receptor. These switching aptamers can be labeled with a reporter molecule (e.g., a fluorophore for fluorescence detection or a redox probe for electrochemical detection) to provide a signal change upon ligand binding. In another example, aptamers can also be designed to be in duplex structures until binding to their target; binding releases a fluorescently labeled complementary strand, called a "beacon" (see e.g., Tuleuova and Revzin. Micropatterning of aptamer beacons to create cytokine-sensing surfaces. (2010) *Cell Mol. Bioeng.* 3:337-344; Iliuk, et al. Aptamer in bioanalytical applications. (2011) *Anal. Chem.* 83:4440-4452). The aptamers presented in this application could similarly be used to report the presence and relative number of monocyte or macrophage cells by engineering the aptamer into an aptamer reporter.

Pharmaceutical Compositions, Administration and Efficacy

Pharmaceutical or therapeutic compositions comprising an aptamer or aptamer-isolated cells for the treatment of a given disease or disorder can contain a physiologically tolerable carrier, wherein the therapeutic agent is dissolved or dispersed therein as an active ingredient(s). In a preferred embodiment, the pharmaceutical composition is not immunogenic when administered to a mammal or human patient for therapeutic purposes. As used herein, the terms "pharmaceutically acceptable", "physiologically tolerable" and grammatical variations thereof, as they refer to compositions, carriers, diluents, and reagents, are used interchangeably and represent that the materials are capable of administration to or upon a mammal without the production of undesirable physiological effects such as nausea, dizziness, gastric upset, and the like. A pharmaceutically acceptable carrier will not promote the raising of an immune response to an agent with which it is admixed, unless so desired. The preparation of a pharmacological or pharmaceutical composition that contains active ingredients dissolved or dispersed therein is well understood in the art and need not be limited based on formulation. Typically, such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising an aptamer or a population of aptamer-enriched cells for treatment of a disease or disorder can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine, and the like.

Physiologically tolerable carriers are well known in the art. Exemplary liquid carriers are sterile aqueous solutions that contain no materials in addition to the active ingredients and water or contain a buffer such as sodium phosphate at physiological pH value, physiological saline, or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of disease or a symptom thereof will depend on the nature of the disorder or condition and can be determined by standard clinical techniques.

A pharmaceutical composition as described herein can be formulated for parenteral administration, e.g., by bolus injection or continuous infusion. Formulations for injection can be presented in unit dosage form, e.g., in ampoules or in multidose containers with, optionally, an added preservative. The compositions can be suspensions, solutions, or emulsions in oily or aqueous vehicles, and can contain formulatory agents such as suspending, stabilizing, and/or dispersing agents.

Pharmaceutical compositions for parenteral administration include aqueous solutions of the active preparation in water-soluble form. Additionally, suspensions of the active ingredients can be prepared as appropriate oily or water-based injection suspensions.

Suitable lipophilic solvents or vehicles include fatty oils such as sesame oil, or synthetic fatty acid esters such as ethyl oleate, triglycerides, or liposomes. Aqueous injection suspensions can contain substances that increase the viscosity of the suspension, such as sodium carboxymethyl cellulose, sorbitol, or dextran.

Optionally, the suspension can also contain suitable stabilizers or agents that increase the solubility of the active ingredients, to allow for the preparation of highly concentrated solutions. Alternatively, the active ingredient can be in powder form for constitution with a suitable vehicle, e.g., a sterile, pyrogen-free, water-based solution, before use.

In some embodiments, a therapeutic aptamer or therapeutic cell composition can be delivered in an immediate release form. In other embodiments, the therapeutic aptamer or therapeutic cell composition can be delivered in a controlled-release system or sustained-release system. Controlled- or sustained-release pharmaceutical compositions can have a common goal of improving drug therapy over the results achieved by their non-controlled or non-sustained-release counterparts. Advantages of controlled- or sustained-release compositions include extended activity of the therapeutic agents, reduced dosage frequency, and increased compliance. In addition, controlled- or sustained-release compositions can favorably affect the time of onset of action or other characteristics, such as blood levels of the therapeutic agent, and can thus reduce the occurrence of adverse side effects. Controlled- or sustained-release of an active ingredient can be stimulated by various conditions, including but not limited to, changes in pH, changes in temperature, concentration or availability of enzymes, concentration or availability of water, or other physiological conditions or compounds.

In one embodiment, a pump can be used (Langer, (1990) *Science* 249:1527-1533; Sefton, (1987) *CRC Crit. Ref Biomed. Eng.* 14:201; Buchwald et al. (1980) *Surgery* 88:507; and Saudek et al. (1989) *N. Engl. J. Med.* 321:574). In another embodiment, polymeric materials can be used (see Medical Applications of Controlled Release (Langer and Wise eds., 1974); Controlled Drug Bioavailability, Drug Product Design and Performance (Smolen and Ball eds., 1984); Ranger and Peppas, (1983) *J. Macromol. Sci. Rev. Macromol. Chem.* 23:61; Levy et al. (1985) *Science* 228: 190; During et al. (1989) *Ann. Neurol.* 25:351; and Howard et al. (1989) *J. Neurosurg.* 71:105). In yet another embodiment, a controlled- or sustained-release system can be placed in proximity of a target of infection, thus requiring only a fraction of the systemic dose.

When in tablet or pill form, a pharmaceutical composition as described herein can be coated (e.g., enterically coated) to delay disintegration and absorption in the gastrointestinal tract, thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

A pharmaceutical composition as described herein can also be formulated in rectal compositions such as suppositories or retention enemas, using, for example, conventional suppository bases such as cocoa butter or other glycerides.

The appropriate dosage range for a given therapeutic agent depends upon the potency and includes amounts large enough to produce the desired effect, e.g., reduction in at least one symptom of a given disease. The dosage of the therapeutic agent should not be so large as to cause unacceptable or life-threatening adverse side effects or should be used under close supervision by a medical professional. Generally, the dosage will vary with the specific aptamer and/or formulation, and with the age, condition, and sex of the patient. The dosage can be determined by one of skill in the art and can also be adjusted by the individual physician in the event of any complication.

Typically, the dosage of a given therapeutic aptamer can range from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 µg/kg body weight to 30 µg/kg body weight. Alternatively, the dose range will be titrated to maintain serum levels between 5 µg/mL and 30 µg/mL.

Administration of the doses recited above or as employed by a skilled clinician can be repeated for a limited and defined period of time. In some embodiments, the doses are given once a day, or multiple times a day, for example, but not limited to three times a day. Typically, the dosage regimen is informed by the half-life of the agent as well as the minimum therapeutic concentration of the agent in blood, serum or localized in a given biological tissue. In a preferred embodiment, the doses recited above are administered daily for several weeks or months. The duration of treatment depends upon the subject's clinical progress and continued responsiveness to therapy. Continuous, relatively low maintenance doses are contemplated after an initial higher therapeutic dose.

A therapeutically effective amount is an amount of an agent that is sufficient to produce a statistically significant, measurable change of a given symptom of disease (see "Efficacy Measurement" below). Such effective amounts can be gauged in clinical trials as well as animal studies for a given agent. For example, reduction of a given symptom of disease can be indicative of adequate therapeutic efficacy of an agent(s).

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. The agent can be administered systemically, if so desired.

Therapeutic compositions containing at least one therapeutic agent can be conventionally administered in a unit dose. The term "unit dose" when used in reference to a therapeutic composition refers to physically discrete units suitable as unitary dosage for the subject, each unit containing a predetermined quantity of a therapeutic agent calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as, e.g., an antibody or targeted liposome technology.

Precise amounts of active ingredient required to be administered depend on the judgment of the practitioner and are particular to each individual. However, suitable dosage ranges for systemic application are disclosed herein and depend on the route of administration. Suitable regimes for administration are also variable but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

In some embodiments, at least one additional therapeutic agent is used in combination with the aptamers or cells described herein for the treatment of a given disease.

In some embodiments, an aptamer composition or therapeutic cell composition is administered to a subject concurrently with a combination therapy. As used herein, the term "concurrently" is not limited to the administration of the two or more agents at exactly the same time, but rather, it is meant that they are administered to a subject in a sequence and within a time interval such that they can act together (e.g., synergistically to provide an increased benefit than if they were administered otherwise). For example, the combination of therapeutics can be administered at the same time or sequentially in any order at different points in time; however, if not administered at the same time, they should be administered sufficiently close in time so as to provide the desired therapeutic effect, preferably in a synergistic fashion. The agents can be administered separately, in any appropriate form and by any suitable route. When each of the therapeutic agents in a combination are not administered in the same pharmaceutical composition, it is understood that they can be administered in any order to a subject in need thereof. For example, the first therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second therapeutic agent, to a subject in need thereof (or vice versa). In other embodiments, the delivery of either therapeutic agent ends before the delivery of the other agent/treatment begins. In some embodiments of either case, the treatment is more effective because of combined administration. For example, the therapeutic agents used in combination are more effective than would be seen with either agent alone. In some embodiments, delivery is such that the reduction in a symptom, or other parameter related to the disorder is greater than what would be observed with either therapeutic agent alone. The effect of such a combination can be partially additive, wholly additive, or greater than additive. The agent and/or other therapeutic agents, procedures or modalities can be administered during periods of active disease, or during a period of persistence or less active disease.

When administered in combination, one or more of the therapeutic agents can be administered in an amount or dose that is higher, lower or the same as the amount or dosage of the given agent used individually, e.g., as a monotherapy. In certain embodiments, the administered amount or dosage of a first therapeutic agent when administered in combination with a second therapeutic agent is lower (e.g., at least 20%, at least 30%, at least 40%, or at least 50%) than the amount or dosage of the first agent when used individually. In other embodiments, the amount or dosage of a first therapeutic agent, when administered in combination with a second therapeutic agent, results in a desired effect (e.g., improved cognitive functioning) is lower (e.g., at least 20%, at least 30%, at least 40%, or at least 50% lower) than the amount or dosage of the first (or second) agent required to achieve the same therapeutic effect when administered alone.

The efficacy of a treatment for a given disease can be determined by the skilled clinician. However, a treatment is considered "effective treatment," as the term is used herein, if any one or all the signs or symptoms of the given disease is/are altered in a beneficial manner, or other clinically accepted symptoms or markers of disease are improved, or ameliorated, e.g., by at least 10% following treatment with a therapeutic aptamer or a population of therapeutic cells as described herein. Efficacy can also be measured by failure of an individual to worsen as assessed by stabilization of the disease, or the need for medical interventions (i.e., progression of the disease is halted or at least slowed). Methods of measuring these indicators are known to those of skill in the art and/or described herein. Treatment includes any treatment of a disease in an individual or an animal (some non-limiting examples include a human, or a mammal) and includes: (1) inhibiting the disease, e.g., arresting, or slowing progression of the disease; or (2) relieving the disease, e.g., causing regression of symptoms; and (3) preventing or reducing the likelihood of the development of the disease, or preventing secondary diseases/disorders associated with the disease.

An effective amount for the treatment of a disease means that amount which, when administered to a mammal in need thereof, is sufficient to result in effective treatment as that term is defined herein, for that disease. Efficacy of an agent can be determined by assessing physical indicators of the disease, such as, e.g., pain, fatigue, fever, and the like.

Kits

In one aspect, provided herein are kits containing any one or more of the elements disclosed in the above methods and compositions. Provided herein are kits comprising aptamers as described herein, and formulations thereof. In one embodiment, the kit comprises, consists of, or consists essentially reagents and instructions for selecting or depleting monocytes or macrophages from a cell population, or for administering an aptamer or a population of aptamer-enriched cells or a population of cells depleted for aptamer-binding cells.

In certain embodiments, the kits comprise one or more solid supports or an aptamer conjugated to a solid support. Kits can also comprise columns, including flow cytometry columns.

The kit can comprise cell reagents including labeling means, salts, growth media, serum etc.

In some embodiments, a kit comprises one or more reagents for use in a process utilizing one or more of the elements described herein. Reagents can be provided in any suitable container. For example, a kit can provide one or more reaction or storage buffers. A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

This invention is further illustrated by the following example which should not be construed as limiting. The contents of all references cited throughout this application, as well as the figures and tables are incorporated herein by reference.

EXAMPLES

The following provides non-limiting Examples demonstrating and supporting the technology as described herein.

Example 1: Identification of a DNA Aptamer that Binds to Human Monocytes and Macrophages Manipulation of immune cell populations, either ex vivo or in situ, has emerged as a powerful technique in cancer therapy. With the ascent of immunotherapies, technologies that facilitate targeting of immune cells that populate the tumor environment has risen in importance. Immunotherapies related to lymphoid cells, such as chimeric antigen receptor (CAR) T-cells (Yescarta™ and Kymriah™) and checkpoint inhibitors (e.g., antibodies against PD-1 or CTLA-4) have shown striking clinical success.[1-4] There is now significant interest in developing immunotherapies related to myeloid cells. Myeloid progenitor cells are derived from the bone marrow and can commit to the monocyte lineage, cells that circulate in the blood and extravasate into tissues where they terminally differentiate into macrophages.[5] Parallel to lymphoid immunotherapies, macrophages have been equipped with cancer-fighting CARs (Charisma Therapeutics) or blocked with immune-checkpoint inhibitors (e.g., antibodies against CD47 or SIRPα).[6-8] Other therapies focus on targeting macrophages within the tumor, but there remains a need to expand the repertoire of targeting ligands for myeloid-derived cells with potential applications in engineered cell manufacturing and targeted drug delivery to these cells.

This demonstrates the identification of novel tumor-associated macrophage (TAM) ligands. TAMs are associated with poor patient prognosis and have been demonstrated to facilitate disease progression by promoting tumor proliferation, metastasis, and immunosuppression.[8-10] Accounting for up to 50-70% of a solid tumor mass in many cancers (e.g., breast cancer, melanoma, and glioblastoma), TAMs have been linked with worse clinical outcome and resistance to conventional therapies, and there are several TAM-targeted strategies under development for cancer treatment.[8,11-14] However, an important consideration is to limit effects to tissue resident macrophages, which are critical for immune defense and anti-tumor activities.[15] In a simplified binary polarization paradigm, inflammatory macrophages exhibit an M1-like phenotype and have cytotoxic functions, whereas TAMs more closely resemble an M2-like phenotype, which is associated with tissue healing and remodeling.[16] In the context of cancer, this M2-like phenotype supports tumor angiogenesis, growth, and dissemination.[9]

In previous work, it was demonstrated that targeted depletion of this M2-like population can prolong survival in tumor bearing mice.[17] Using a subtractive phage panning strategy against murine bone marrow derived macrophages (BMDMs) polarized to M1- and M2-like phenotypes, a peptide sequence, M2pep, was identified that preferentially bound murine M2-like macrophages with low affinity for other leukocytes. Utilizing M2pep for targeted delivery of a pro-apoptotic peptide to M2-like TAMs reduced tumor growth rate and prolonged survival. However, M2pep does not bind human macrophages, limiting clinical applicability. Extensive efforts to identify a human equivalent of M2pep were unsuccessful, prompting the search for an aptamer ligand against human M2-like TAMs. Aptamers are single-stranded DNA or RNA oligonucleotides that can form unique secondary structures capable of specific molecular recognition of cognate targets.[18] These synthetic ligands offer high binding affinity ($K_d$ in the pM-nM range), long shelf-life, and fast production.

Here, a DNA aptamer ligand that specifically binds human M2-like macrophages because of their resemblance to TAMs was identified that demonstrates minimal binding to tissue resident M0-like macrophages or circulating monocytes. Despite receptor overlap between phenotypes, it was hypothesized that aptamers would be able to provide enough specificity due to their ability to differentiate proteins with single amino acid mutations.[19] Cell-based systematic enrichment of ligands was employed using exponential enrichment (SELEX), an emerging method to identify aptamer ligands against whole-cell targets.[20] Binding was characterized by flow cytometry, droplet digital (dd) PCR, and fluorescent microscopy. Ultimately, a novel aptamer was identified that exhibits high binding to monocytes, M0- and M2-like macrophages, yet shows minimal binding to M1-like macrophages. Despite binding to these varied populations, this aptamer can be used for in situ binding to monocytes in disease models with monocyte dysregulation (e.g., cancer and infectious disease) or for in vitro applications, such as column selection of monocytes from white blood cells for production of engineered monocyte or macrophage cell therapies.[21,22]

Results

Figure 5A:
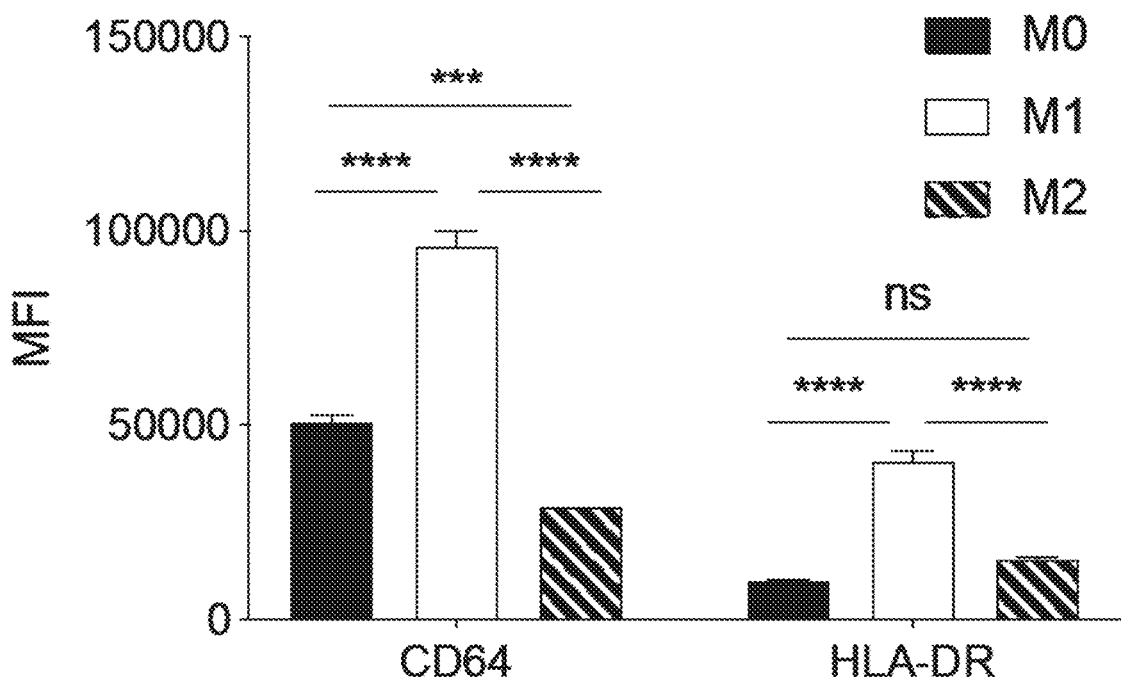
FIGS. 5A-5B: Macrophage phenotype validation by flow cytometry. Isolated monocytes were cultured and polarized into M0-, M1-, and M2-like macrophages. Macrophage phenotype was confirmed by assessing M1 markers CD64 and HLA-DR (FIG. 5A) and M2 markers CD36 and CD180 (FIG. 5B). Significance was determined by ANOVA (CD64 M0 vs M2 *p=0.0001; p<0.0001) (HLA-DR p<0.0001) (CD36 p<0.0001) (CD180 p<0.0001) (CD206 M0 vs M2 p=0.0056; M1 vs M2 **p=0.0048).
Figure 5B:
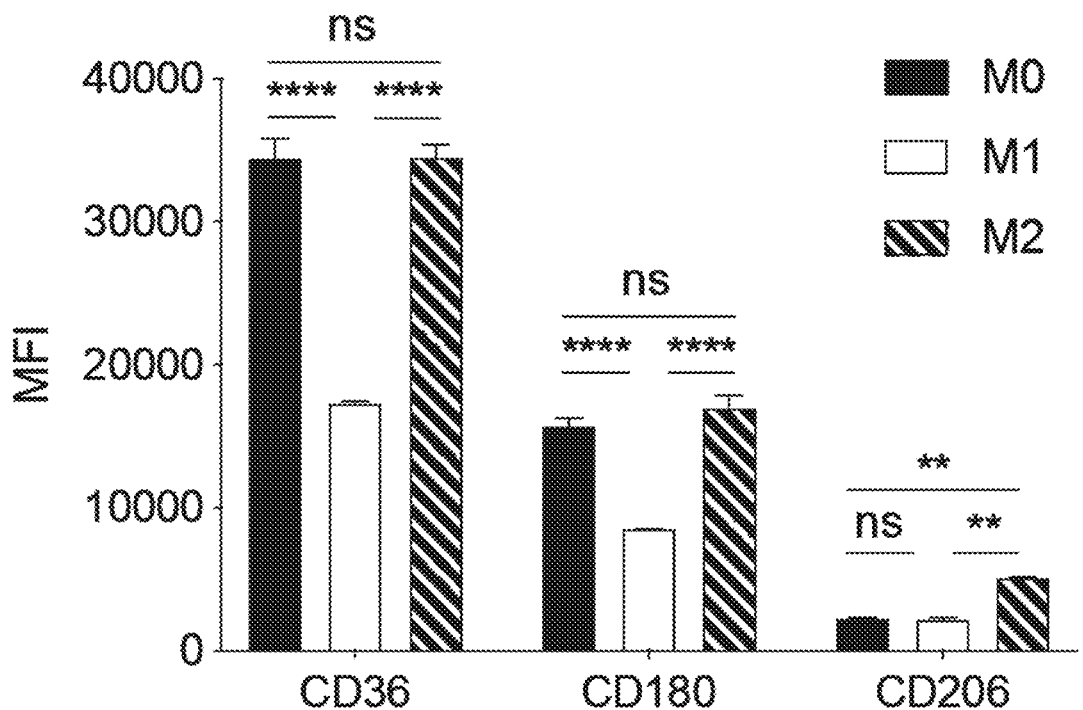
Figure 6B:
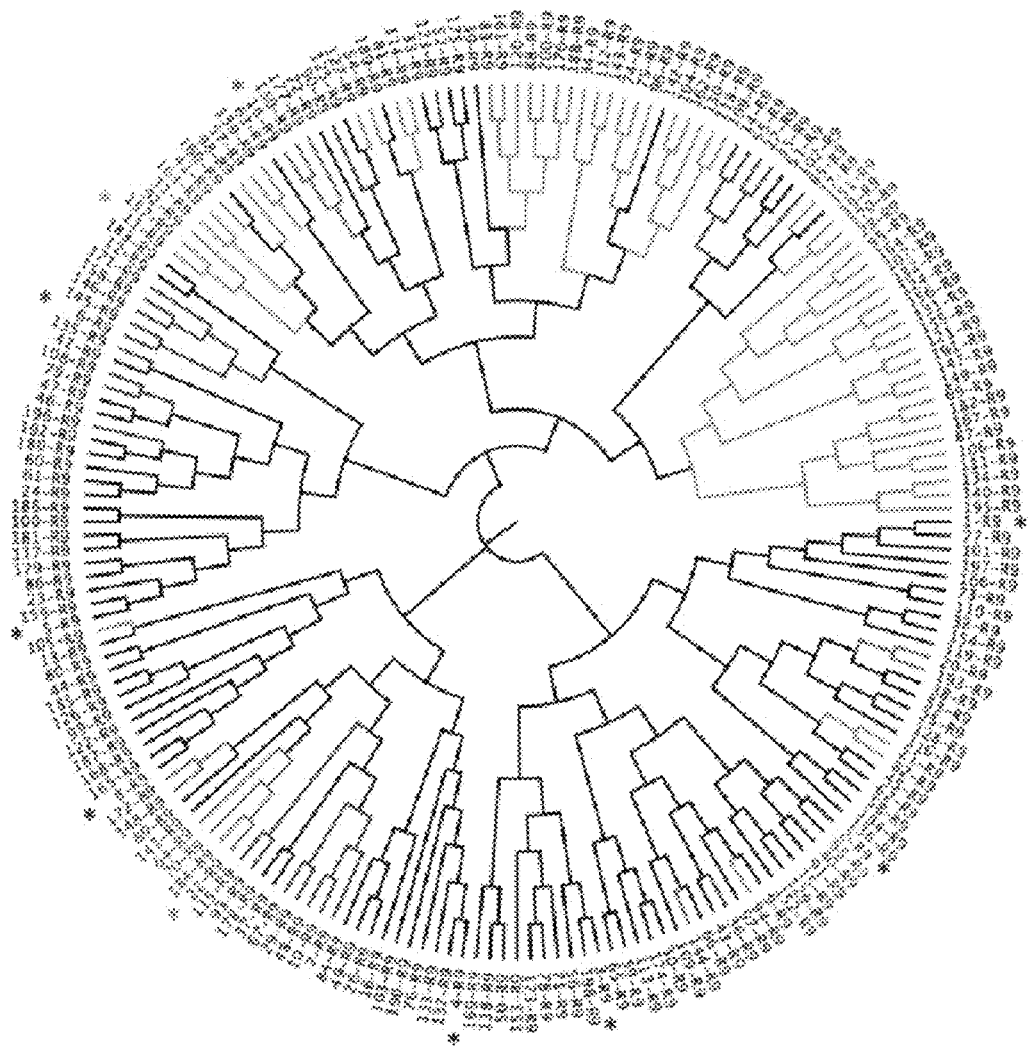
Figure 7:
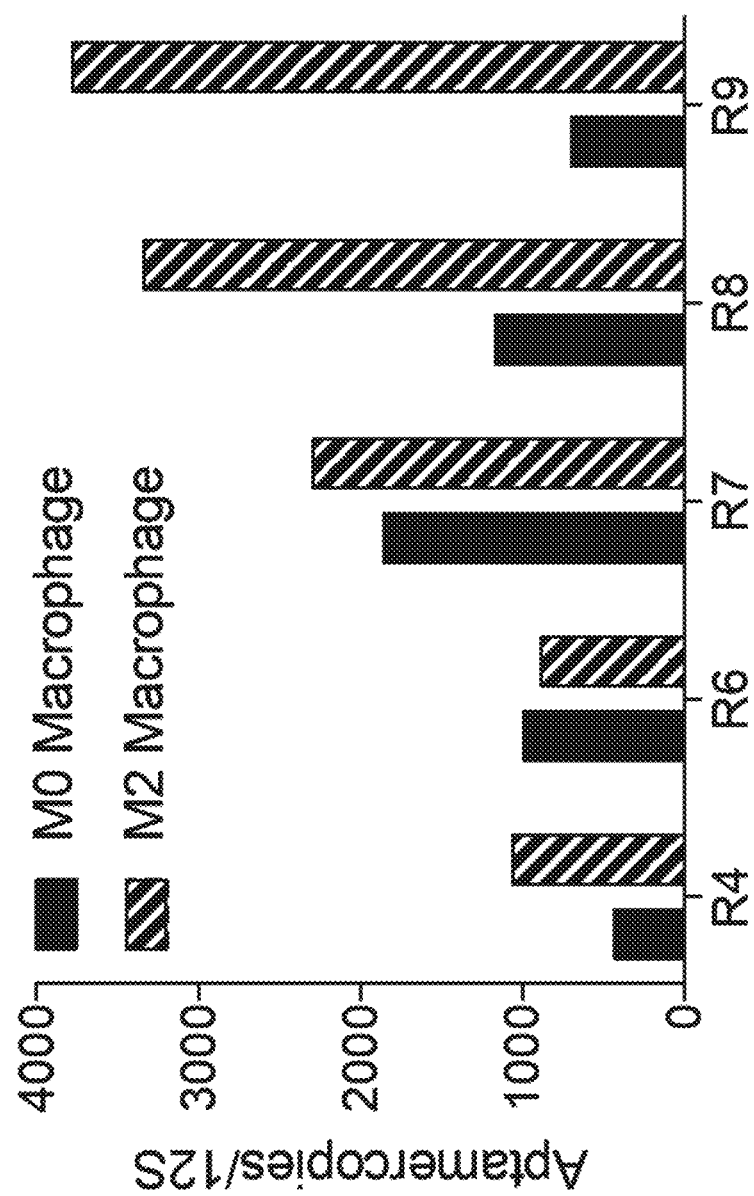
FIG. 7: Round binding to M0- and M2-like macrophages. Resulting aptamer pools (200 nM) from each round were bound against M0- and M2-like macrophages. Aptamers and macrophage DNA were recovered and assessed by droplet digital PCR. Aptamer copies were normalized to cell number (copies of ribosomal RNA 12S gene).
Figure 8A:
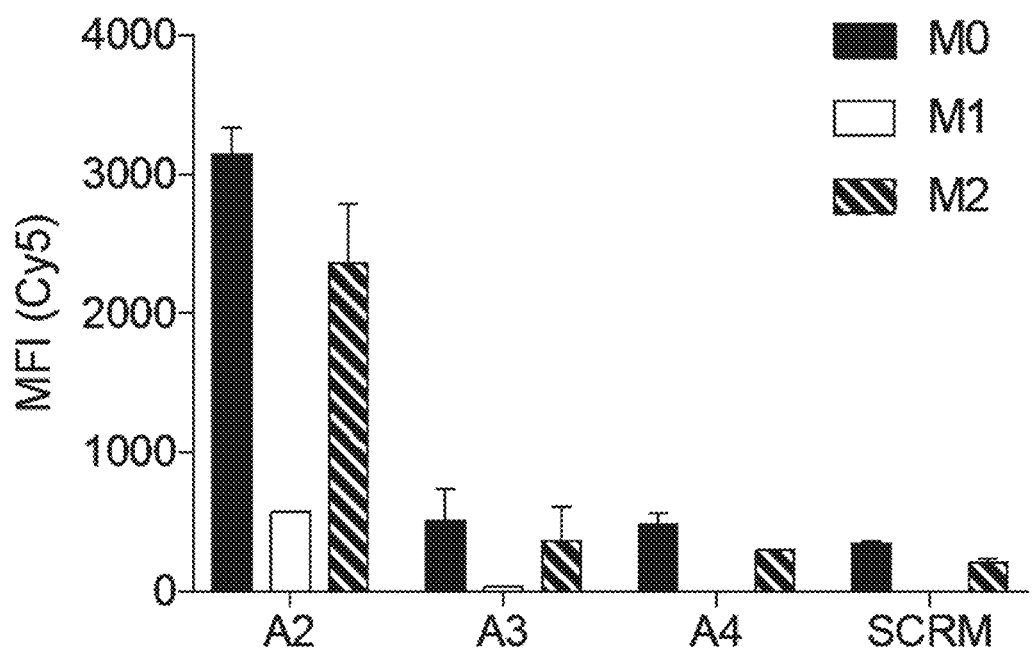
Figure 8B:
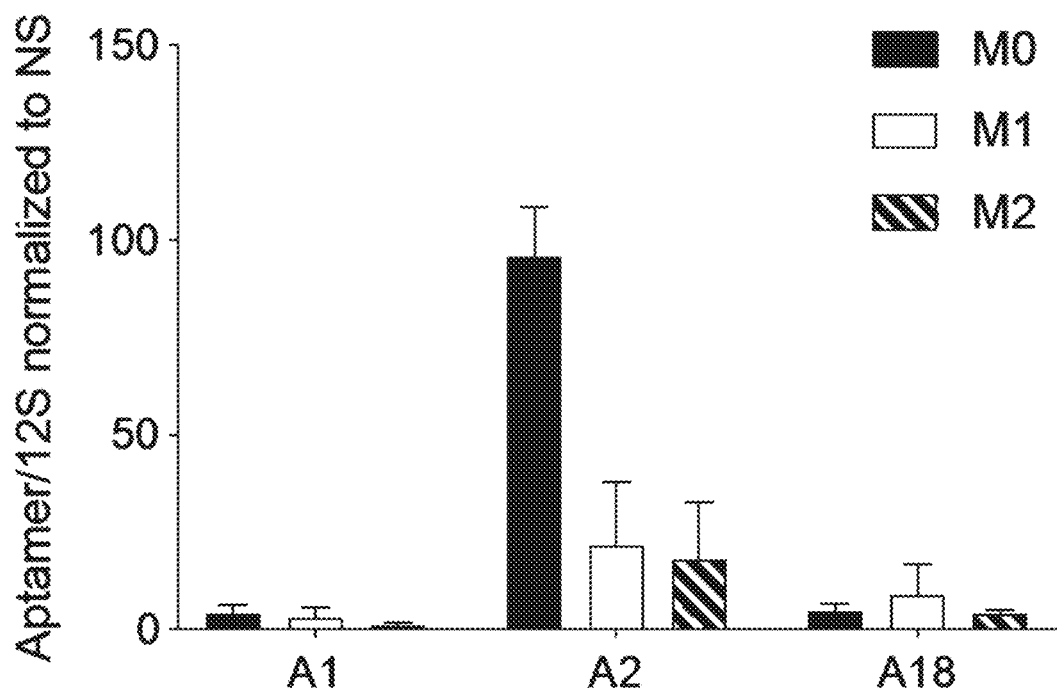

Identification of aptamer A2 by cell-SELEX. To identify an aptamer that binds human M2-like macrophages, cell-SELEX was employed as previously described, using a 52 base-pair (bp) random region DNA aptamer library ($10^{16}$ unique sequences) and human macrophages derived from monocytes, isolated from human leukoreduction system (LRS) chambers.[20] Macrophages were polarized toward M0-, M1-, and M2-like phenotypes by macrophage colony-stimulating factor (M-CSF), lipopolysaccharide (LPS)+interferon gamma (IFN-γ), and interleukin 4 (IL-4) respectively; polarization was confirmed by upregulated CD64 and HLA/DR expression (M1-like macrophages) (FIG. 5A) and CD36 and CD180 expression (M2-like macrophages) by flow cytometry (FIG. 5B). SELEX was performed against M2-like macrophages for positive selection, and monocytes and M0-like macrophages for negative selection (FIGS. 1A-1B). These cells were selected by a desire to target TAMs, which resemble an M2-like phenotype, and to avoid binding to (i) tissue resident macrophages, resembling an M0-like phenotype, and (ii) circulating monocytes, which would be important to bypass for intravenous delivery. Although macrophage polarization exists along a spectrum of phenotypes, cultured macrophages were used to produce more homogenous populations for selection. After 9 rounds of iterative selection with increasing stringency, next generation sequence (NGS) was used to catalog resultant aptamer sequences (FIG. 6A). These were subsequently analyzed using FASTAptamer, phylogenetic trees, and motif analysis (FIGS. 6B and 6C).[23,24] Top aptamers were identified based on (i) abundance (reads per million), (ii) motif (conserved patterns between sequences), (iii) enrichment between starting library, final aptamer pools, and consecutive rounds, and (iv) family representation in phylogenetic trees. Binding of resulting pools and selected top aptamers was validated by droplet digital (dd) PCR (FIG. 7). Droplet digital PCR was used to assess efficiency of retained aptamers from each round of selection because it has higher sensitivity than other methods, such as flow cytometry or quantitative PCR.[25] Selected aptamers from the top 10 ranking sequences (ranked per abundance in the final pool) were ordered based on rank, family representation, and motif, and tested for binding against M0-, M1-, and M2-like macrophages. Aptamer A2, named based on rank in the final aptamer pool, demonstrated the highest binding to M2-like macrophages (FIG. 8A). Interestingly, A2 also demonstrated high binding to M0-like macrophages as well (FIG. 8B). Despite binding to this negative cell selection population, its binding to macrophages and peripheral blood mononuclear cells (PBMCs) was further characterized.

Characterization of aptamer A2 binding to macrophages. The initial screening revealed that aptamer A2 bound both M0- and M2-like macrophages, likely due to overlapping receptor expression and closely related phenotypes of those cells. Based on this binding behavior, it was hypothesized that A2 would bind less to M1-like macrophages, which are more phenotypically disparate with different receptor expression compared to M0- and M2-like macrophages.[26] Binding studies via flow cytometry confirmed that A2 preferentially binds M0- and M2-like macrophages, with apparent dissociation constants ($K_d$) of 44.12±8.0 and 22.81±5.6 nM to M0- and M2-like macrophages, respectively (FIGS.

Figure 2A:
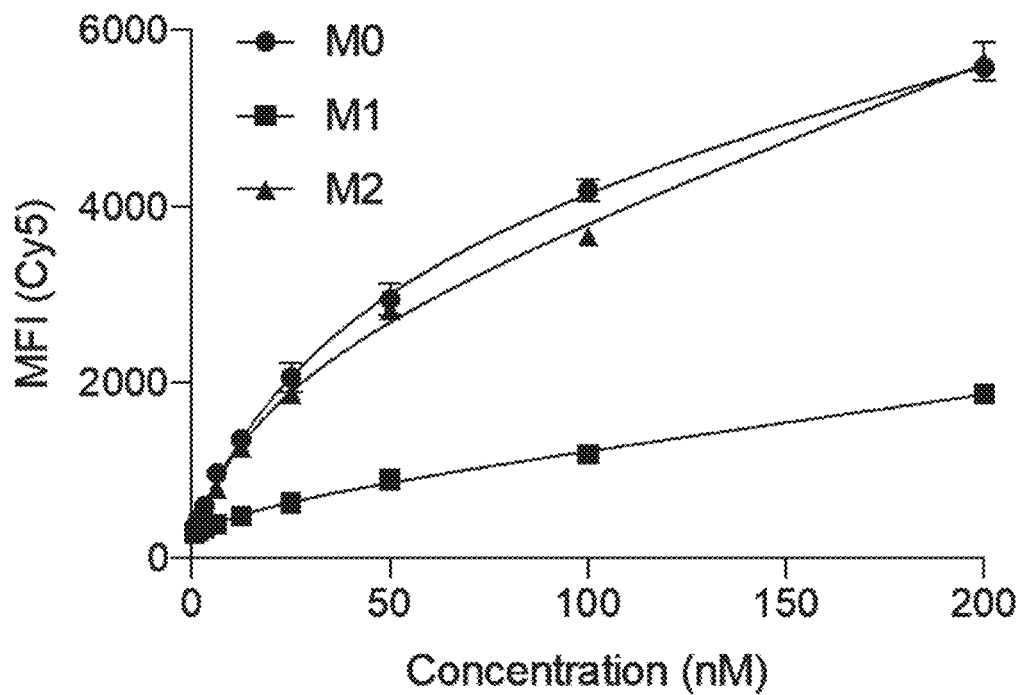
FIGS. 2A-2E: Aptamer binding to human M0-, M1-, and M2-like macrophages.
Figure 2B:
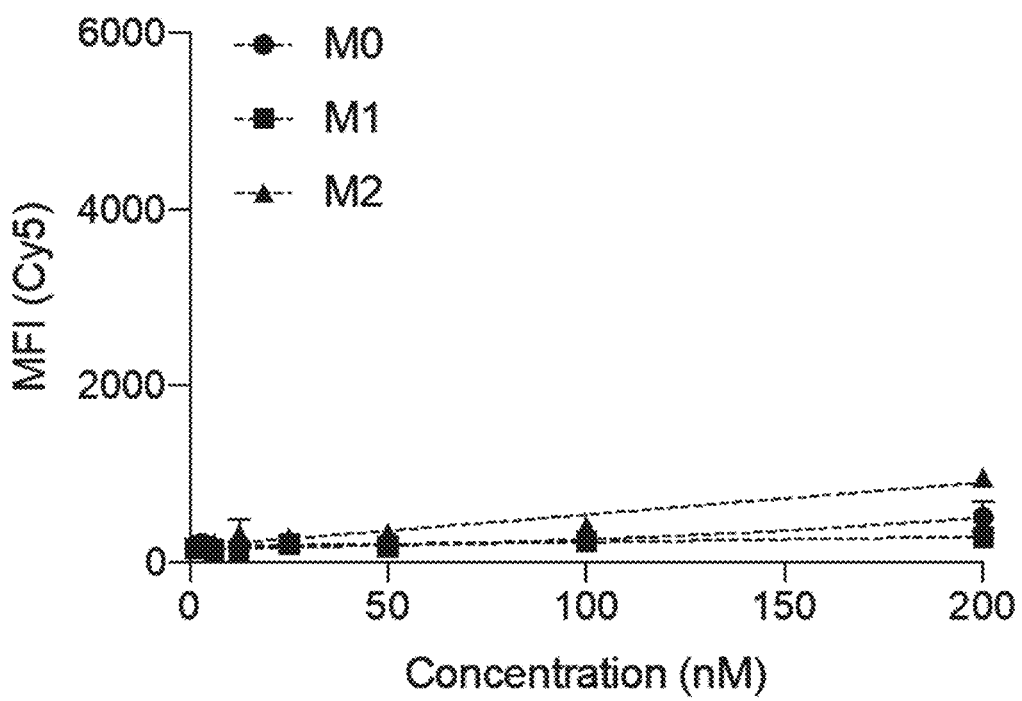
Figures 2C, 2D:
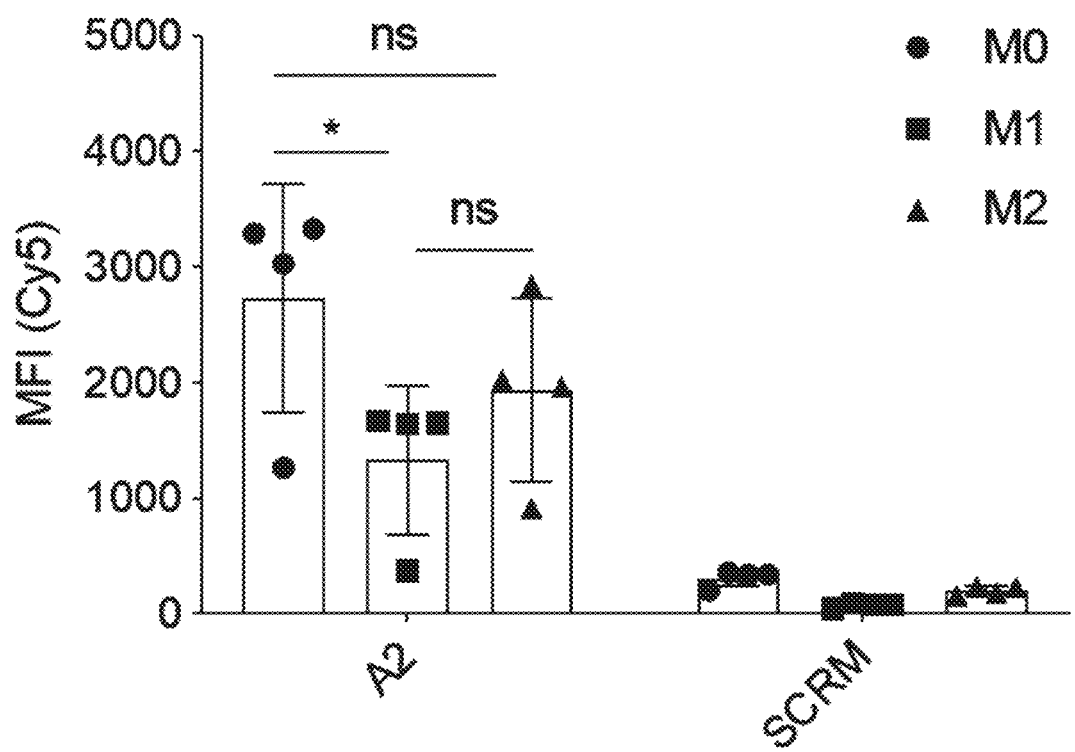
Figure 2E:
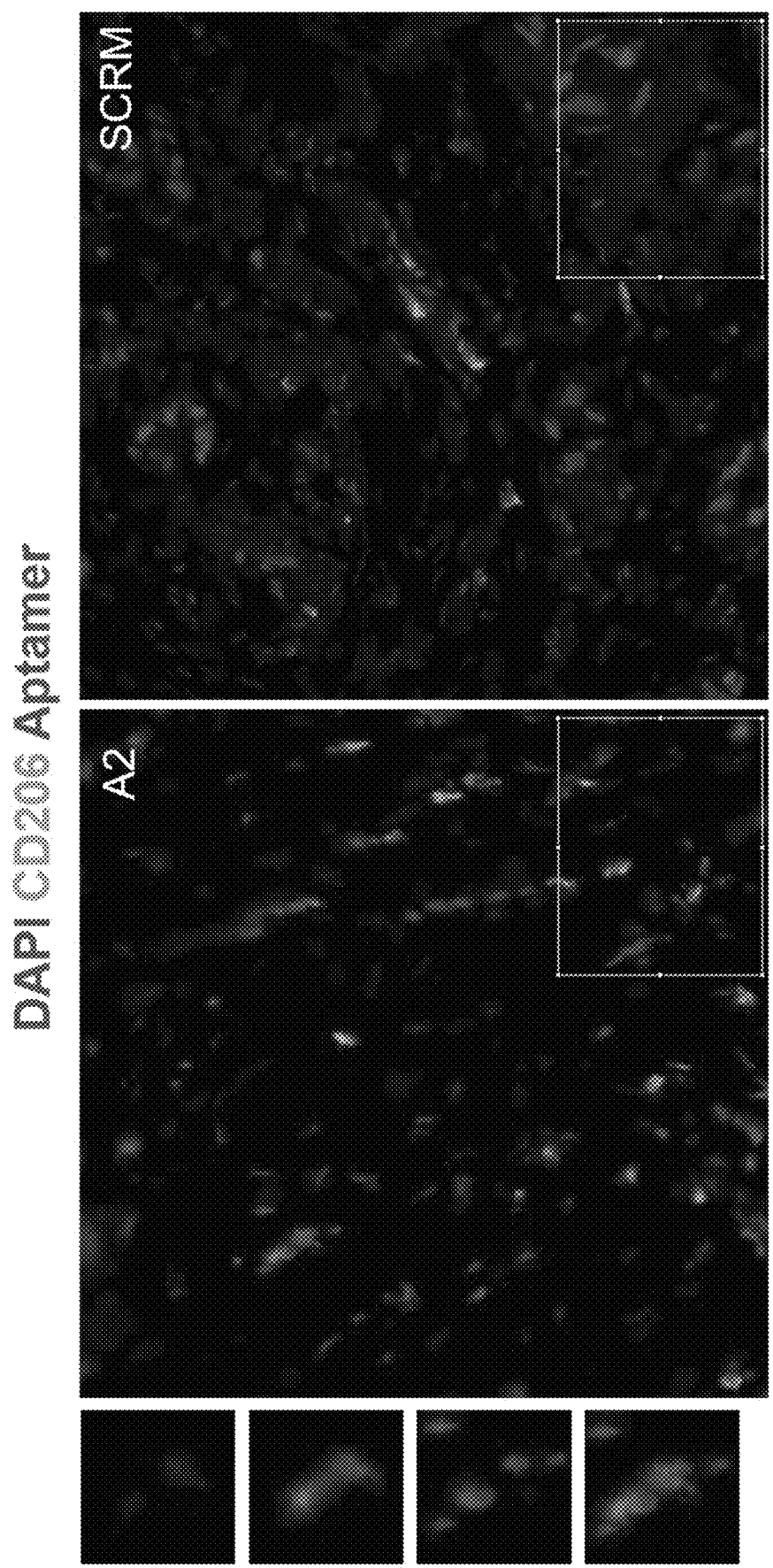

2A, 2C). The maximum binding intensity of A2 to M0- and M2-like macrophages was higher than for M1 macrophages, which indicates higher density of A2-binding receptor expression on M0- and M2-like macrophages versus M1-like macrophages. Binding was compared to a scrambled sequence aptamer control (SCRM), which exhibited no specific binding behavior to M0-, M1-, or M2-like macrophages (FIGS. 2B, 2C). To confirm that binding is specific and not donor-dependent, the inventors assessed binding across unique donors (FIG. 2D). Across donors, aptamer binding to M0-like macrophages was significantly higher than binding to M1-like macrophages (*p=0.03). There was no significant difference in binding of aptamer A2 over SCRM to M1-like macrophages. In contrast, aptamer A2 binding was significantly higher than SCRM binding to M0- (*p=0.0002) and M2-like (p=0.006) macrophages. Based on aptamer A2's binding behavior against cultured macrophages, aptamer binding was next tested against human triple-negative breast cancer (TNBC) tumor sections, which were selected as a target because of their high macrophage infiltration (FIG. 2E). Tumors were sectioned and stained for human CD206, an M2-like macrophage marker (green), DAPI for nuclei (blue), and aptamer (red). Areas with abundant macrophages were imaged, and aptamer A2 showed higher signal in those cells in comparison with SCRM. Furthermore, A2 samples had a staining pattern consistent with that of CD206 staining, while SCRM did not show a consistent pattern (Spearman's rank correlation A2=0.69 vs. Spearman's rank correlation SCRM=0.51).

Figure 3A:
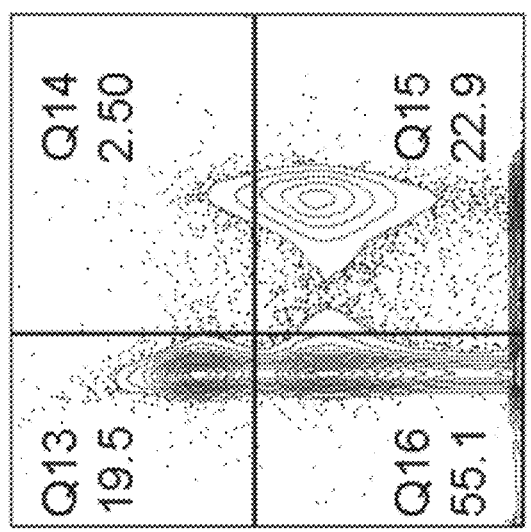
FIGS. 3A-3F: Aptamer binding to $CD14^+$ cells in complete PBMCs.
Figure 3A:
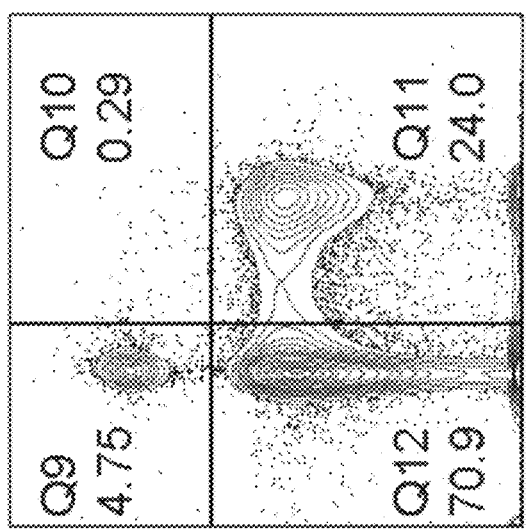
Figure 3A:
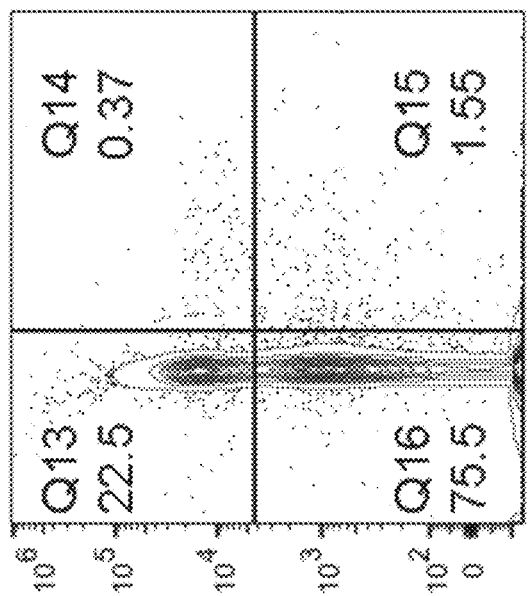
Figure 3A:
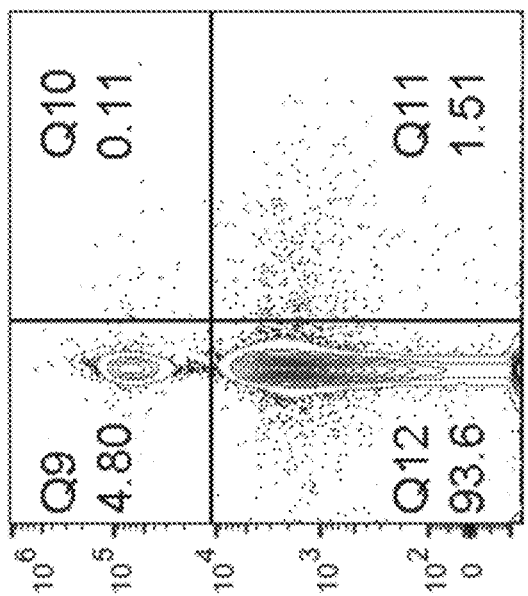
Figure 3A:
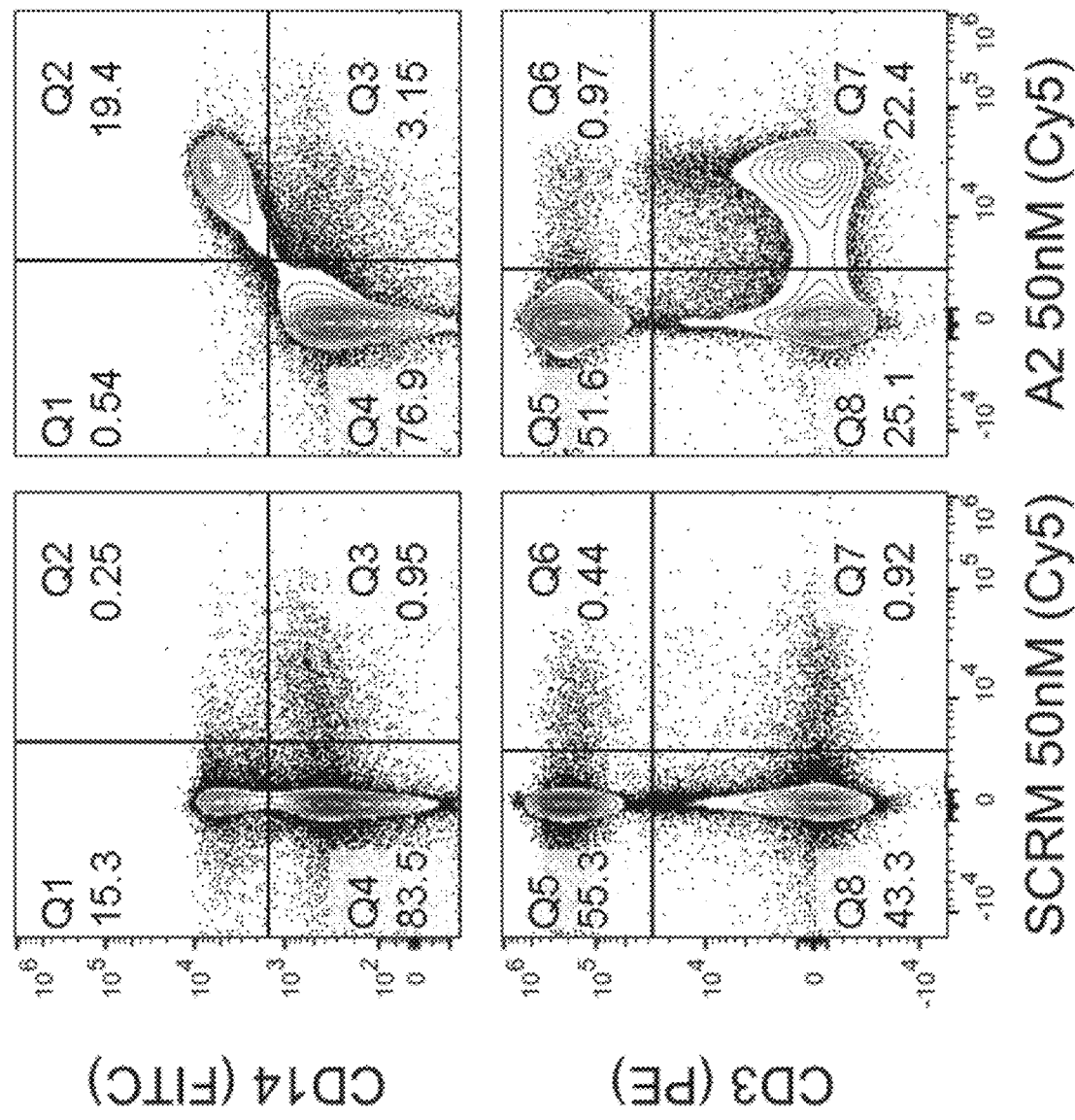
Figure 3B:
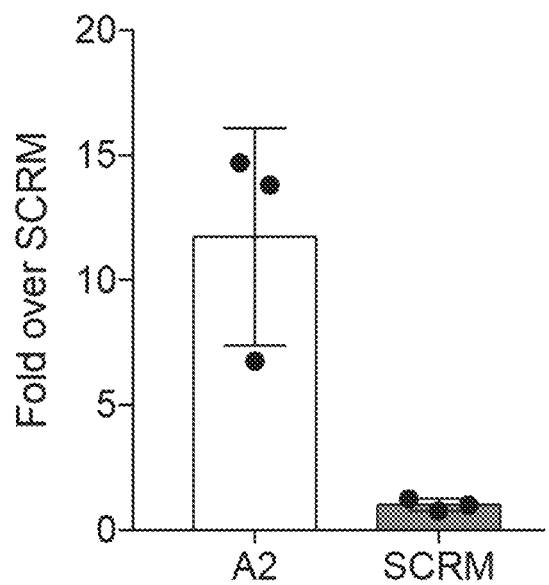
Figure 3C:
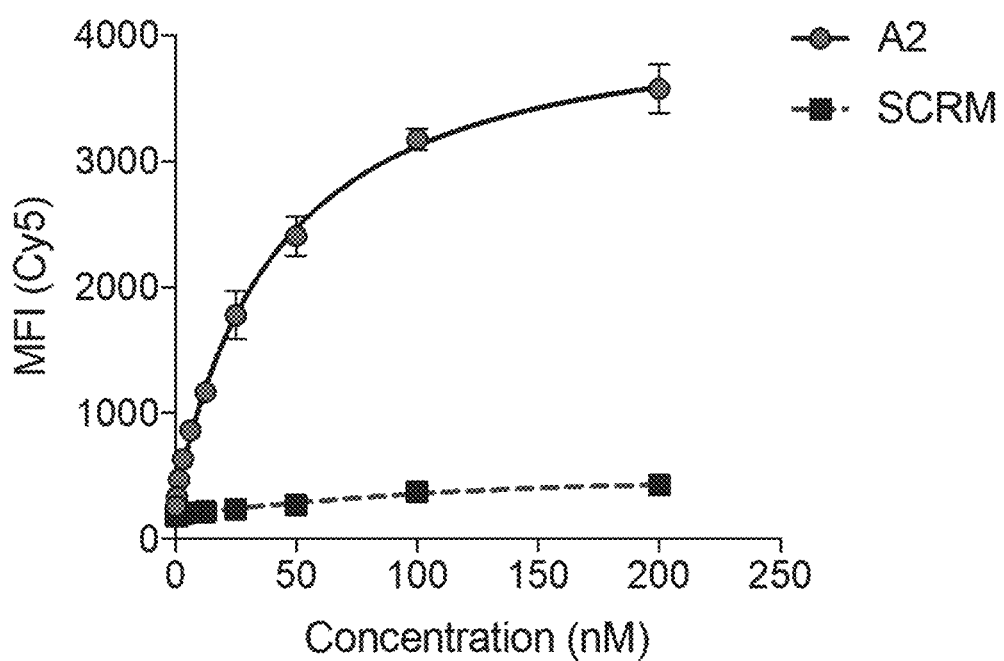

Characterization of aptamer A2 binding to PBMCs. It was next sought to characterize the binding profile of aptamer A2 with PBMCs. For TAM targeting applications, A2 would ideally have low non-specific binding to circulating leukocytes to prevent off-target binding and toxicity. While macrophages are derived from monocytes and thus have some overlapping surface marker expression, it was hypothesized that aptamer A2 would not bind monocytes due to their use as negative selection cells. Nevertheless, aptamer A2 bound CD14$^+$ cells (monocytes) with high specificity ($K_d$~45±9.1 nM), with negligible binding to remaining PBMC cell populations (CD3$^+$ T cells, CD19$^+$ B cells, and CD56$^+$ natural killer cells) (FIGS. 3A, 3C). While aptamer A2 binding to CD14$^+$ monocytes did depend on donor to some extent, binding was consistently above that of SCRM (****p<0.0001) (FIG. 3B). It is likely that variability in donor-to-donor binding can be attributed to varied protein and receptor expression across donors.[27]

Figure 3D:
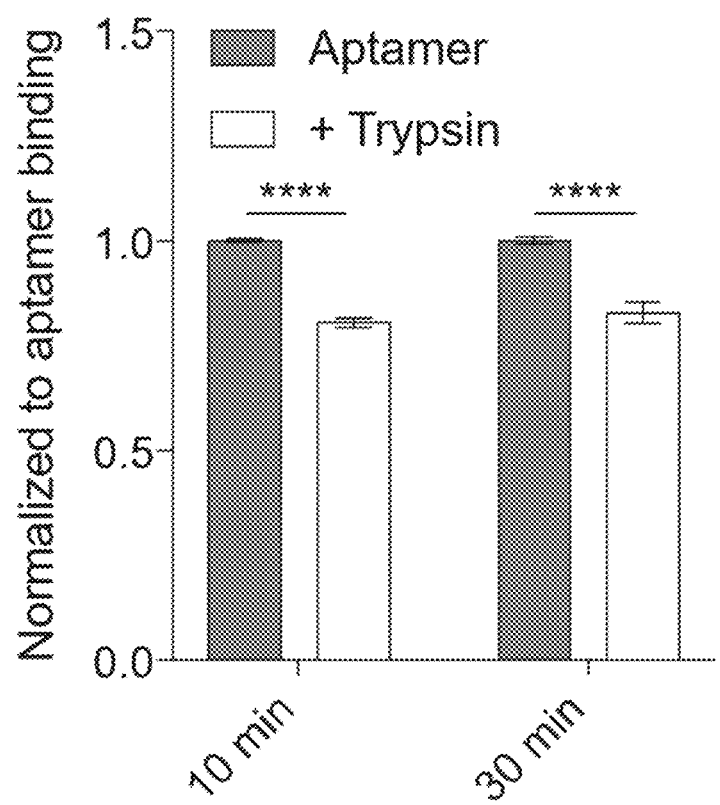
Figure 3E:
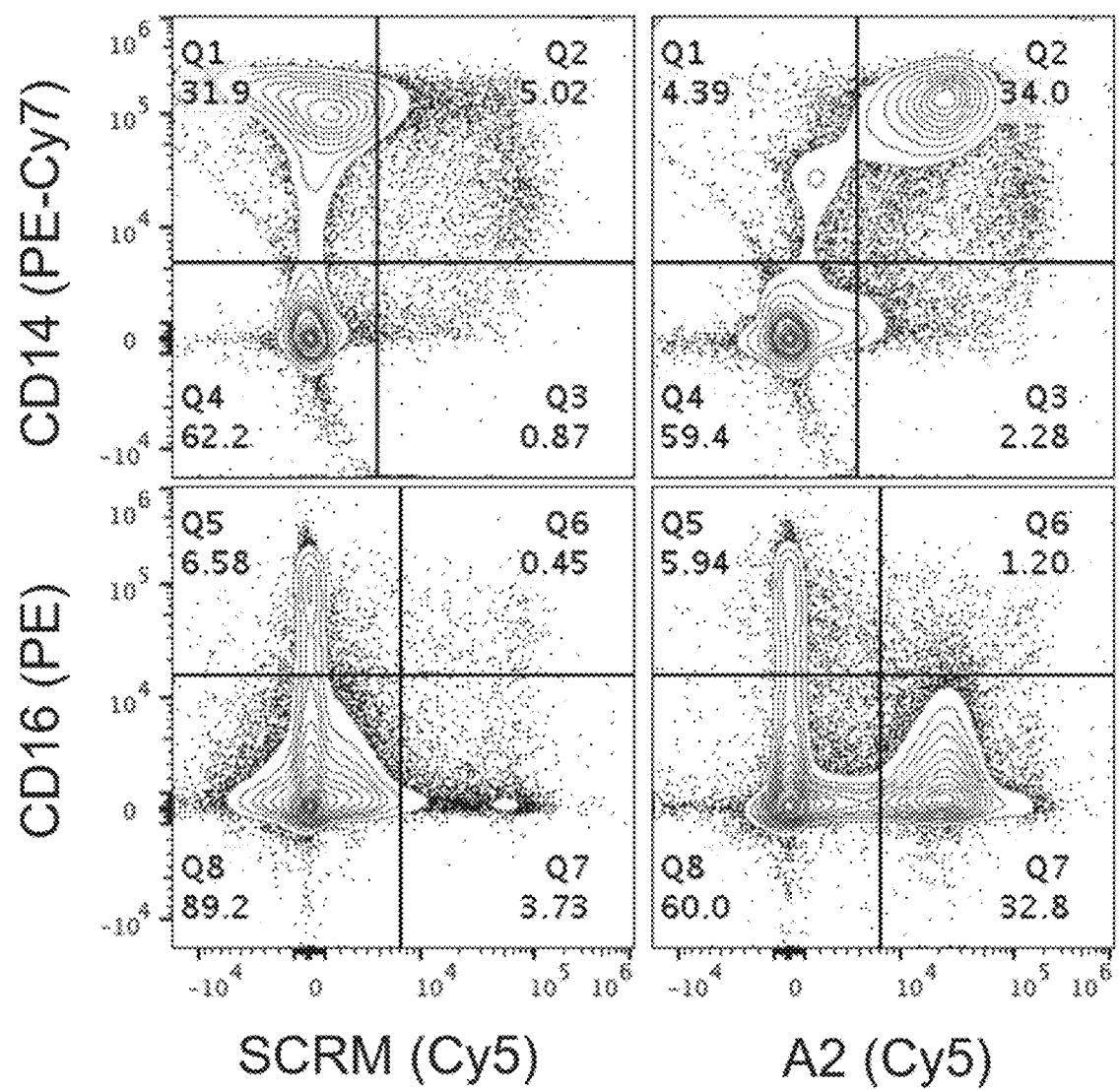
Figure 3F:
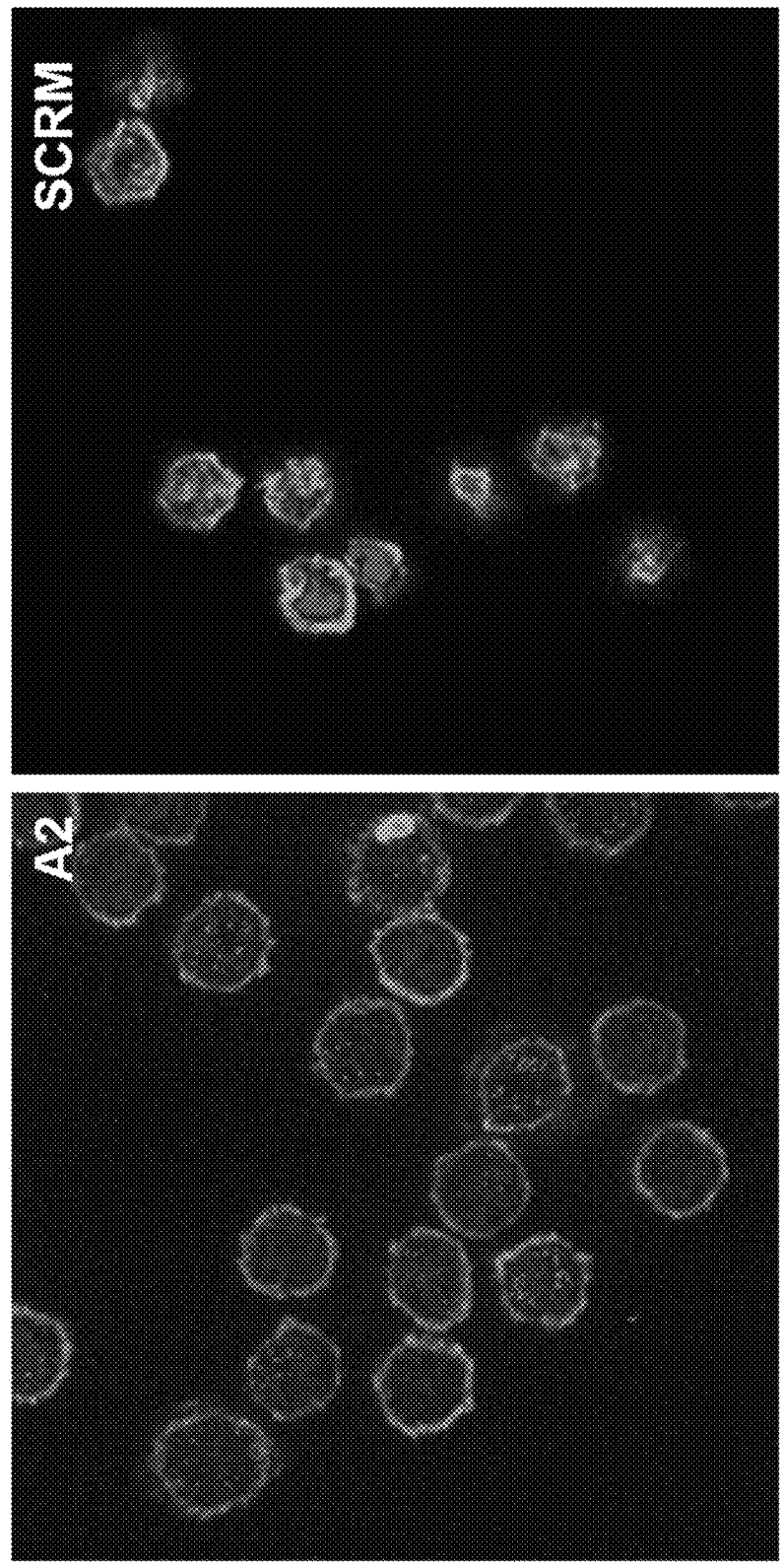

To evaluate the potential of using aptamer A2 to deliver cargo intracellularly, aptamer internalization was investigated next. Monocytes were incubated with aptamer for 10 and 20 minutes and then treated with trypsin to remove aptamer bound to external receptors (FIG. 3D). Remaining aptamer fluorescence was analyzed via flow cytometry. While trypsin treatment did significantly reduce overall fluorescent signal (****p<0.0001), the majority of fluorescent signal remained, indicating that the aptamer was rapidly internalized into cells. Aptamer internalization was further validated by confocal microscopy at 20 minutes after incubation, which revealed aptamer presence in punctate staining patterns within monocytes, consistent with vesicular internalization (FIG. 3F). Last, the monocyte subset to which the aptamer bound was investigated. Monocytes are classified as classical (CD14$^{hi}$CD16$^{lo}$) or non-classical (CD14$^{lo}$CD16$^{hi}$) monocytes, which comprise 70-95% and 2-11% of monocytes, respectively. PBMCs were stained with anti-human CD14 and anti-human CD16 antibodies and observed that aptamer A2 only bound to CD14$^+$ classical monocytes, with no binding to CD16$^+$ monocytes (FIG. 3E).

Figure 4A:
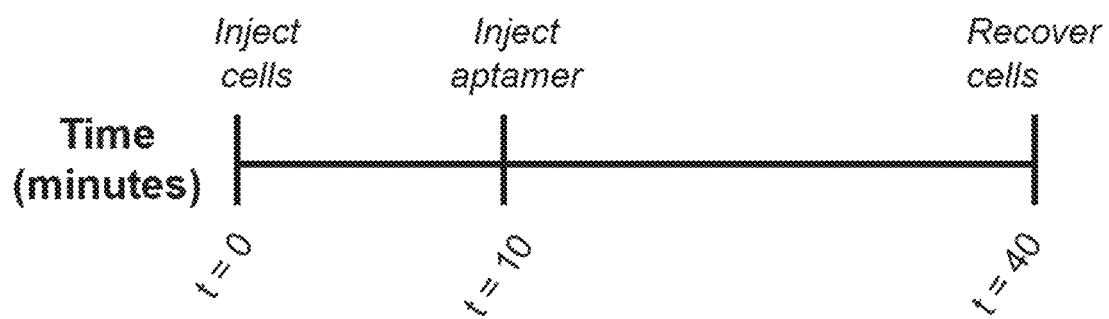
FIGS. 4A-4D: Aptamer A2 retains binding to $CD14^+$ cells in vivo.
Figure 4B:
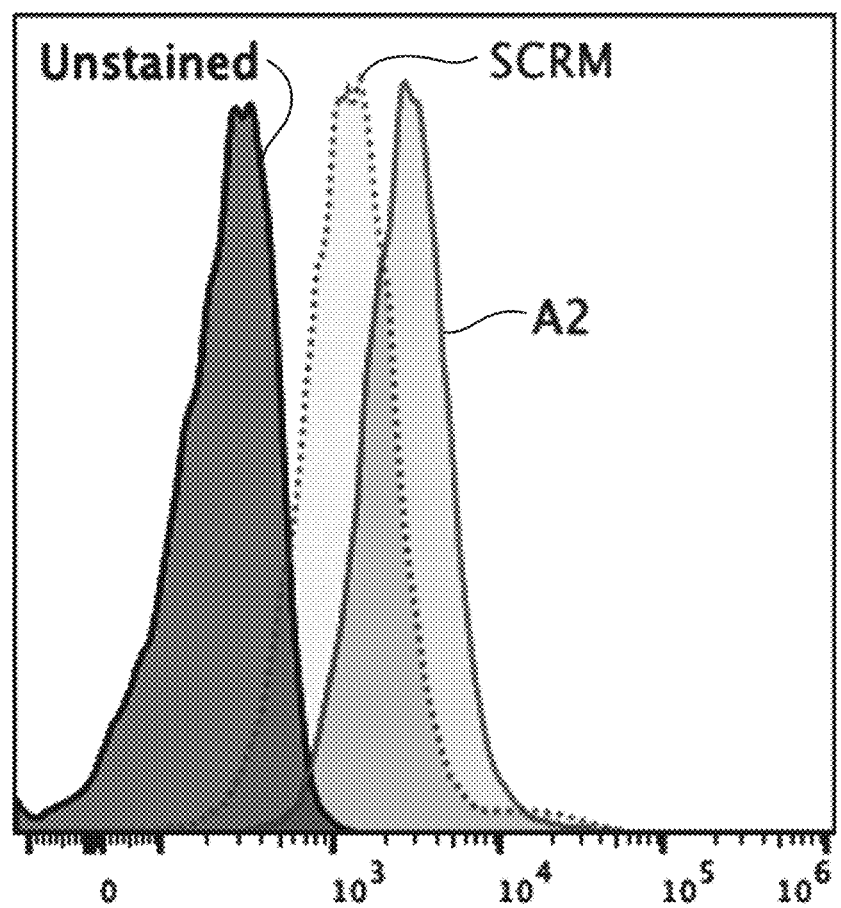
Figure 4C:
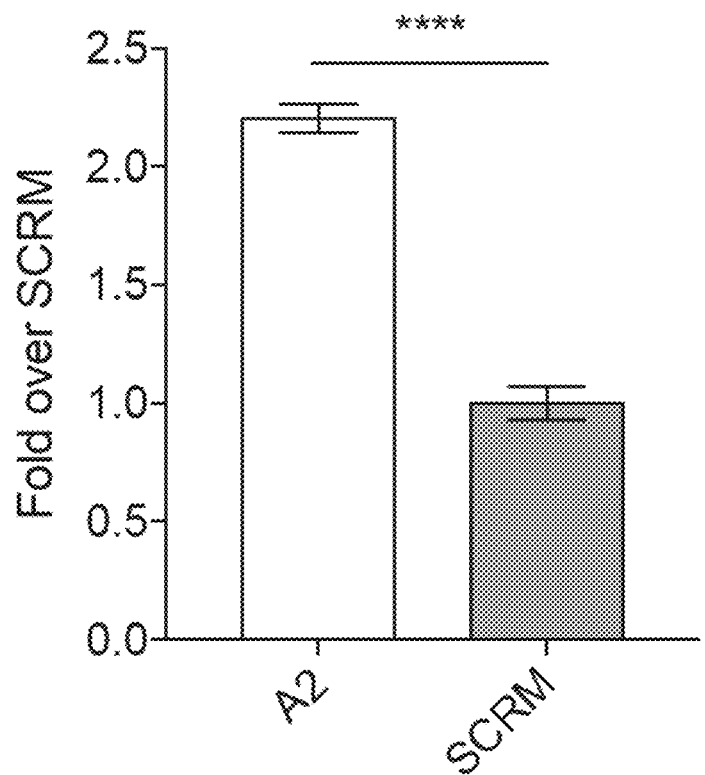
Figure 4D:
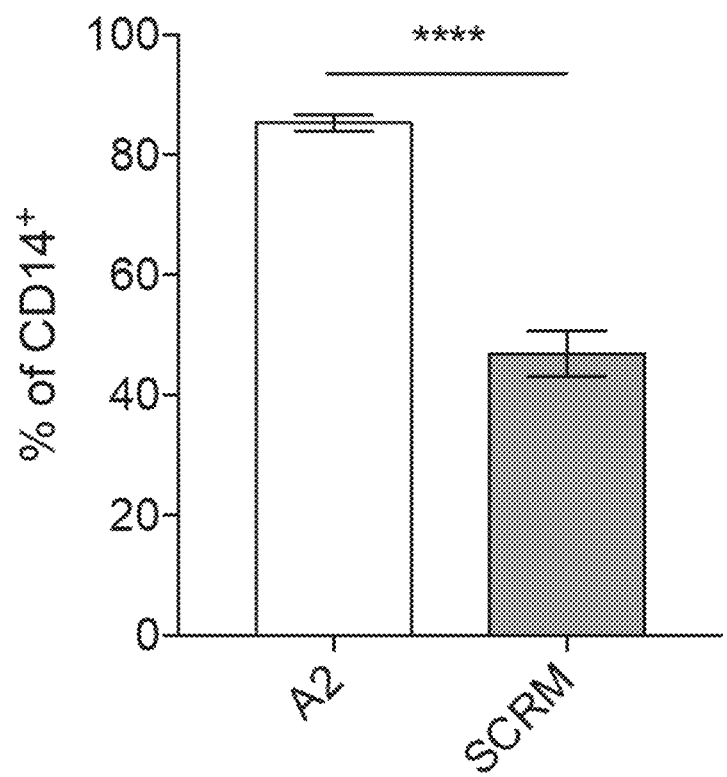
Figure 9A:
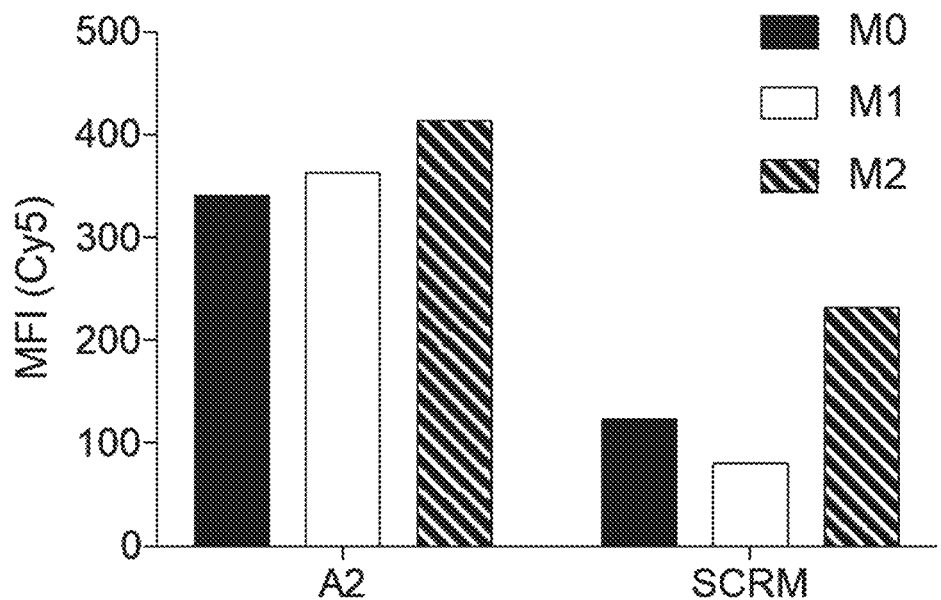
FIGS. 9A-9B: Aptamer A2 binding was assessed against murine macrophages and PBMCs.
Figure 9B:
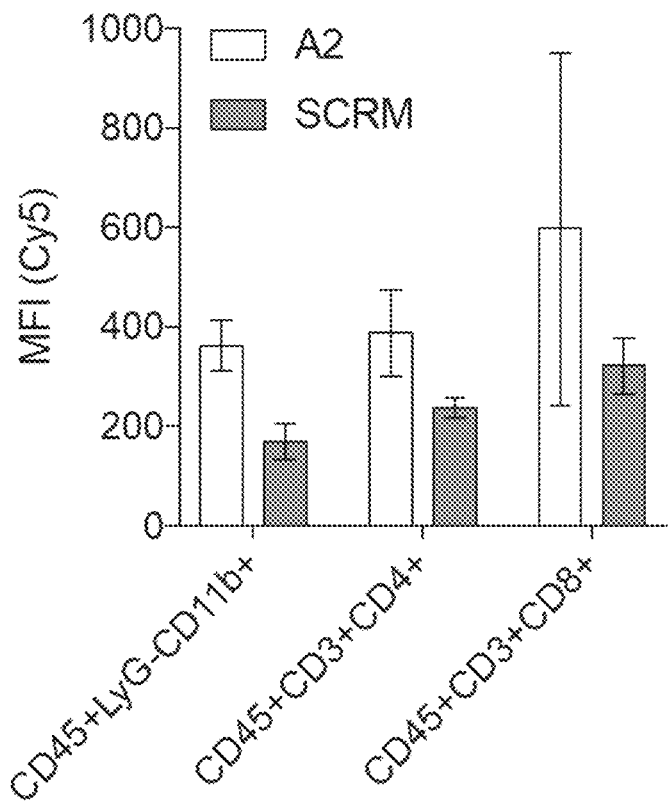

Aptamer A2 retains binding to monocytes in vivo. Given the accessibility of monocytes in the blood, aptamer binding to monocytes was next investigated in vivo. Monocytes targeting was focused on, rather than macrophage targeting due to challenges in developing humanized mouse models, which still suffer from impaired engrafted macrophage function.[28] To determine whether aptamer A2 retained binding to monocytes in vivo, human monocytes cells and aptamer (either A2 or SCRM) were injected intraperitoneally (i.p.) into NOD-SCID gamma (NSG) mice, as previously described (FIG. 4A).[29] NSG mice were used because they are immunodeficient, allowing for engraftment of human cells. Cells were recovered by peritoneal lavage and stained with human anti-CD14 antibody. Aptamer A2 retained binding to CD14$^+$ cells over a SCRM control (****p<0.0001) (FIGS. 4B-4D). However, it was noted that there was some binding to an unidentified CD14$^-$ cell population; without wishing to be bound by theory, it was hypothesized that this could be due to nonspecific charge interactions of DNA oligonucleotides with cells. In vitro, significant binding was not observed to murine macrophages or PBMCs (FIG. 9).

Figure 8C:
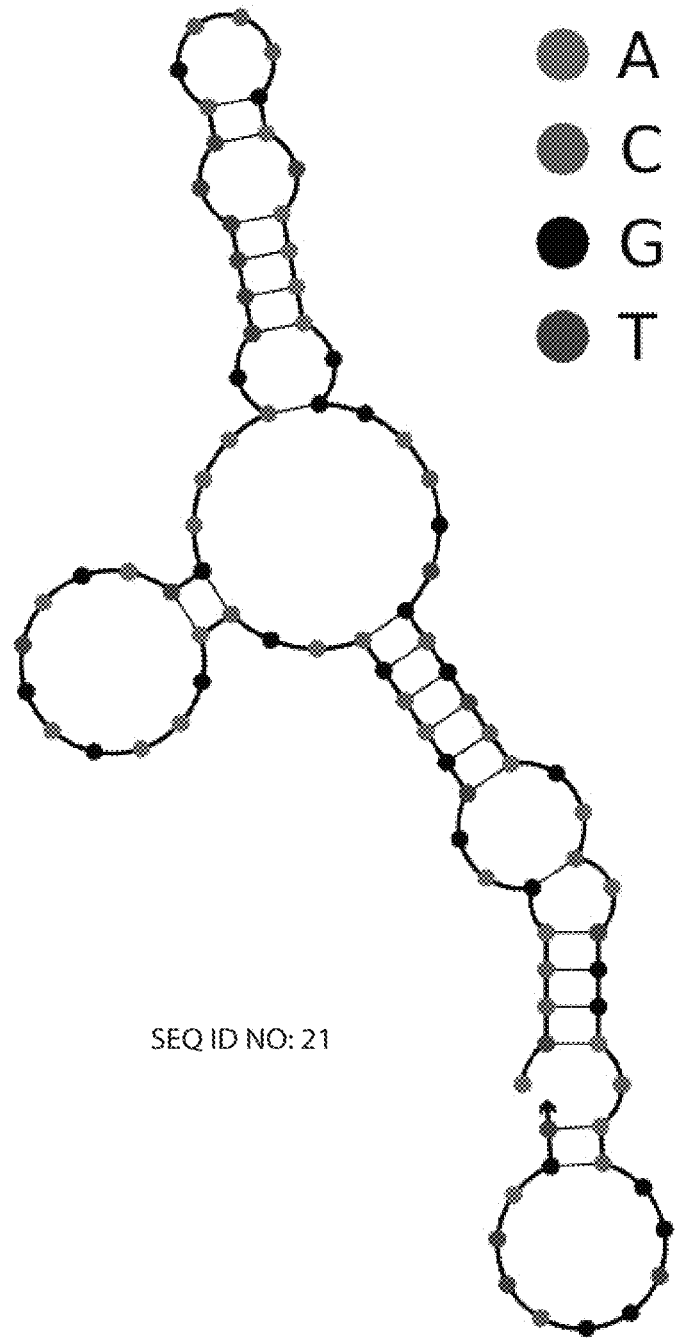

In this example, identification and characterization of the binding behavior of aptamer A2 to human monocytes and macrophages has been completed. Previously, improved therapeutic efficacy was demonstrated with a murine TAM-targeted peptide, M2pep, to deliver a pro-apoptotic peptide to M2-like TAMs, reducing TAM populations and extending survival in tumor bearing mice.[17] However, M2pep did not bind human M2 macrophages, prompting the search for an aptamer that could bind human M2-like TAMs. The original strategy was to identify an aptamer that could preferentially target M2-like macrophages because of their resemblance to TAMs, and to bypass tissue resident macrophages (M0-like macrophages). Individual aptamer sequences were ordered and assessed for binding against human macrophages. Although aptamer A1 represented 20% of total sequences, it did not bind to human macrophages (FIG. 8). Propagation of parasitic sequences is not uncommon for the SELEX process and could perhaps be explained by PCR amplification bias.[30] Aptamer A2 had an abundance of 3% in the final pool but did not have sequence similarities to other identified motifs.

Aptamer A2 did bind M2-like macrophages with high affinity, but also bound monocytes and M0-like macrophages, albeit with lower affinity. While the $K_d$ of aptamer binding to M1-like macrophages was similar to the $K_d$ to M0- and M2-like macrophages, the maximum binding was lower, indicating lower receptor density on the cell surface. Aptamer binding to monocytes and M0-like macrophages was initially surprising because these cell populations were used as negative selection screens, and aptamers that bound these cells should consequently have been removed during the selection process. However, consideration about receptor overlap between macrophage phenotypes and precursors could explain this binding.[16] M0- and M2-like macrophages are more similar to each other than to M1-like macrophages and have a high degree of receptor overlap. Aptamer binding to human monocytes was next characterized. Despite use as negative selection screens, aptamer A2 bound with comparable affinity to monocytes and M0- and M2-like macrophages. This could perhaps be due to high receptor overlap, such as CCR2, CX3CR1, and CSF-1R. This finding further demonstrated the complexity of macrophage polarization, and how it is best viewed as a continuum rather than as a binary outcome.[15,31] Overall, in vitro polarization provided an incomplete picture of macrophage functional states, which are complicated and require precise environmental cues that cannot be replicated in vitro. Another likely reason that the aptamer bound to negative selection cells is because of the use of several donors for selection. Originally, this strategy was chosen to enable universal application despite variabilities across donor receptor expression. However, donor characteristics (age and gender) can significantly impact cytokine response, ultimately impacting macrophage polarization, receptor expression, and phenotype of the cells.[27] Because different donors have different degrees of receptor expression, the use of multiple, random donors ultimately impacted receptor expression and thus aptamer selection.

Figure 10A:
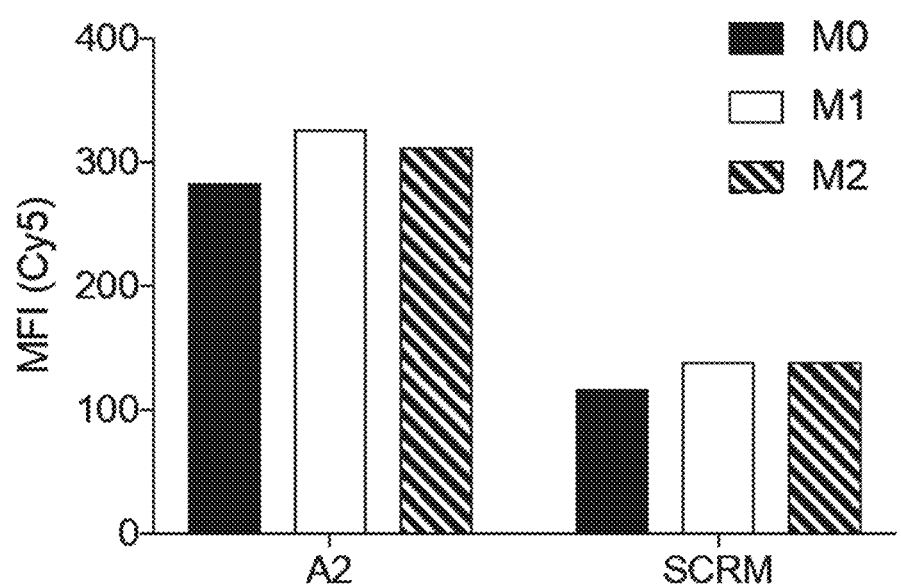
FIGS. 10A-10C: Aptamer A2 binding to THP-1 macrophages and THP-1 and U937 monocytes.
Figure 10B:
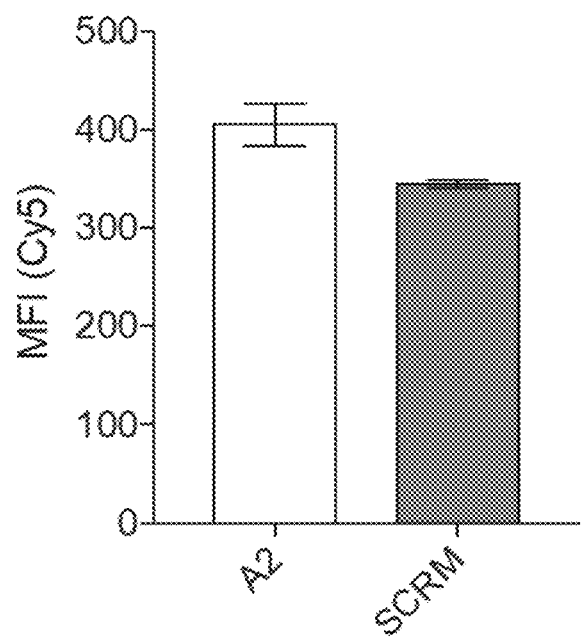
Figure 10C:
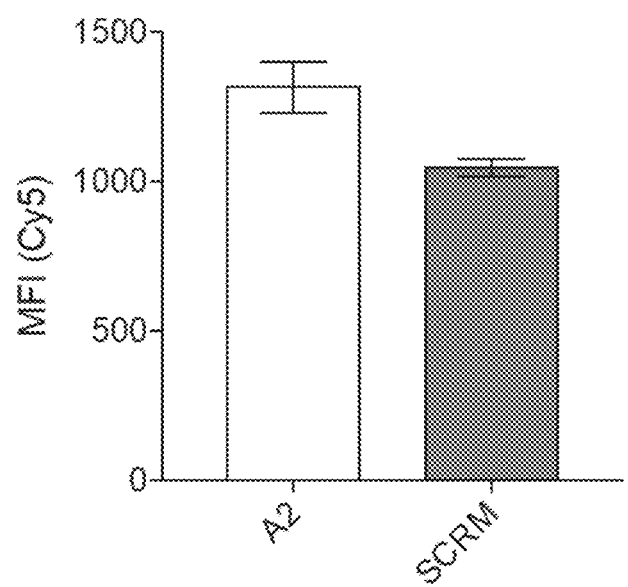
Figure 11A:
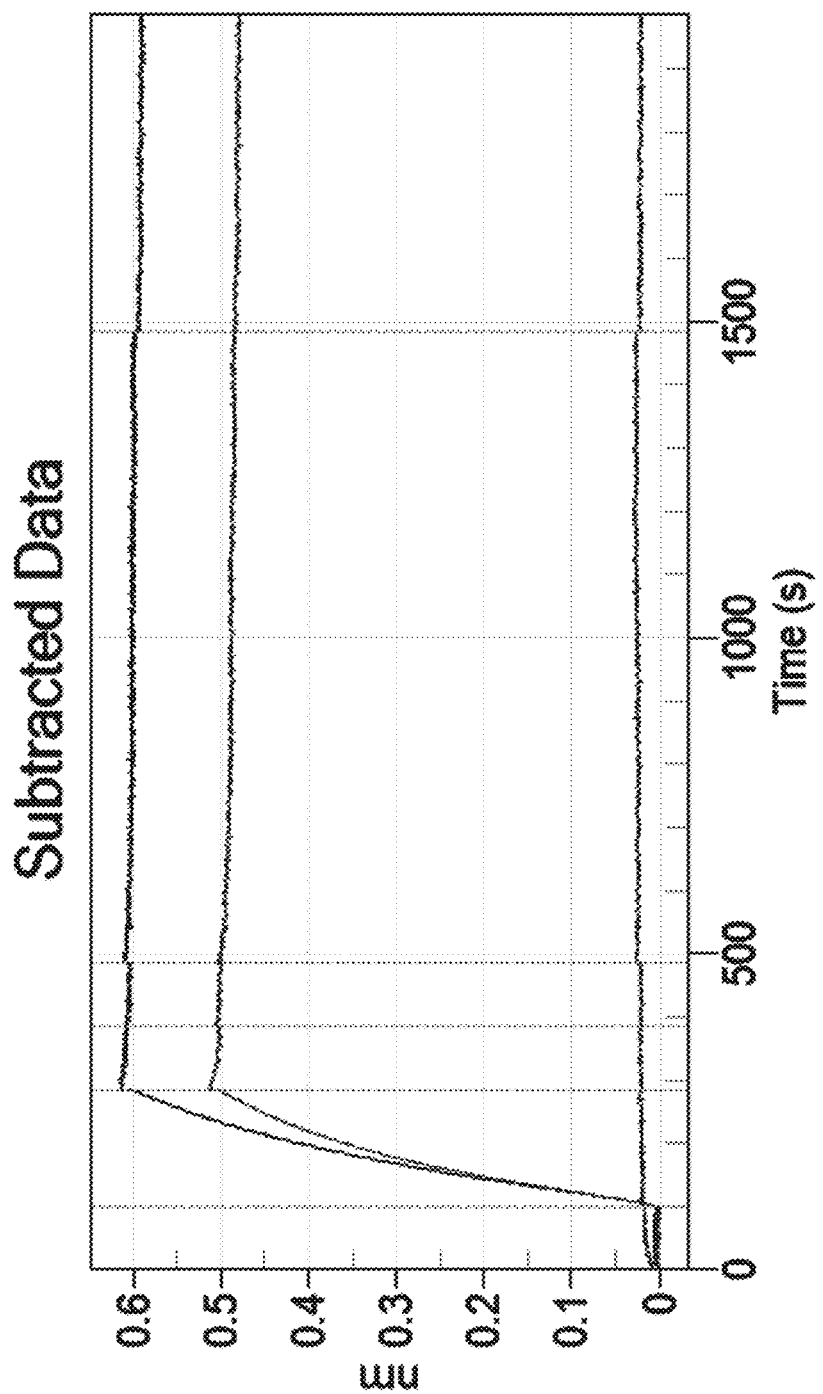
FIGS. 11A-11B: Aptamer binding to CD14 protein by surface plasma resonance.
Figure 11B:
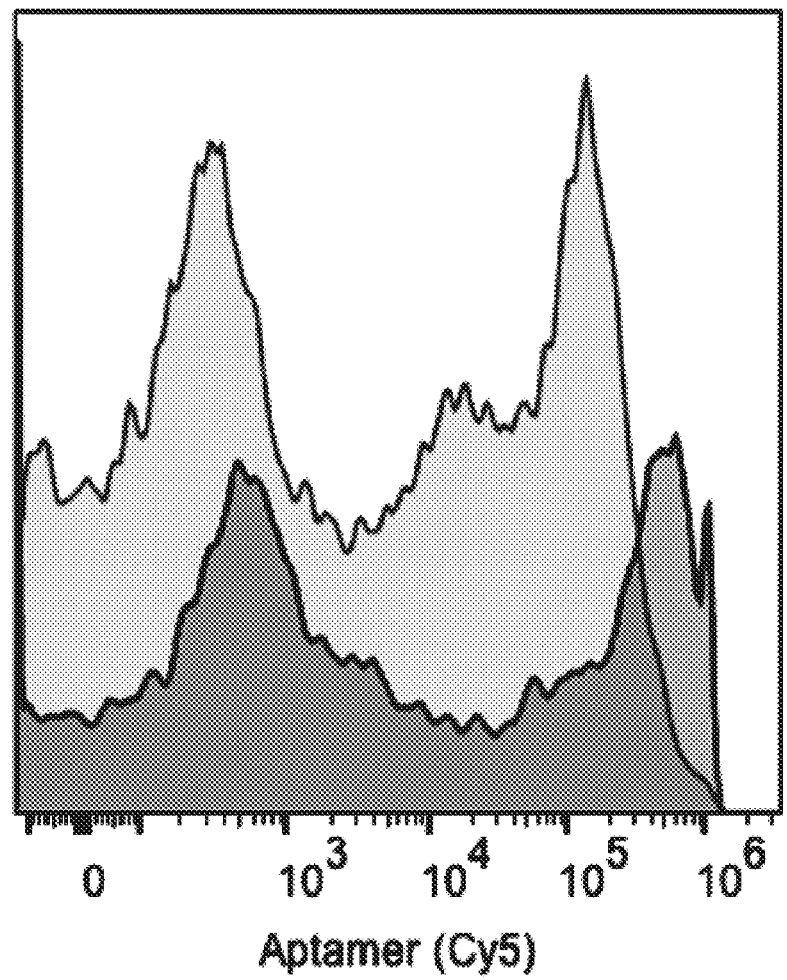
Figure 12A:
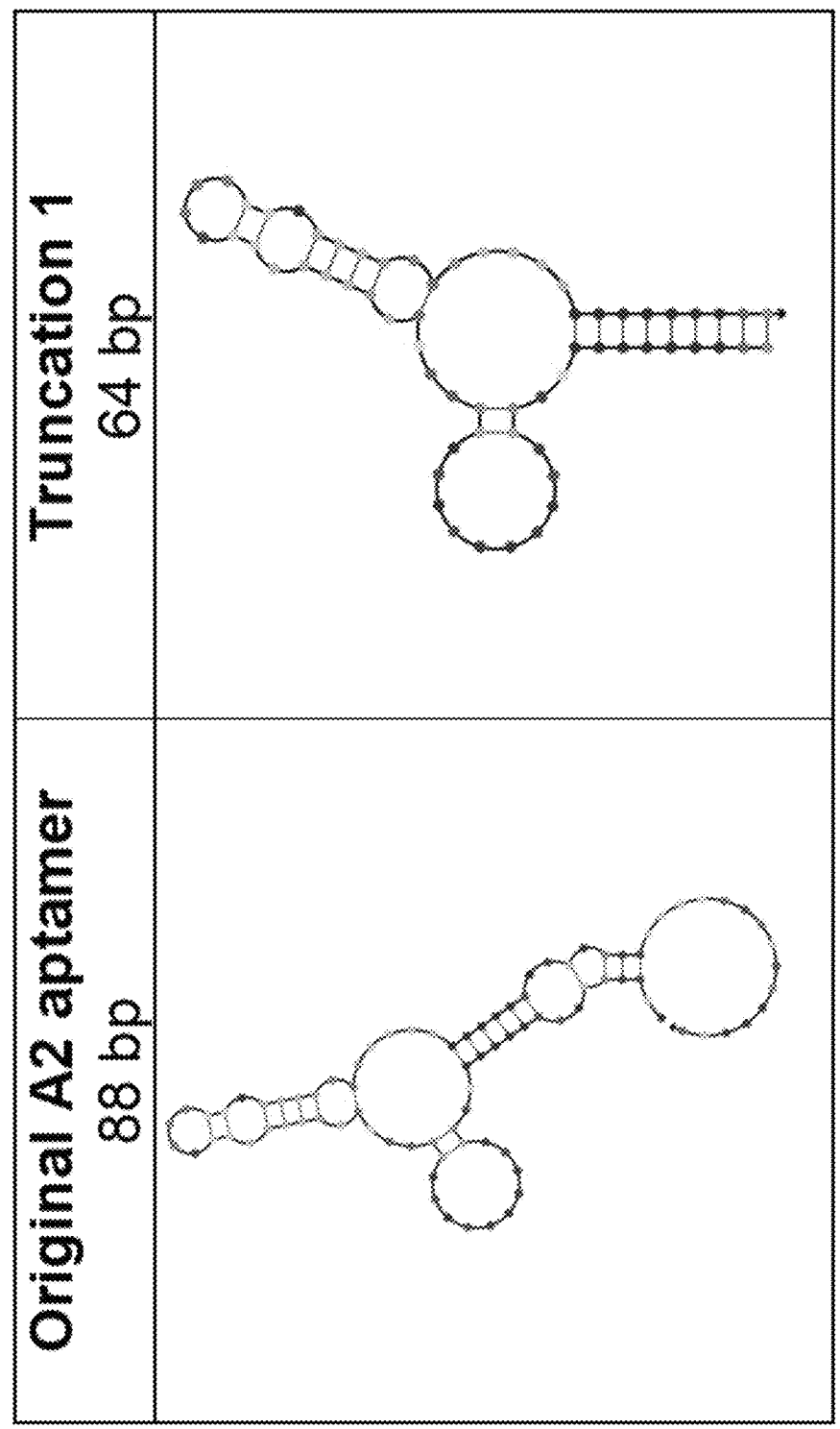
FIGS. 12A-12C Aptamer Structure and Binding.
Figure 12A:
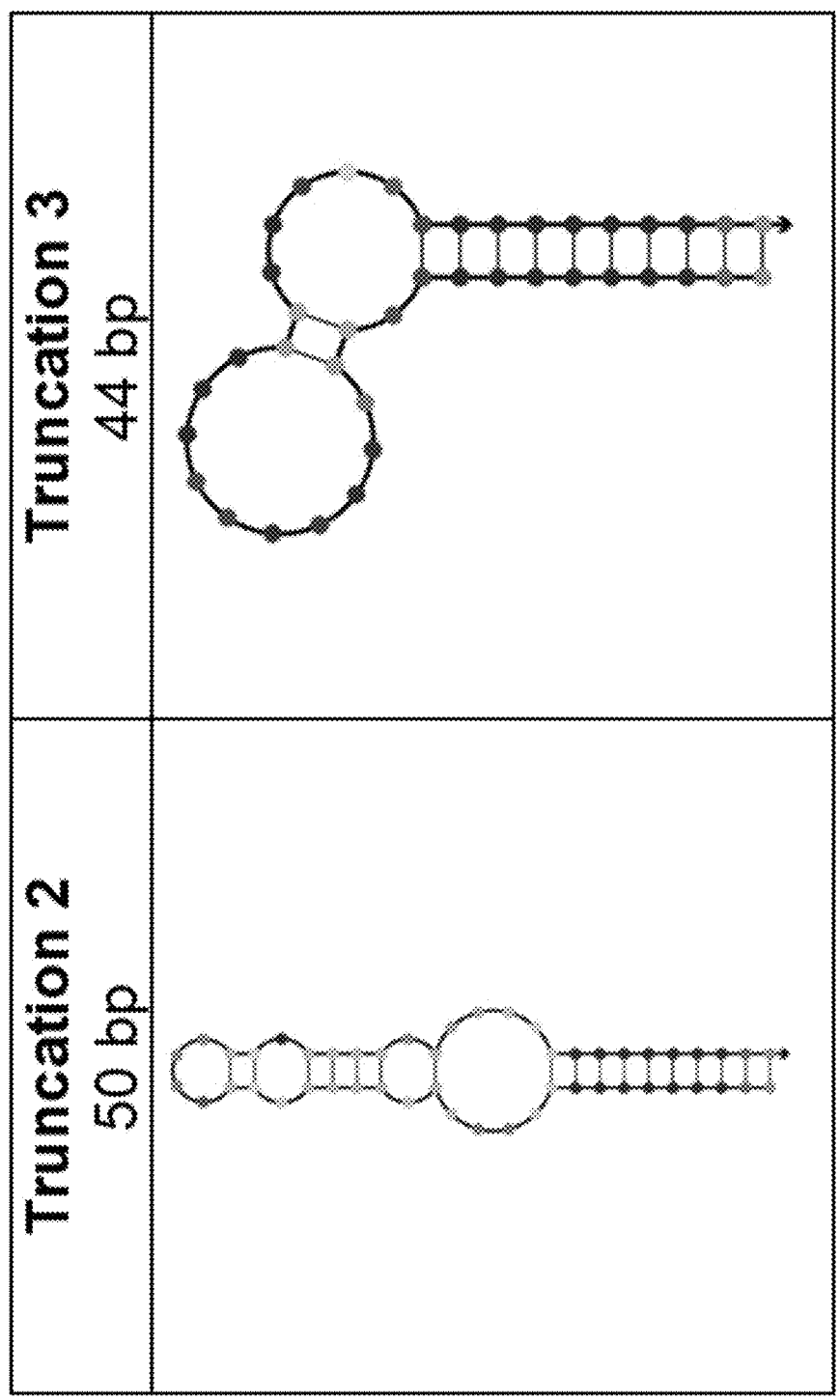
Figure 12B:
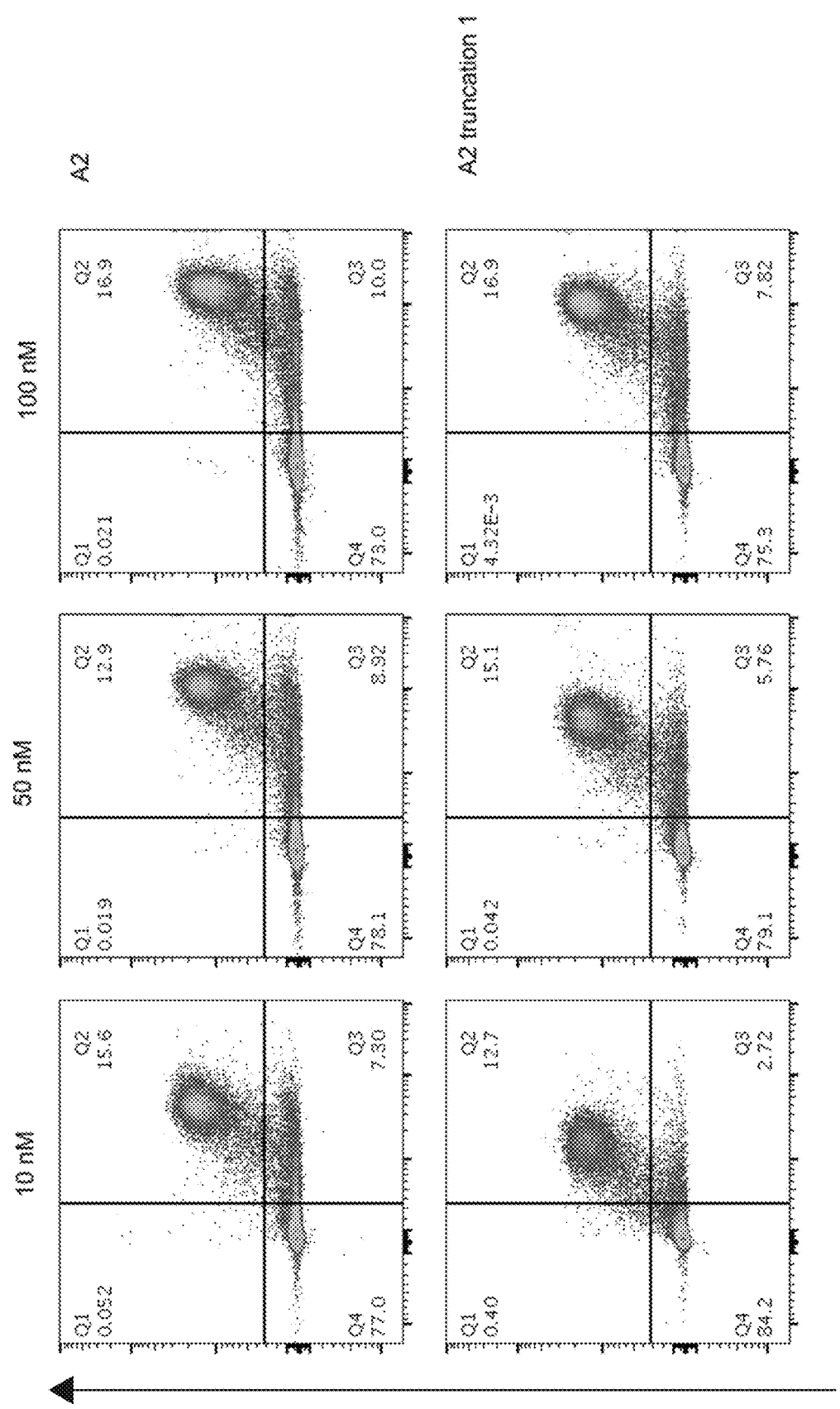
Figure 12B:
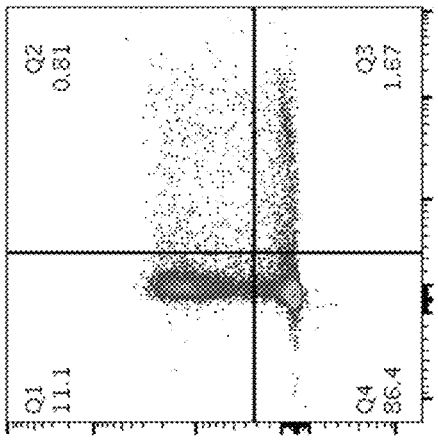
Figure 12B:
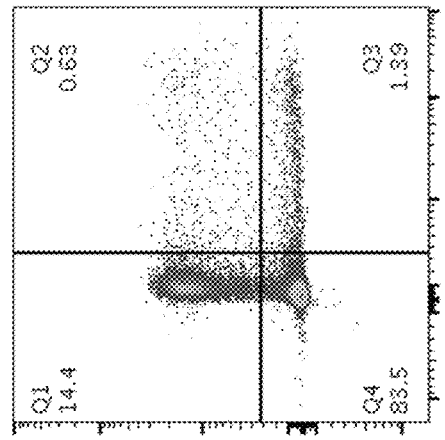
Figure 12B:
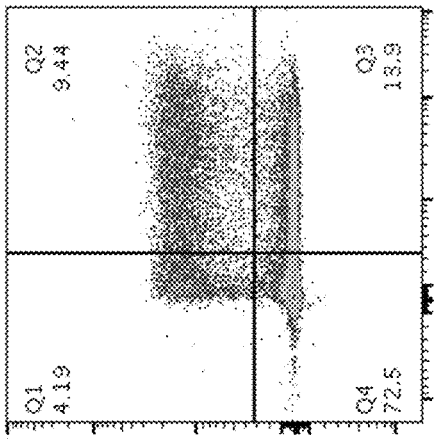
Figure 12B:
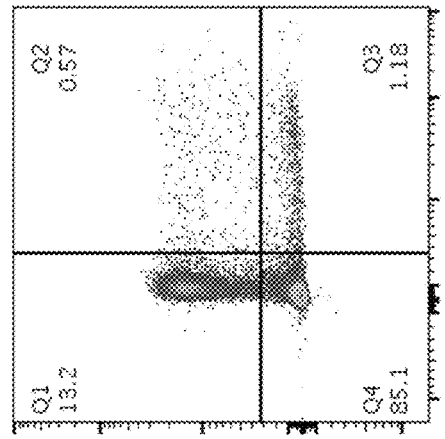
Figure 12B:
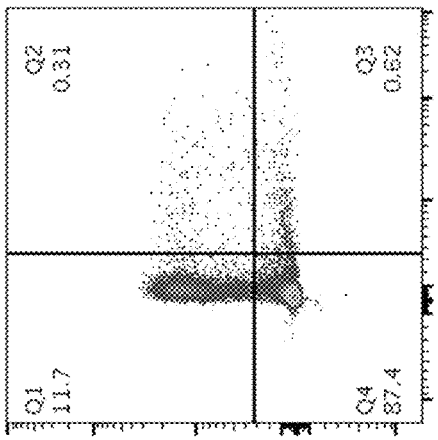
Figure 12B:
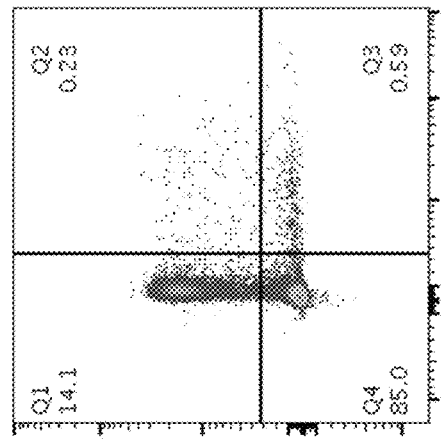
Figure 12B:
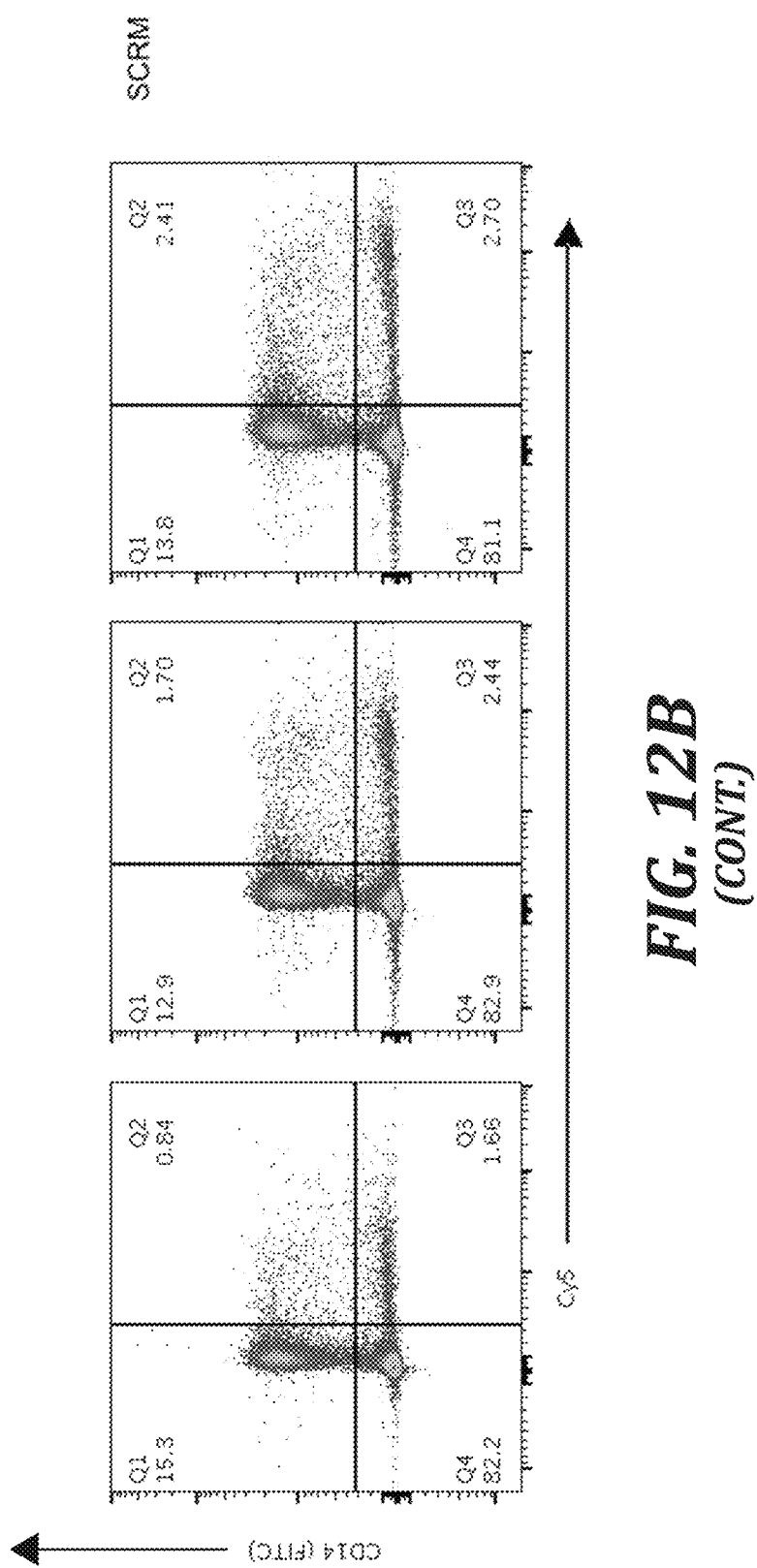
Figure 12C:
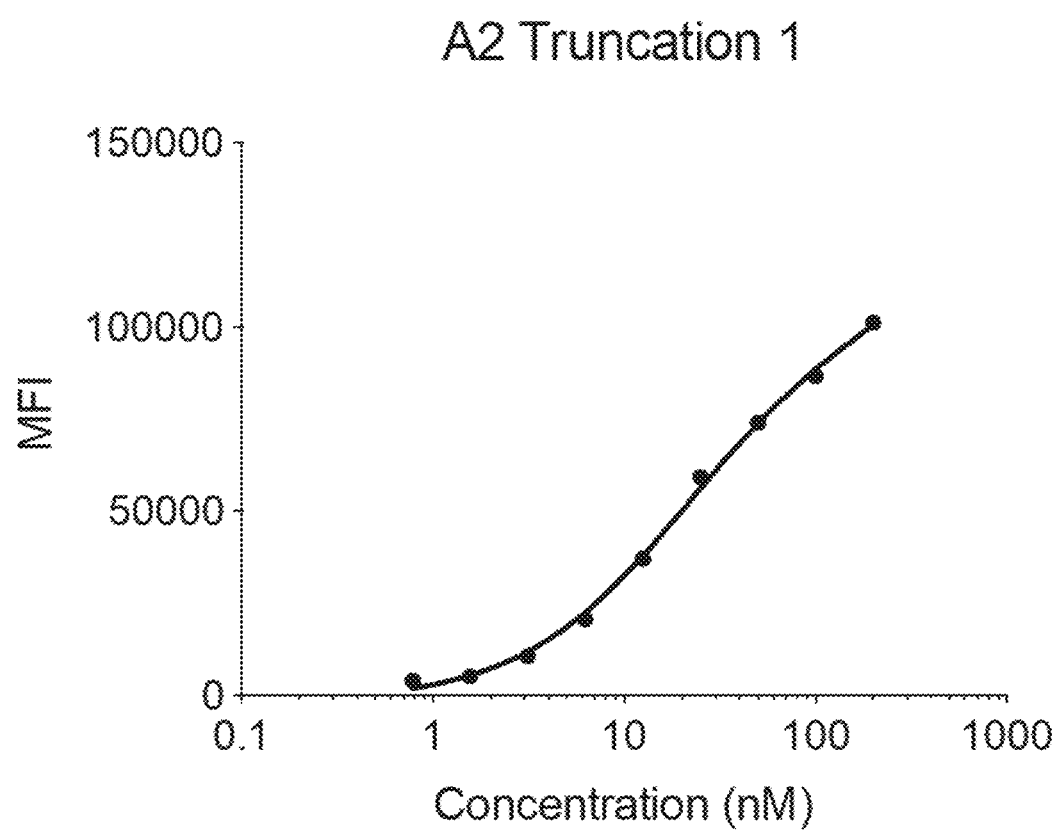

It was also sought to identify the receptor to which the aptamer bound, but initial pull-down attempts were unsuccessful. One barrier of pull-down assays was that the method required extremely high cell numbers.[32] Due to the high cost of isolating human monocytes, it was attempted to identify an immortalized cell line to which the aptamer bound. However, aptamer A2 did not bind significantly to murine macrophages or PBMCs, or the immortalized monocyte THP-1 or U937 cell lines (FIG. 10). Based on A2 binding behavior to monocytes, it was hypothesized that the aptamer bound to the CD14 receptor, which is expressed by both monocytes and macrophages. Aptamer binding to purified CD14 protein was investigated by biolayer interferometry (BLI) and by transfecting Jurkat cells, a T-cell line, to express CD14. However, no significant binding over SCRM was observed (FIG. 11).

Lastly, in vivo binding to monocytes was investigated, given the accessibility of monocytes and the challenges in establishing humanized mouse models to support human macrophage populations. Monocytes are circulating blood cells, whereas macrophage engraftment would require tumor re-population, sufficient aptamer pharmacokinetics and stability to remain intact following injection, and adequate aptamer-tumor localization and targeting. While humanized mouse models have made impressive advancements in replicating human lymphoid cells, the engraftment of human myeloid cells in commercially available immunodeficient mice is technically challenging, costly, and time consuming.[33] Furthermore, engrafted cells have impaired macrophage function and do not exactly replicate their behavior in tumors.[28] Aptamer targeting in the intraperitoneal (i.p.) cavity of mice, while not exactly replicating an intravenous model, demonstrated binding at relevant physiologic conditions.[29]

Because aptamer A2 binds to both M0- and M2-like macrophages, it holds potential for in vivo or in vitro applications aimed at monocytes, such as column selection from PBMCs or drug delivery to monocytes in disease states. Indeed, it was found that the majority of A2 is rapidly internalized within 10 minutes (FIG. 3D), which could enable efficient intracellular drug delivery. Because monocytes are macrophage precursors, the ability to specifically target these cells could have large implications for future cancer therapies. Researchers have investigated blocking monocyte recruitment to tumors, which temporarily inhibited tumor growth, and have employed monocytes for drug delivery to immune privileged sites (e.g., central nervous system).[34-36] Monocytes are also implicated in viral infection, such as Zika and influenza A, and new therapies could utilize in situ targeting for drug delivery or depletion.[37,38] Additionally, aptamer A2 could be applied to magnetic columns for monocyte capture and subsequent release, isolating CD14$^+$ monocytes from PBMCs; this application has been reported previously for CD8$^+$ T cell isolation.[21] Use of this aptamer for column selection could decrease cost, which could have significant impact as the field moves toward engineered macrophages for adoptive therapies.[7,39,40] Furthermore, A2 could be used to isolate a highly pure population of classical CD14$^+$ monocytes, which offer distinct functional properties (e.g., differentiation, receptor expression, migration) compared to CD16$^+$ monocytes.[41,42] This pure starting populations can provide more homogenous results compared to isolations with mixed CD14$^+$ and CD16$^+$ monocytes.

For use in vivo, further modifications would be necessary to extend aptamer circulation time and stability.[43,44]

Experimental Procedures

Oligonucleotides and cell-SELEX. All oligonucleotides were synthesized by Integrated DNA Technologies (IDT). The ssDNA library (~ 10$^{16}$ individual sequences) used in the cell-SELEX process was purchased from IDT and consisted of a 52 base-pair (bp) random sequence flanked by two 18 bp constant regions. The primers used for library amplification are as follows: forward 5'-FAM-ATCCAGAGTGACGCAGCA-3' (SEQ ID NO:11) and reverse 5'-biotin-ACTAAGCCACCGTGTCCA-3' (SEQ ID NO:12). The SELEX protocol was adapted from a previously reported method.[20] A schematic of the SELEX procedure is shown in FIG. 1, including cell number, washes, incubation time, and aptamer concentration. Broadly, positive selection was performed against plated human macrophages polarized to an M2-like phenotype. Bound aptamers were extracted by lifting cells with a cell scraper and heating the suspension to 95° C. to denature DNA and separate aptamers from cells. The supernatant containing aptamer sequences was collected, and protein (BSA or DHS) and tRNA (100 µg/mL) was added. For negative selection, these sequences were then bound against monocytes or plated human macrophages polarized to an M0-like phenotype. The supernatant containing unbound aptamer sequences was collected and amplified by PCR using Phusion™ High Fidelity DNA Polymerase (NEB) with forward and reverse primers. Strand separation was performed with High Capacity Neutravidin Agarose Resin (Thermo), and the FAM-labeled ssDNA aptamer pool was used in the next round.

NGS and data analysis. The resulting ssDNA pools from each round of SELEX were PCR amplified using the MiSeq Reagent Kit v2 (300 cycles) and MiSeq System (Illumina) according to manufacturer's instructions. Exported FASTA files were analyzed with FASTAptamer v1.0.3, as described previously.[21] Specifically, FASTAptamer-Count was used to rank sequences by reads per million. FASTAptamer-Compare was used to calculate enrichment of sequences between inputted rounds. Neighbor joining phylogenetic trees were constructed for the top 100 sequences from rounds 6-9 using Ninja v1.2.2 and visualized by FigTree v1.4.3. Consensus sequence and conserved motifs across the top 50-100 sequences from each round were predicted using MEME Suite v4.12.0. The NUPACK web application was used to predict secondary structures.

Cell culture and PBMC isolation. Human PBMCs were isolated from Leukocyte Reduction System cones (Bloodworks Northwest) using Ficoll-Paque (GE) density gradient centrifugation. Monocytes isolated using the Monocyte Isolation Kit II (Miltenyi) or Pan Monocyte Isolation Kit (Miltenyi). Human macrophages were cultured by plating monocytes in RPMI 1640 (Gibco) supplemented with 20% DHS (R&D), 1% PenStrep (ThermoFisher), and 25 ng/mL M-CSF (R&D). On day 4, additional plating media was added. On day 7, macrophages were polarized to an M0 (25 ng/mL M-CSF), M1 (50 ng/mL IFN-γ (R&D)+10 ng/mL LPS (InvivoGen)), or M2 (20 ng/mL IL-4 (R&D)) phenotype for 24-48 hours prior to use. Phenotype was validated via flow cytometry with human anti-CD64 and anti-HLA-DR antibodies (M1 markers) and human anti-CD36 and anti-CD180 antibodies (M2 markers). U937 and THP-1 monocytes were obtained from ATCC. THP-1 macrophages were plated using PMA (Sigma), and polarized to M0, M1, and M2 phenotype as above.

Generation of murine BMDM and PBMC. All animal experiments were approved by the Institutional Animal Care and Use Committee at the University of Washington and were conducted in accordance with use and regulations. Murine bone marrow derived macrophages (BMDM) were generated as previously described.[17] Briefly, the femur and tibia from 6-8 week Balb/c mice were flushed of bone marrow and cells were cultured in the same media as human macrophages (described above) supplemented with 25 ng/mL murine M-CSF (Miltenyi). On day 4, additional media supplemented with 25 ng/mL murine M-CSF was added. On day 7, macrophage were polarized to an M0 (25 ng/mL murine M-CSF), M1 (50 ng/mL IFN-γ (R&D)+10 ng/mL LPS (InvivoGen)) or M2 (20 ng/mL IL-4 (R&D)) phenotype 24-48 hours prior to use. PBMCs were isolated via terminal blood draw from the vena cava using Ficoll-Paque (GE) density gradient centrifugation.

Antibodies and flow cytometry. For binding studies involving antibodies, cells were blocked with FcBlock™ (human (Miltenyi) or murine (BioLegend)) according to manufacturer's instructions. The following dyes and antibodies were used to stain cells: Zombie Violet™ (1:500 in 100 μL 10-6 cells, BioLegend), Zombie Yellow™ (1:500 in 100 μL 10-6 cells, BioLegend), SuperBright 702 anti-human CD56 (1:100, ThermoFisher), SuperBright 600 anti-human CD19 (1:20, ThermoFisher), PE anti-human CD3 (1:100, BioLegend), FITC anti-human CD14 (1:200 BioLegend), PE-Cy7 anti-human CD14 (1:40, Fisher), APC/Cy7 anti-mouse CD45 (1:100, Miltenyi), eFluor™ 450 anti-mouse CD3 (1:100, BioLegend), Alexa Fluor® 594 anti-mouse CD4 (1:20, BioLegend), FITC anti-mouse CD8 (1:1000, BioLegend), PE anti-mouse CD11b (1:40, BioLegend), FITC anti-mouse Ly6G (1:40, BioLegend), PE anti-mouse CD64 (1:20, BioLegend), FITC anti-human HLA/DR (1:20, BioLegend), FITC anti-human CD36 (1:20, BioLegend), APC anti-human CD206 (1:100, BioLegend), DAPI (300 nM), Phalloidin-FITC (1:100, Invitrogen). OneComp™ eBeads (Invitrogen) were used to prepare single-color controls for compensation if needed. Stained samples were analyzed with a MACSQuant® Analyzer 10 (Miltenyi) or Attune™ NxT (Invitrogen) flow cytometer.

Aptamer binding assays. For individual aptamer binding, cells ($0.5\times10^6$) were incubated with 50 nM folded aptamer (in Wash Buffer (WB) supplemented with 10% DHS and 100 μg/mL tRNA) and antibody cocktail for 20-30 min at 4° C. (unless otherwise indicated). Aptamers were ordered with a Cy5-label as it is a brighter fluorophore than FAM/FITC; however, fluorophore labeling has no effect on binding. All aptamer binding was compared to a nonspecific aptamer sequence control. After binding, cells were washed twice in 200 μL of WB supplemented with 1% BSA. Stained cells were fixed in 200 μL of WB with 1% BSA and 0.5% PFA before analysis via flow cytometry. For aptamer internalization assay, monocytes were incubated with the aptamer at 50 nM at 37° C. for 10, 20 and 30 minutes, washed with 500 μL WB, and external receptors were cleaved with 0.25% trypsin at 37° C. for 3 minutes. For macrophage binding assays, plated cells ($1-2\times10^6$) were incubated with 50 nM aptamer, washed with PBS without ions, and lifted with Versene™ (Gibco) for 20 min at 4° C. or TrypLE™ (Fisher) for 30 min at 37° C. Cells were processed for analysis via flow cytometry as above. GraphPad Prism 7.0 was used to calculate the total binding dissociation constant. BLI studies were conducted on a FortdBio Octet Red96 instrument, as previously described.[21]

Droplet digital PCR. Plated cells ($1-2\times10^6$) in a 6-well TC plate (Corning) were washed twice with WB, incubated with 50 nM (individual) or 200 nM (round binding) folded aptamer (in WB supplemented with 10% DHS and 100 μg/mL tRNA) for 30 min at 4° C., and washed five times with WB supplemented with BSA. Cells were lysed and DNA was recovered via DNeasy™ kit (Qiagen) according to manufacturer's instructions. DNA was quantified using a Qubit™ (Thermo) and serially diluted in molecular water. DNA and primers (extended aptamer and reference 12S ribosomal RNA gene) were added to EVA GREEN™ Master Mix (Biotium) and analyzed via ddPCR according to manufacturer's instructions.

Imaging. For monocyte confocal assays, coverslips were coated with 10 μg/mL poly-D-lysine at 37° C. for 2 hours. Cells were bound with 50 nM aptamer and plated onto coverslips by centrifuging at 2,000 rpm for 10 minutes. Cells were fixed in 4% PFA, stained with Phalloidin-FITC (1:100) and DAPI (300 nM), and mounted onto glass slides. For macrophage confocal assays, coverslips were coated with 45 μg/mL collagen for 1 hour at room temperature. Monocytes were plated onto coverslips and cultured into macrophages. After polarization, macrophages were bound with 100 nM aptamer, fixed, stained, and covered. Images were taken on a Leica SP8X. Humans tumors were obtained from the Washington Cancer Consortium Breast Specimen Repository and Registry in accordance with guidelines established by the University of Washington Institutional Review Board. All patient information was de-identified prior to sharing with investigators. Tumors were fixed in 4% PFA overnight and dehydrated via sucrose gradient. Tumors were frozen in OCT and sectioned in 10 m thick sections using a cryosectioner (Leica CM1850). Sections were fixed (4% PFA, 10 min at room temperature), blocked and permeabilized (2% DKS+2% BSA+0.3% Triton-X in TBS, 1 hour at room temperature), and stained with primary antibody overnight at 4° C. in a humidified box. Sections were washed three times in TBS-0.1% Tween (30 minutes each) followed by incubation with secondary antibody and DAPI (1 hour at room temperature). Sections were washed three times in TBS-0.1% Tween, blocked with 50 μg/mL salmon sperm (Invitrogen) for 1 hour at 4° C., and incubated with 1 μM folding aptamer (in WB supplemented with 10% DHS and 100 μg/mL tRNA) for 1 hour at 4° C. Sections were washed three times with TBS-0.1% Tween and covered with coverslip. Images were taken on a Nikon Eclipse™ TI. Images were analyzed on ImageJ version 2.0.0-rc-69/1.52i. A region-of-interest (ROI) was drawn around image areas with aptamer signal; the same ROI was used in A2 and SCRM images. Colocalization was analyzed using the Coloc2 plug-in. Statistical significance was determined based on the Spearman rank correlation in two independent images.

In vivo intraperitoneal binding. Donors were screened for binding prior to monocyte isolation. Monocytes ($1\times10^6$) were injected i.p. into NSG mice (Jackson). After 10 min, aptamer (125 nM A2 or SCRM+625 nM unlabeled NS aptamer) were injected i.p. in WB. After 30 minutes, the mouse was sacrificed by cervical dislocation. Cells were recovered via peritoneum lavage, as described. Recovered cells were incubated with ACK Lysis Buffer (Invitrogen) for 5 min at room temperature and were processed for analysis via flow cytometry.

Statistical analysis. Significance was determined by ANOVA (multiple groups) or a two-tailed student's t-test in Graphpad Prism 7. All flow cytometry analysis was completed using FlowJo.

REFERENCES (1) Kalos, et al. T Cells with Chimeric Antigen Receptors Have Potent Antitumor Effects and Can Establish Memory in Patients with Advanced Leukemia. (2011) *Sci. Transl. Med.* 3(95):95ra73.
(2) Andon, et al. Targeting tumor associated macrophages: The new challenge for nanomedicine. (2017) *Semin. Immunol.* 34:103-113.
(3) Tumeh, et al. PD-1 blockade induces responses by inhibiting adaptive immune resistance. (2014) *Nature* 515:568-571.
(4) Sharma and Allison, The future of immune checkpoint therapy. (2015) *Science* 348:56-61.
(5) McGrath, et al. Early hematopoiesis and macrophage development. (2015) *Semin. Immunol.* 27:379-387.
(6) Klichinsky, et al. Human chimeric antigen receptor macrophages for cancer immunotherapy. (2020) *Nat. Biotech.* 38(8):947-953.
(7) Morrissey, et al. Chimeric antigen receptors that trigger phagocytosis. (2018) Elife 7.
(8) Ngambenjawong, et al. (2017) Progress in tumor-associated macrophage (TAM)-targeted therapeutics. (2017) *Adv. Drug Deliv. Rev.* 114:206-221.
(9) Noy and Pollard, Tumor-associated macrophages: from mechanisms to therapy. (2014) *Immunity* 41:49-61.
(10) Sylvestre et al. Progress on Modulating Tumor-Associated Macrophages with Biomaterials. (2019) *Adv. Mater.* 32(13):e1902007.
(11) Bingle et al. The role of tumour-associated macrophages in tumour progression: implications for new anticancer therapies. (2002) *J. Pathol.* 196:254-265.
(12) Dong et al. Leukocyte-mediated Delivery of Nanotherapeutics in Inflammatory and Tumor Sites. (2017) *Theranostics* 7:751-763.
(13) Zeisberger et al. Clodronate-liposome-mediated depletion of tumour-associated macrophages: a new and highly effective antiangiogenic therapy approach. (2006) *Br. J. Cancer* 95:272-81.
(14) Ries et al. Targeting tumor-associated macrophages with anti-CSF-1R antibody reveals a strategy for cancer therapy. (2014) *Cancer Cell* 25:846-859.
(15) Martinez and Gordon, The M1 and M2 paradigm of macrophage activation: time for reassessment. (2014) *F1000Prime Rep.* 6:13.
(16) Mantovani et al. Macrophage polarization: tumor-associated macrophages as a paradigm for polarized M2 mononuclear phagocytes. (2002) *Trends Immunol.* 23:549-555.
(17) Cieslewicz et al. Targeted delivery of proapoptotic peptides to tumor-associated macrophages improves survival. (2013) *Proc. Natl. Acad. Sci. USA* 110:15919-15924.
(18) Keefe et al. Aptamers as therapeutics. (2010) *Nat. Rev. Drug Discov.* 9:537-550.
(19) Chen et al. The isolation of an RNA aptamer targeting to p53 protein with single amino acid mutation. (2015) *Proc. Natl. Acad. Sci. USA* 112:10002-10007.
(20) Sefah et al. Development of DNA aptamers using Cell-SELEX. (2010) *Nat. Protoc.* 5:1169-1185.
(21) Kacherovsky et al. Traceless aptamer-mediated isolation of CD8(+) T cells for chimeric antigen receptor T-cell therapy. (2019) *Nat. Biomed. Eng.* 3:783-795.
(22) Nikitina et al. Monocytes and Macrophages as Viral Targets and Reservoirs. (2018) *Int. J. Mol. Sci.* 19(9): 2821.
(23) Alam et al. FASTAptamer: A Bioinformatic Toolkit for High-throughput Sequence Analysis of Combinatorial Selections. (2015) *Mol. Ther. Nucleic Acids* 4:e230.
(24) Bailey et al. MEME SUITE: tools for motif discovery and searching. (2009) *Nucl. Acids Res.* 37:W202-W208.
(25) Taylor et al. Droplet Digital PCR versus qPCR for gene expression analysis with low abundant targets: from variable nonsense to publication quality data. (2017) *Sci. Rep.* 7:2409.
(26) Sica and Mantovani, Macrophage plasticity and polarization: in vivo veritas. (2012) *J. Clin. Invest.* 122:787-795.
(27) Siegel et al. Phenotype, donor age and gender affect function of human bone marrow-derived mesenchymal stromal cells. (2013) *BMC Med.* 11:146.
(28) Yong et al. Humanized Mice as Unique Tools for Human-Specific Studies. (2018) *Arch. Immunol. Ther. Exp.* (Warsz) 66:245-266.
(29) Mallikaratchy et al. A multivalent DNA aptamer specific for the B-cell receptor on human lymphoma and leukemia. (2011) *Nucl. Acids Res.* 39:2458-69.
(30) Acinas et al. PCR-induced sequence artifacts and bias: insights from comparison of two 16S rRNA clone libraries constructed from the same sample. (2005) *Appl. Environ. Microbiol.* 71:8966-8969.
(31) Mantovani et al. The chemokine system in diverse forms of macrophage activation and polarization. (2004) *Trends Immunol.* 25:677-686.
(32) Wang et al. Selection and characterization of DNA aptamer against glucagon receptor by cell-SELEX. (2017) *Sci. Rep.* 7:7179.
(33) Sippel et al. Human hematopoietic stem cell maintenance and myeloid cell development in next-generation humanized mouse models. (2019) *Blood Adv.* 3:268-274.
(34) Hou et al. Accessing neuroinflammation sites: Monocyte/neutrophil-mediated drug delivery for cerebral ischemia. (2019) *Sci. Adv.* 5:eaau8301.
(35) Qian et al. CCL2 recruits inflammatory monocytes to facilitate breast-tumour metastasis. (2011) *Nature* 475: 222-225.
(36) Olingy et al. Monocyte heterogeneity and functions in cancer. (2019) *J. Leukoc. Biol.* 106:309-322.
(37) Hou et al. Viral infection triggers rapid differentiation of human blood monocytes into dendritic cells. (2012) *Blood* 119:3128-31.
(38) Ayala-Nunez et al. Zika virus enhances monocyte adhesion and transmigration favoring viral dissemination to neural cells. (2019) *Nat. Commun.* 10:4430.
(39) Moyes et al. Genetically Engineered Macrophages: A Potential Platform for Cancer Immunotherapy. (2017) *Hum. Gene Ther.* 28:200-215.
(40) Muraoka et al. Antigen delivery targeted to tumor-associated macrophages overcomes tumor immune resistance. (2019) *J. Clin. Invest.* 129:1278-1294.
(41) Sanchez-Torres et al. $CD16^+$ and $CD16^-$ human blood monocyte subsets differentiate in vitro to dendritic cells with different abilities to stimulate $CD4^+$ T cells. (2001) *Int. Immunol.* 13:1571-1581.

(42) Kapellos et al. Human Monocyte Subsets and Phenotypes in Major Chronic Inflammatory Diseases. (2019) *Front. Immunol.* 10:2035.
(43) Ding et al. Improving Tumor Accumulation of Aptamers by Prolonged Blood Circulation. (2020) *Anal. Chem.* 92:4108-4114.
(44) Shigdar et al. Aptamers as theranostic agents: modifications, serum stability and functionalisation. (2013) *Sensors* (Basel) 13:13624-13637.

Example 2: Application of A2 Aptamer for Monocyte Depletion from Mixed Cell Populations The ability of the A2 aptamer to isolate monocytes from leukocytes obtained from apheresis product was then tested. 3.75 million cells from apheresis product were exposed to 50 nM A2 aptamer followed by 20 µL magnetic microbeads that can bind to the biotin tag on the aptamer. The solution was applied to a magnetic column and unlabeled cells were flowed through. Greater than 99% of the monocytes were captured on the column, substantially depleting the flow through of monocytes.

Equipment and Reagents

1. Miltenyi MACS separator
2. MS column (cat #130-042-201; can retain 10 million target cells max)
3. 20 µL anti-biotin Microbeads (cat #130-090-485) Monoclonal anti-biotin antibody coupled to Microbeads (50-nm superparamagnetic particles made of dextran and iron oxide)
4. 100 µL 50 nM biotinylated A2 (annealed in wash buffer at 1 µM, apparent Kd~20 nM)
   /5Biosg//iSp18/
   ATCCAGAGTGACGCAGCAGAAGAGTAGAT-GAAA CGTTTTTTCGCCCGATAAAAGGGACG-TGCGTCAGACATGGACA CGGTGGCTTAGT (SEQ ID NO:3)
5. 3.75 million total apheresis cells input
6. Wash buffer: 2.25 g glucose+2.5 mL 1M $MgCl_2$+497.5 mL DPBS (Corning, with $CaCl_2$ and $MgCl_2$)
7. Binding buffer: wash buffer+0.5% BSA (Miltenyi)+0.1 mg/mL tRNA (Invitrogen)
*Avoid EDTA in the system Methods Stain Cells
1. Wash cells once with wash buffer 0.5% BSA
2. Make 100 µL 50 nM A2 in binding buffer (keep all regents cold until applying to column)
3. Resuspend cells in the A2 solution
4. Incubate at 4° C. for 20 minutes on rotation
5. Spin down cells and aspirate supernatant
6. Resuspend cells in 100 µL binding buffer and add 20 µL anti-biotin Microbeads
7. Incubate at 4° C. for 20 minutes on rotation
8. Spin down cells and aspirate excess beads
9. Resuspend in 1000 µL binding buffer Column Preparation
1. Anchor MS column on the separator
2. Wash MS column with 500 µL binding buffer Cell Isolation
1. Apply 1000 µL cells in binding buffer to the MS column
2. Collect flow throughs into new tubes
3. Wash columns 3× with 1 mL wash buffer with 0.5% BSA and collect washes into the same tube and label as flow through (total~3.5 mL)
4. Take column off the separator and flush (using a plunger) with 3 ml of wash buffer with 0.5% BSA into new tube, label as flush Results Small scale testing with MS column on 3.75 M total apheresis cells. 2.85 M cells in flow through. 0.9 M retained in the column.

Labeled cells with 50 nM A2 first, then 20 µL Miltenyi microbeads.

Many dying cells were observed in the flush fraction, which may have interfered with antibody staining. The dying cells were gated out, so the total cell type percentage is closer to 100%.

TABLE 5

| Cell type percentages | Pre-sort | Monocyte A2 50 nM Captured (flush) | Monocyte A2 50 nM Not captured (flow through) |
| --- | --- | --- | --- |
| NKT cells $CD3^+$ $CD56^+$ | 1.91 | 1.83 | 2.4 |
| NK cells $CD3^-$ CD56+ | 9.11 | 10 | 9.8 |
| Monocytes $CD14^+$ | 5.13 | 29 | 0.04 |
| B cells CD $14^-$ CD $19^+$ | 17.2 | 9.82 | 14.4 |
| CD4 T cells $CD3^+$ $CD4^+$ | 42 | 19.9 | 46 |
| CD8 T cells $CD3^+$ $CD4^-$ | 21.8 | 16.4 | 25.4 |
| Total | 97.15 | 86.95 | 98 |

TABLE 6

| Purity of monocyte retained in the column | Yield of captured monocyte |
| --- | --- |
| 29% | ~100 % |

The embodiments of the invention in which an exclusive property or privilege is claimed are defined as follows:

1. A composition comprising an aptamer that specifically binds to a monocyte and/or a macrophage, wherein the aptamer comprises a sequence having at least 75% sequence identity to SEQ ID NO:1; and wherein the aptamer can further comprise a number (N) of nucleotides (nt) at each end wherein each nucleotide is selected independently, and wherein each N comprises from 3 nt to 30 nt, from 3 nt to 20 nt, or from 3 nt to 10 nt;
wherein any nucleotide change in the sequence of the aptamer relative to SEQ ID NO:1 occurs within one or more stem regions of SEQ ID NO:1 and co-occurs with one or more compensatory nucleotide changes within the one or more stem regions of SEQ ID NO:1 to maintain double-strandedness of the one or more stem regions of SEQ ID NO:1.

2. The composition of claim 1, wherein the aptamer comprises a sequence having at least 75% identity to SEQ ID NO:2 and any nucleotide change in the sequence of the aptamer relative to SEQ ID NO:2 occurs within one or more stem regions of SEQ ID NO:2 and co-occurs with one or more compensatory nucleotide changes within the one or more stem regions of SEQ ID NO:2 to maintain double-strandedness of the one or more stem regions of SEQ ID NO: 2; or wherein the aptamer comprises a sequence having at least 75% identity to SEQ ID NO:3 and any nucleotide change in the sequence of the aptamer relative to SEQ ID NO:3 occurs within one or more stem regions of SEQ ID NO:3 and co-occurs with one or more compensatory nucleotide changes within the one or more stem regions of SEQ ID NO:3 to maintain double-strandedness of the one or more stem regions of SEQ ID NO:3.

3. The composition of claim 1, wherein the monocyte and/or macrophage expresses CD14.

4. The composition of claim 1, wherein the macrophage is an M0 or M2 macrophage.

5. The composition of claim 1, wherein the aptamer comprises at least five single-stranded loops and at least four double-stranded stems.

6. The composition of claim 1, wherein the aptamer comprises the sequence of SEQ ID NO:1.

7. The composition of claim 1, wherein the aptamer is attached to a solid support or phase-changing agent.

8. The composition of claim 1, wherein the aptamer further comprises a detectable moiety, a label, a tag, or a probe.

9. The composition of claim 1, formulated for use as a drug delivery device, or for use as a sensor.

10. A cell displaying an aptamer that specifically binds to a monocyte and/or a macrophage, wherein the aptamer comprises a sequence having at least 75% sequence identity, or differs by less than three nucleotides, to SEQ ID NO:1, SEQ ID NO:2, or SEQ ID NO:3;

wherein any nucleotide change in the sequence of the aptamer relative to SEQ ID NO:1, SEQ ID NO: 2, or SEQ ID NO:3 occurs within one or more stem regions of SEQ ID NO:1, SEQ ID NO: 2, or SEQ ID NO:3 and co-occurs with one or more compensatory nucleotide changes within the one or more stem regions of SEQ ID NO:1, SEQ ID NO: 2, or SEQ ID NO:3 to maintain double-strandedness of the one or more stem regions of SEQ ID NO:1, SEQ ID NO: 2, or SEQ ID NO: 3.

11. A method for isolating or enriching monocytes and macrophages from a biological sample comprising a plurality of cell types, the method comprising:
(i) contacting the biological sample with an aptamer of claim 1 that specifically binds a monocyte and/or macrophage under conditions that permit forming aptamer-bound cells; and
(ii) separating the aptamer-bound cells from cells not bound to the aptamer.

12. The method of claim 11, wherein the biological sample comprises a blood sample or a processed blood sample.

13. The method of claim 11, wherein the aptamer is attached to a solid support or phase-changing agent.

14. The method of claim 11, wherein the aptamer further comprises a detectable moiety, a label, a tag, or a probe.

15. A method for depleting monocytes and macrophages from a biological sample comprising a plurality of cell types, the method comprising:
(i) contacting the biological sample with an aptamer of claim 1 that specifically binds a monocyte and/or macrophage under conditions that permit forming an aptamer-bound cell;
(ii) separating the aptamer-bound cells from cells not bound to the aptamer; and
(iii) recovering the cells not bound to the aptamer by removing aptamer-bound cells,
whereby the monocytes and/or macrophages are depleted from the biological sample.

16. The method of claim 15, wherein the biological sample comprises a blood sample or a processed blood sample.

17. A pharmaceutical composition comprising an aptamer of claim 1.

18. A method of treating a disease, the method comprising: administering the isolated or enriched monocytes and/or macrophages of claim 11 or an engineered or differentiated cell thereof to a subject in need thereof, thereby treating the disease.

19. A method of treating a disease, the method comprising administering the recovered cells of claim 15 or an engineered or differentiated cell thereof to a subject in need thereof, thereby treating the disease.

20. A method of delivering a therapeutic agent, the method comprising administering an aptamer comprising a sequence having at least 75% sequence identity to SEQ ID NO:1, SEQ ID NO: 2, or SEQ ID NO:3, wherein the aptamer is attached to a therapeutic drug or therapeutic cell;

wherein any nucleotide change in the sequence of the aptamer relative to SEQ ID NO:1, SEQ ID NO: 2, or SEQ ID NO:3 occurs within one or more stem regions of SEQ ID NO:1, SEQ ID NO: 2, or SEQ ID NO:3 and co-occurs with one or more compensatory nucleotide changes within the one or more stem regions of SEQ ID NO:1, SEQ ID NO: 2, or SEQ ID NO:3 to maintain double-strandedness of the one or more stem regions of SEQ ID NO:1, SEQ ID NO: 2, or SEQ ID NO: 3.

* * * * *

UNITED STATES PATENT AND TRADEMARK OFFICE
CERTIFICATE OF CORRECTION

PATENT NO. : 12,215,324 B2  
APPLICATION NO. : 17/849513  
DATED : February 4, 2025  
INVENTOR(S) : Suzie Hwang Pun et al.

Page 1 of 1

It is certified that error appears in the above-identified patent and that said Letters Patent is hereby corrected as shown below:

On the Title Page

| Column | Line | |
|---|---|---|
| 1 | 2 | item (71), under Applicants, delete "Hospital," and insert -- Hospital d/b/a Seattle Children's Research Institute, -- |
| 1 | 2 | item (73), under Assignees, delete "Hospital," and insert -- Hospital d/b/a Seattle Children's Research Institute, -- |

Signed and Sealed this  
Thirteenth Day of January, 2026

John A. Squires  
*Director of the United States Patent and Trademark Office*

SEQUENCE LISTING

<160> NUMBER OF SEQ ID NOS: 21

<210> SEQ ID NO 1
<211> LENGTH: 46
<212> TYPE: DNA
<213> ORGANISM: Artificial sequence
<220> FEATURE:
<223> OTHER INFORMATION: Synthetic

<400> SEQUENCE: 1

```
agcagaagag tagatgaaac gttttttcgc ccgataaaag ggacgt           46

<210> SEQ ID NO 2
<211> LENGTH: 64
<212> TYPE: DNA
<213> ORGANISM: Artificial sequence
<220> FEATURE:
<223> OTHER INFORMATION: Synthetic

<400> SEQUENCE: 2
ttatgacgca gcagaagagt agatgaaacg ttttttcgcc cgataaaagg gacgtgcgtc    60
ataa                                                                64

<210> SEQ ID NO 3
<211> LENGTH: 88
<212> TYPE: DNA
<213> ORGANISM: Artificial sequence
<220> FEATURE:
<223> OTHER INFORMATION: Synthetic

<400> SEQUENCE: 3
atccagagtg acgcagcaga agagtagatg aaacgttttt tcgcccgata aagggacgt    60 gcgtcagaca tggacacggt ggcttagt                                      88

<210> SEQ ID NO 4
<211> LENGTH: 12
<212> TYPE: DNA
<213> ORGANISM: Artificial sequence
<220> FEATURE:
<223> OTHER INFORMATION: Synthetic

<400> SEQUENCE: 4
agaagagtag at                                                       12

<210> SEQ ID NO 5
<211> LENGTH: 16
<212> TYPE: DNA
<213> ORGANISM: Artificial sequence
<220> FEATURE:
<223> OTHER INFORMATION: Synthetic

<400> SEQUENCE: 5
cagcgaaacg gacgtg                                                   16

<210> SEQ ID NO 6
<211> LENGTH: 19
<212> TYPE: DNA
<213> ORGANISM: Artificial sequence
<220> FEATURE:
<223> OTHER INFORMATION: Synthetic

<400> SEQUENCE: 6
atcgacacgg tggcttagt                                                19

<210> SEQ ID NO 7
<211> LENGTH: 18
<212> TYPE: DNA
<213> ORGANISM: Artificial sequence
<220> FEATURE:
<223> OTHER INFORMATION: Synthetic

<400> SEQUENCE: 7
atccagagtg acgcagca                                                 18
```

```
<210> SEQ ID NO 8
<211> LENGTH: 18
<212> TYPE: DNA
<213> ORGANISM: Artificial sequence
<220> FEATURE:
<223> OTHER INFORMATION: Synthetic

<400> SEQUENCE: 8
tggacacggt ggcttagt                                              18

<210> SEQ ID NO 9
<211> LENGTH: 52
<212> TYPE: DNA
<213> ORGANISM: Artificial sequence
<220> FEATURE:
<223> OTHER INFORMATION: Synthetic

<400> SEQUENCE: 9
gaagagtaga tgaaacgttt tttcgcccga taaaagggac gtgcgtcaga ca        52

<210> SEQ ID NO 10
<211> LENGTH: 52
<212> TYPE: DNA
<213> ORGANISM: Artificial sequence
<220> FEATURE:
<223> OTHER INFORMATION: Synthetic

<400> SEQUENCE: 10
atgatagtga cgtacggact agggatcacc catatcatgt agaggaagta cg        52

<210> SEQ ID NO 11
<211> LENGTH: 18
<212> TYPE: DNA
<213> ORGANISM: Artificial sequence
<220> FEATURE:
<223> OTHER INFORMATION: Synthetic

<400> SEQUENCE: 11
atccagagtc acgcagca                                              18

<210> SEQ ID NO 12
<211> LENGTH: 18
<212> TYPE: DNA
<213> ORGANISM: Artificial sequence
<220> FEATURE:
<223> OTHER INFORMATION: Synthetic

<400> SEQUENCE: 12
actaagccac cgtgtcca                                              18

<210> SEQ ID NO 13
<211> LENGTH: 20
<212> TYPE: DNA
<213> ORGANISM: Artificial sequence
<220> FEATURE:
<223> OTHER INFORMATION: Synthetic

<400> SEQUENCE: 13
gcatccagag tgacgcagca                                            20

<210> SEQ ID NO 14
<211> LENGTH: 20
<212> TYPE: DNA
<213> ORGANISM: Artificial sequence
<220> FEATURE:
<223> OTHER INFORMATION: Synthetic
```

```
<400> SEQUENCE: 14
gcactaagcc accgtgtcca                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic

<400> SEQUENCE: 15
aaactgctcg ccagaacact                                              20

<210> SEQ ID NO 16
<211> LENGTH: 20
<212> TYPE: DNA
<213> ORGANISM: Artificial sequence
<220> FEATURE:
<223> OTHER INFORMATION: Synthetic

<400> SEQUENCE: 16
catgggctac accttgacct                                              20

<210> SEQ ID NO 17
<211> LENGTH: 29
<212> TYPE: DNA
<213> ORGANISM: Artificial sequence
<220> FEATURE:
<223> OTHER INFORMATION: Motif 1
<220> FEATURE:
<221> NAME/KEY: misc_feature
<222> LOCATION: (11)..(29)
<223> OTHER INFORMATION: n is a, c, g, or t

<400> SEQUENCE: 17
cggyacccct nnnnnnnnnn nnnnnnnnn                                    29

<210> SEQ ID NO 18
<211> LENGTH: 29
<212> TYPE: DNA
<213> ORGANISM: Artificial sequence
<220> FEATURE:
<223> OTHER INFORMATION: Motif 2
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
```

```
<400> SEQUENCE: 18
nagnctccna tnccgggnwn kysskknsk                                      29

<210> SEQ ID NO 19
<211> LENGTH: 17
<212> TYPE: DNA
<213> ORGANISM: Artificial sequence
<220> FEATURE:
<223> OTHER INFORMATION: Motif 3
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 19
yrccaccaag attmnrn                                                   17

<210> SEQ ID NO 20
<211> LENGTH: 21
<212> TYPE: DNA
<213> ORGANISM: Artificial sequence
<220> FEATURE:
<223> OTHER INFORMATION: Motif 4

<400> SEQUENCE: 20
atcgkgttaa actagaaagc r                                              21

<210> SEQ ID NO 21
<211> LENGTH: 88
<212> TYPE: DNA
<213> ORGANISM: Artificial sequence
<220> FEATURE:
<223> OTHER INFORMATION: DNA aptamer A2

<400> SEQUENCE: 21
atccagagtg acgcagcaga agagtagatg aaacgttttt tcgcccgata aagggacgt     60 gcgtcagaca tggacacggt ggcttagt                                       88
```